US011197856B2

United States Patent
Glass et al.

(10) Patent No.: US 11,197,856 B2
(45) Date of Patent: *Dec. 14, 2021

(54) BICYCLIC COMPOUNDS AND METHODS FOR THEIR USE IN TREATING AUTISM

(71) Applicant: Neuren Pharmaceuticals Limited, Auckland (NZ)

(72) Inventors: Lawrence Irwin Glass, Takoma Park, MD (US); Michael John Bickerdike, Auckland (NZ); Michael Frederick Snape, Surrey (GB); Patricia Cogram, Oxford (GB)

(73) Assignee: NEUREN PHARMACEUTICALS LIMITED, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 16/749,185

(22) Filed: Jan. 22, 2020

(65) Prior Publication Data
US 2020/0163961 A1 May 28, 2020

Related U.S. Application Data

(63) Continuation of application No. 15/869,672, filed on Jan. 12, 2018, now Pat. No. 10,548,892, which is a continuation of application No. 15/004,218, filed on Jan. 22, 2016, now Pat. No. 9,867,823, which is a continuation of application No. PCT/US2014/047801, filed on Jul. 23, 2014.

(60) Provisional application No. 61/958,329, filed on Jul. 25, 2013.

(51) Int. Cl.
| A61K 31/499 | (2006.01) |
| A61K 31/498 | (2006.01) |
| A61K 45/06 | (2006.01) |
| A61K 31/4985 | (2006.01) |
| A61K 31/551 | (2006.01) |

(52) U.S. Cl.
CPC .......... *A61K 31/499* (2013.01); *A61K 31/498* (2013.01); *A61K 31/4985* (2013.01); *A61K 31/551* (2013.01); *A61K 45/06* (2013.01)

(58) Field of Classification Search
None
See application file for complete search history.

(56) References Cited

U.S. PATENT DOCUMENTS

2009/0074865 A1* 3/2009 Wen ..................... A61K 9/1075 424/474
2011/0201614 A1* 8/2011 Bickerdike .......... A61K 31/498 514/249

OTHER PUBLICATIONS

Suzuki "Reduced Acetylcholinesterase Activity in the Fusiform Gyrus in Adults With Autism Spectrum Disorders" arch gen psychiatry 68(3) (Year: 2011).*
Riedel "Scopolamine-induced deficits in social memory in mice: Reversal by donepezil" Behavioural Brain Research 204 (2009) 217-225 (Year: 2009).*
Deutsch, Steven I. et al., Clinical Neuropharmacology: 33(3): p. 114-120 (May 2010); doi:10.1097/WNF.obo13e318id6f7ad.
Perry, Elaine K. et al., Am. J. Psychiatry 158(7): 1058 (2001); doi.org/10.1176/appl.ajp.158.7,1058.
Perry, Elaine et. al., Cholinergic Activity in Autism: Abnormalities in the Cerebral Cortex and Basal Forebrain, Am. J. Psychiatry 158(7):1058-1066 (2001).
Riikonen, Raili et al., Cerebrospinal fluid insulin-like growth factors IGF-1 and IGF-2 in infantile autism, Developmental Medicine and Child Neurology 48:751-755 (2006).
Lippiello, P.M. Nicotinic cholinergic antagonists: A novel approach for the treatment of autism, Medical Hypotheses 66:985-990 (2006).
Rossier, A.M. et al., Regional brain activity during shape recognition impaired by a scopolamine challenge to encoding, Eur. J. Neurosci. 11(10):3701-3714 (1999).
Thiel, Christiane et al., Scopolamine but not Lorazepam Modulates Face Repetition Priming: A Psychopharmacological fMRI Study, Neuropsychopharmacology 27(2):282-292 (2002).
Schon, Karin et al., Scopolamine Reduces Persistent Activity Related to Long-Term Encoding in the Parahippocampal Gyrus during Delayed Matching in Humans.
J. Neurosci. 25(40):9112-9123 (2005).
Sperling, Reisa et al., Functional MRI detection of pharmacologically induced memory impairment. Proc. Nat. Academy of Sci. 99(1):455-460 (2002).

* cited by examiner

*Primary Examiner* — Adam Weidner
(74) *Attorney, Agent, or Firm* — D. Benjamin Borson; Borson Law Group PC

(57) ABSTRACT

Embodiments of this invention provide compositions and methods for therapeutic use of diketopiperazines including cyclic G-2-Allyl Proline and other cyclic Glycyl Proline compounds to treat symptoms of Autistic Disorder or Autism, as well as manufacture of medicaments including tablets, capsules, liquid formulations, gels, injectable solutions, and other formulations that are useful for treatment of such conditions.

24 Claims, 65 Drawing Sheets
(2 of 65 Drawing Sheet(s) Filed in Color)

BICYCLIC COMPOUNDS AND METHODS FOR THEIR USE IN TREATING AUTISM

CLAIM OF PRIORITY

This United States Continuation application is filed under 35 U.S.C. § 111a, claims priority to U.S. patent application Ser. No. 15/869,672 filed 12 Jan. 2018 (U.S. Pat. No. 10,548,892, issued 4 Feb. 2020), which claims priority to U.S. patent application Ser. No. 15/004,218 filed 22 Jan. 2016 (now U.S. Pat. No. 9,867,823, issued 16 Jan. 2018, which is a continuation of International Patent Application No. PCT/US2014/047801, filed Jul. 23, 2014, entitled "Neuroprotective Bicyclic Compounds and Methods for Their Use in Treating Autism Spectrum Disorders and Neurodevelopmental Disorders," Inventors Lawrence Irwin Glass, Michael John Bickerdike, Michael Fredrick Snape, and Patricia Perez de Cogram, which claims priority to U.S. Provisional Patent Application No. 61/958,329 filed 25 Jul. 2013 entitled "Neuroprotective Bicyclic Compounds and Methods for Their Use in Treating Autism Spectrum Disorders and Neurodevelopmental Disorders," Inventors Lawrence Irwin Glass, Michael John Bickerdike, Michael Fredrick Snape, and Patricia Perez de Cogram. Each of these patents and patent applications are incorporated herein fully by reference.

FIELD OF THE INVENTION

The present invention relates to novel bicyclic compounds structurally related to diketopiperazines and methods for their therapeutic use. In particular, this invention relates to the neuroprote active activity of such compounds. More particularly, this invention relates to the use of cyclic Glycyl Proline ("cPG") and analogs thereof, including cyclic Glycyl-2-Allyl Proline ("cyclic G-2-AllylP" or "cG-2-AllylP" or "NNZ 2591") and pharmaceutical compositions thereof in the treatment of Neurodevelopmental Disorders, and particularly directed to treatment of Autistic Disorder and autism.

BACKGROUND

Autism Spectrum Disorders (ASDs) are increasingly being diagnosed. ASDs are a collection of linked developmental disorders, characterized by abnormalities in social interaction and communication, restricted interests, and repetitive behaviours. In addition to classical autism or Autistic Disorder, the fifth edition of the American Psychiatric Association's (APA) *Diagnostic and Statistical Manual of Mental Disorders* (DSM-5) recognizes Autistic Disorder, Asperger syndrome, Childhood Disintegrative Disorder, and Pervasive Developmental Disorder Not Otherwise Specified (PDD-NOS) as ASDs.

Neurodevelopmental Disorders (NDDs) include Fragile X Syndrome (FXS), Angelman Syndrome, Tuberous Sclerosis Complex, Phelan McDermid Syndrome, Rett Syndrome, CDKL5 mutations (which also are associated with Rett Syndrome and X-Linked Infantile Spasm Disorder) and others. Many but not all NDDs are caused by genetic mutations and, as such, are sometimes referred to as monogenic disorders. Some patients with NDDs exhibit behaviors and symptoms of autism.

As an example of a NDD, Fragile X Syndrome is an X-linked genetic disorder in which affected individuals are intellectually handicapped to varying degrees and display a variety of associated psychiatric symptoms. Clinically, Fragile X Syndrome is characterized by intellectual handicap, hyperactivity and attentional problems, autism spectrum symptoms, emotional lability and epilepsy (Hagerman, 1997a). The epilepsy seen in Fragile X Syndrome is most commonly present in childhood, but then gradually remits towards adulthood. Hyperactivity is present in approximately 80 percent of affected males (Hagerman, 1997b). Physical features such as prominent ears and jaw and hyper-extensibility of joints are frequently present but are not diagnostic. Intellectual handicap is the most common feature defining the phenotype. Generally, males are more severely affected than females. Early impressions that females are unaffected have been replaced by an understanding of the presence of specific learning difficulties and other neuropsychiatric features in females. The learning disability present in males becomes more defined with age, although this longitudinal effect is more likely a reflection of a flattening of developmental trajectories rather than an explicit neurodegenerative process.

The compromise of brain function seen in Fragile X Syndrome is paralleled by changes in brain structure in humans. MRI scanning studies reveal that Fragile X Syndrome is associated with larger brain volumes than would be expected in matched controls and that this change correlates with trinucleotide expansion in the FMRP promoter region (Jakala et al., 1997). At the microscopic level, humans with Fragile X Syndrome show abnormalities of neuronal dendritic structure, in particular, an abnormally high number of immature dendritic spines (Irwin et al., 2000).

Currently available treatments for NDDs are symptomatic—focusing on the management of symptoms—and supportive, requiring a multidisciplinary approach. Educational and social skills training and therapies are implemented early to address core issues of learning delay and social impairments. Special academic, social, vocational, and support services are often required. Medication, psychotherapy or behavioral therapy may be used for management of co-occurring anxiety, Attention Deficit Hyperactivity Disorder ("ADHD"), depression, maladaptive behaviors such as aggression, and sleep issues. Antiepileptic drugs may be used to control seizures.

SUMMARY

We have previously shown in patent application PCT/US2004/02830 filed Aug. 31, 2004, expressly incorporated herein fully by reference, that cyclic Glycyl Proline ("cPG") and analogues thereof, including but not limited to cyclic cyclopentyl-G-2-MeP and cyclic-G-2-AllylP ) "cG-2-AllylP") are neuroprotective and neuroregenerative. There is no current, effective treatment of ASDs or NDDs, and patient care is limited to management of the symptoms, predominantly using social and behavioural interventions. The inventors have now discovered that cyclic G-2-AllylP and other bicyclic compounds disclosed herein can be effective in treatment of ASDs and NDDs, and in particular for normalizing abnormal social behavior.

We unexpectedly discovered that cG-2-AllylP has a robust therapeutic effect on anxiety, hyperactivity, memory, learning and species-typical abnormal social behaviour and repetitive behavior in animals having Fragile X Syndrome ("FXS") or other ASDs. In addition, we found that changes in ERK1/2 and Akt phosphorylation in cG-2-AllylP treated fmr1-knockout animals, provides an in vitro diagnostic evaluation of ASDs, and support the hypothesis that the phenotypes of Fragile X Syndrome are the result of altered mGluR expression. Moreover, administration of cG-2-AllylP significantly reduced the numbers of neuronal spines in fmr1-knockout mice.

Because the fmr1-knockout animals used for in vivo studies disclosed herein have the same genetic mutation as human beings with Fragile X Syndrome, administration of cyclic Glycyl Proline ("cGP") compounds of this invention, including cG-2-AllylP, can be useful in treating symptoms of Autism Spectrum Disorders, Neurodevelopmental Disorders and Fragile X Syndrome in human beings. In addition, we unexpectedly found that cGPs of this invention can effectively treat adverse social behaviors and repetitive behaviors in animals with ASDs, thus restoring more normal social interactions.

Thus, one aspect of this invention provides novel cyclic compounds having the structural formulas and substituents described below.

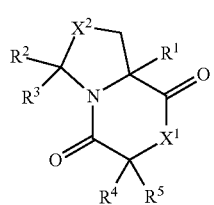

Formula 1

In some aspects, compounds of Formula 1 include substituents where:

$X^1$ is selected from the group consisting of NR', O and S;

$X^2$ is selected from the group consisting of $CH_2$, NR', O and S;

$R^1$, $R^2$, $R^3$, $R^4$ and $R^5$ are independently selected from the group consisting of —H, —OR', —SR', —NR'R', —NO$_2$, —CN, —C(O)R', —C(O)OR', —C(O)NR'R', —C(NR') NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl; or $R^4$ and $R^5$ taken together are —CH$_2$—(CH$_2$)$_n$—CH$_2$— where n is an integer from 0-6; or $R^2$ and $R^3$ taken together are —CH$_2$—(CH$_2$)$_n$—CH$_2$— where n is an integer from 0-6; with the proviso that when $R^1$=methyl and $R^2$=$R^3$=$R^4$=H then $R^5$≠benzyl and; when $R^1$=H, at least one of $R^2$ and $R^3$≠H.

In further aspects, this invention provides a compound of Formula 1 or a pharmaceutically acceptable salt, stereoisomer or hydrate thereof, wherein $R^1$=allyl, $R^2$=$R^3$=$R^4$=$R^5$=H, $X^1$=NH, $X^2$=$CH_2$ (cyclic Glycyl-2-AllylProline).

In still other aspects, this invention provides pharmaceutical compositions comprising a pharmaceutically acceptable excipient and a therapeutically effective amount of cyclic G-2AllylP.

In further aspects, this invention provides methods of treating an animal having a cognitive impairment, comprising administration to that animal an effective amount of a composition comprising cyclic G-2-AllylP. In yet further aspects, the animal to be treated is a human.

BRIEF DESCRIPTION OF THE DRAWINGS

Color Drawings:

This application file contains at least one drawing executed in color. Copies of this patent or patent application publication with color drawing(s) will be provided by the Office upon request and payment of the necessary fee.

Figure 1:
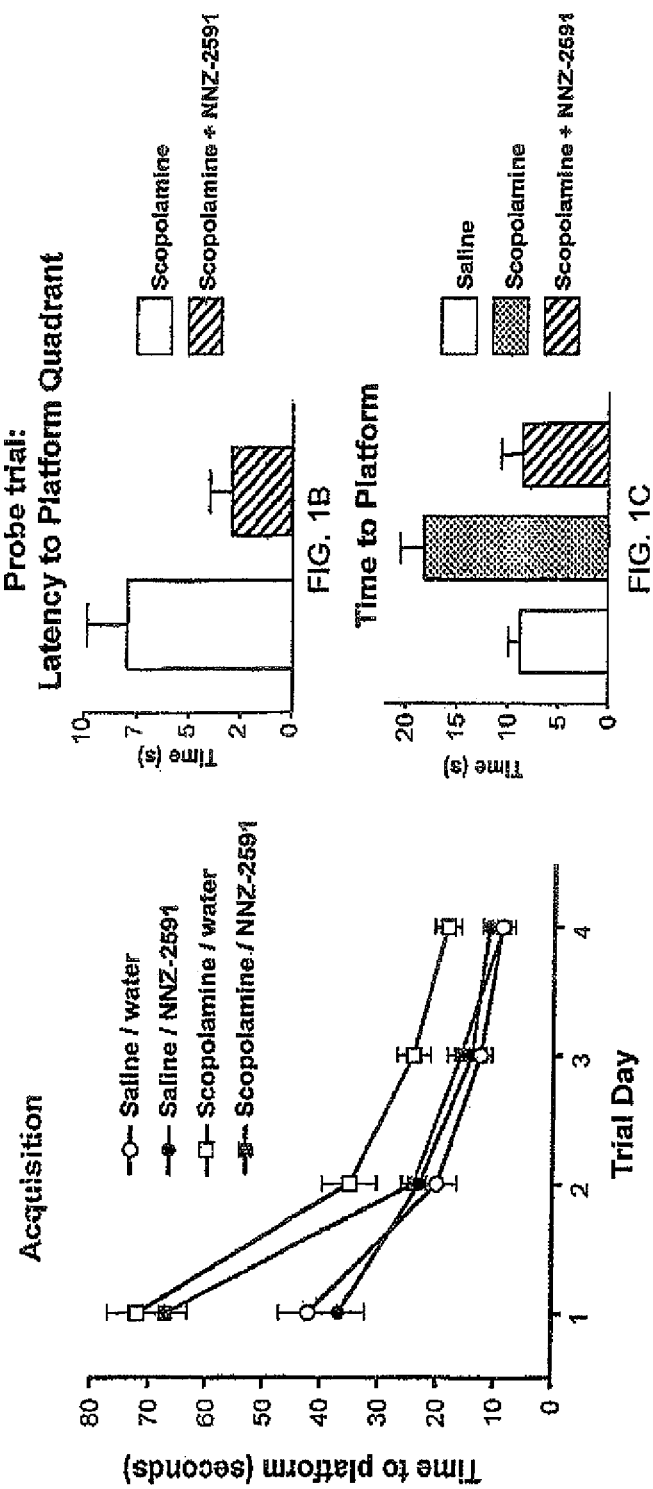

This invention is described with reference to specific embodiments thereof. Other aspects of this invention can be appreciated with reference to the drawings, in which:

FIG. 1A is a graph showing effects of treatment with cyclic G-2-AllylP on the performance in acquisition phase (days 1-4) of the Morris Water Maze Test (MWMT) following scopolamine treatment.

FIG. 1B is a graph showing effects of treatment with cyclic G-2-AllylP on the latency to the platform quadrant in the probe test (day 5) of the MWMT.

FIG. 1C is a graph showing the time taken to find the platform on day $4^{th}$ of the acquisition phase for animals in 3 groups: (1) vehicle-treated, (2) scopolamine and cG-2-AllylP-treated and (3) scopolamine-treated.

Figure 2:
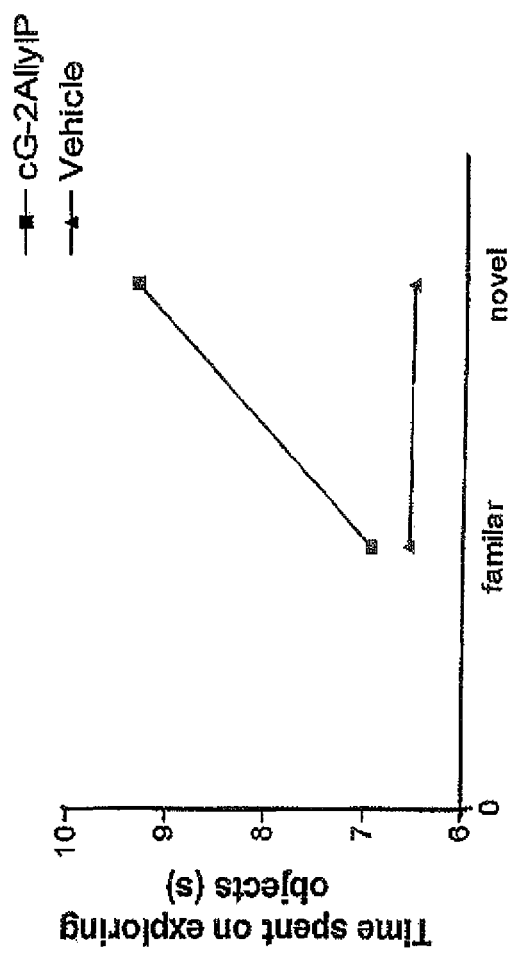

FIG. 2 is a graph showing the difference in time spent on exploring the familiar vs novel object during the probe test on days 25 post-treatment. The data points for familiar objects reflect the average of time spent on exploration of 3 familiar objects. The data point for novel object recognition is the actual time spent exploring the novel object.

Figure 3:
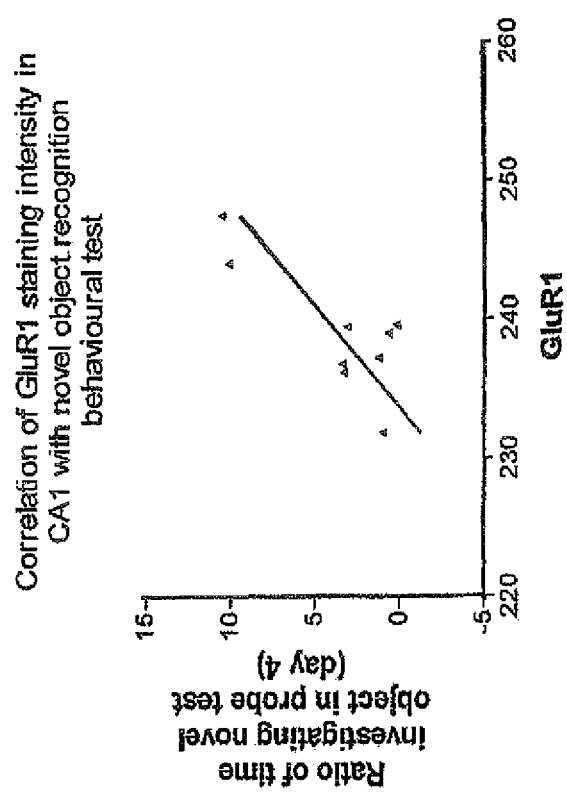

FIG. 3 is a graph showing a correlation between the AMPA glutamate receptor-1 staining of the CA1 region of the hippocampus and the ratio of time spend on investigation of novel object to familiar object in testing phase of the NORT on day 24.

Figure 4:
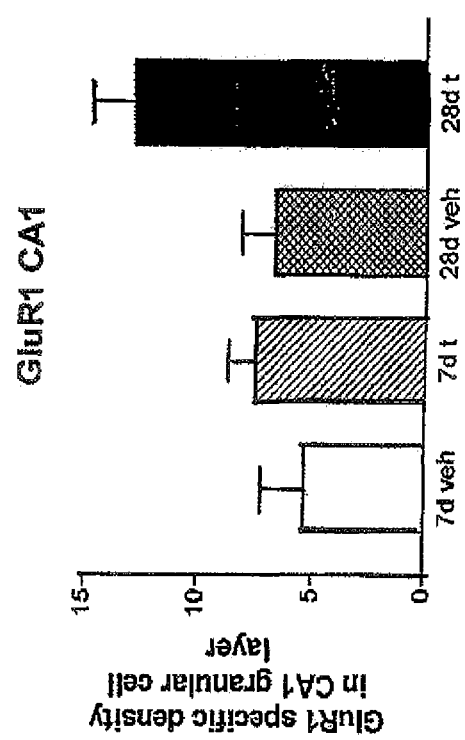

FIG. 4 is a graph showing the effects of cG-2-AllylP (t) on the density of AMPA GluR1 in CA1 granular cell layer on days 6 and 24 in comparison to vehicle (veh).

Figure 5:
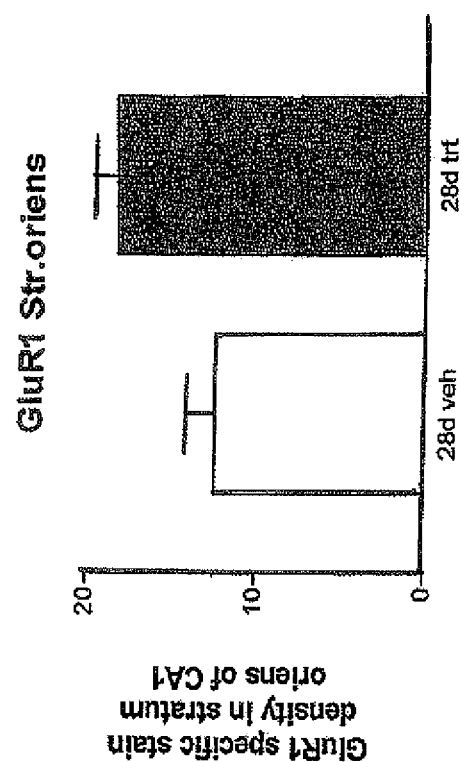

FIG. 5 is a graph showing the effects of cG-2-AllylP (t) on the density of AMPA GluR1 in CA1 stratum oriens on day 24 post treatment.

Figure 6:
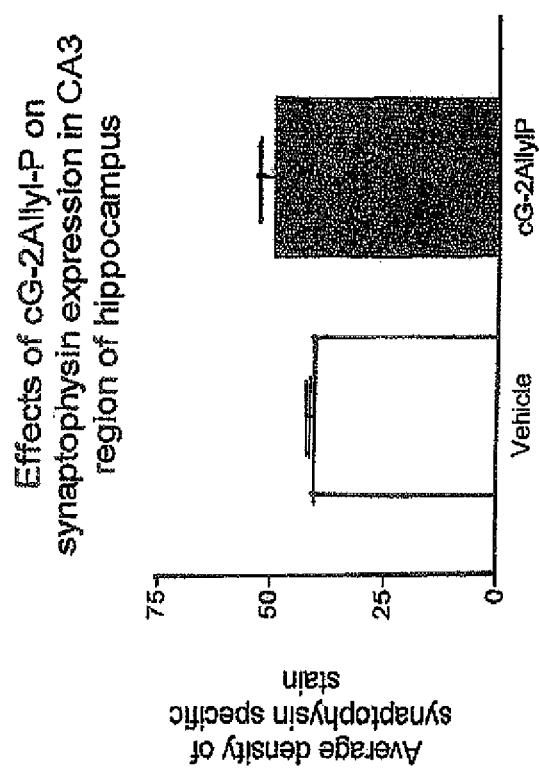

FIG. 6 is a graph showing the effect of cG-2-AllylP on the trend to increase the density of pre-synaptic stain in CA3 region of the hippocampus at day 24 post-treatment.

Figure 7:
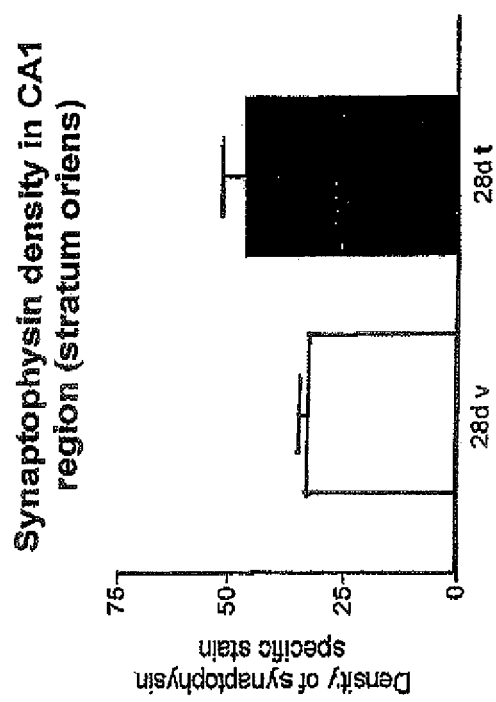

FIG. 7 is a graph showing the effect of cG-2-AllylP on the trend to increase the density of the pre-synaptic stain in the stratum oriens of the CA1 region on day 24 post-treatment.

Figure 8:
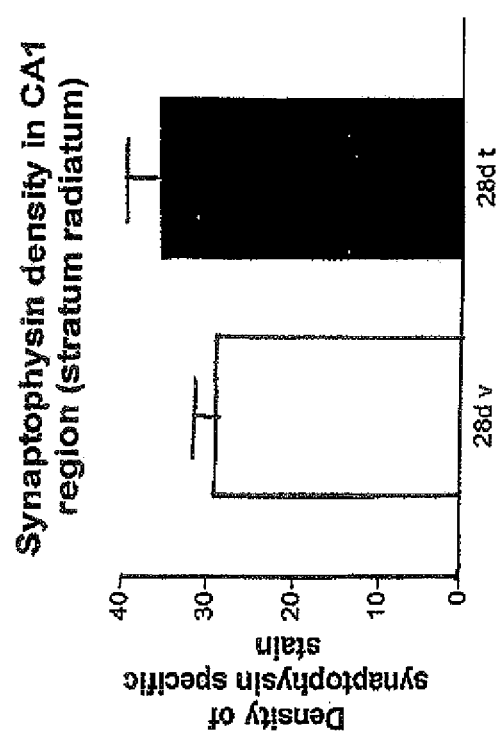

FIG. 8 is a graph showing the effect of cG-2-AllylP to increase the density of the pre-synaptic stain in the stratum radiatum of the CA1 region on day 24 post-treatment.

Figures 9A, 9B:
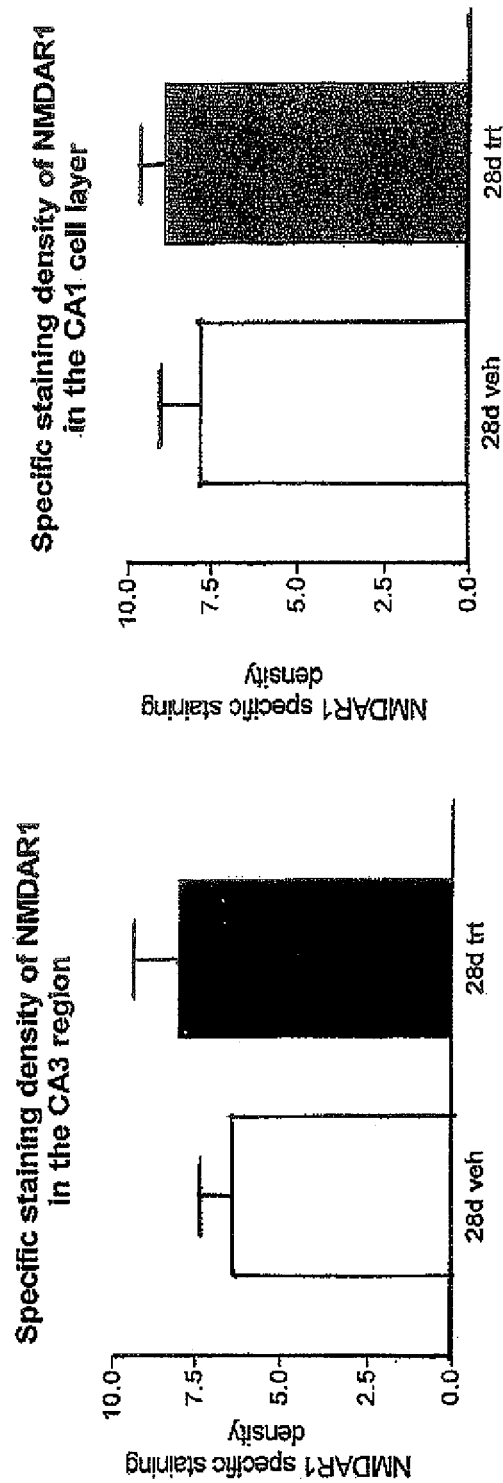
Figure 9C:
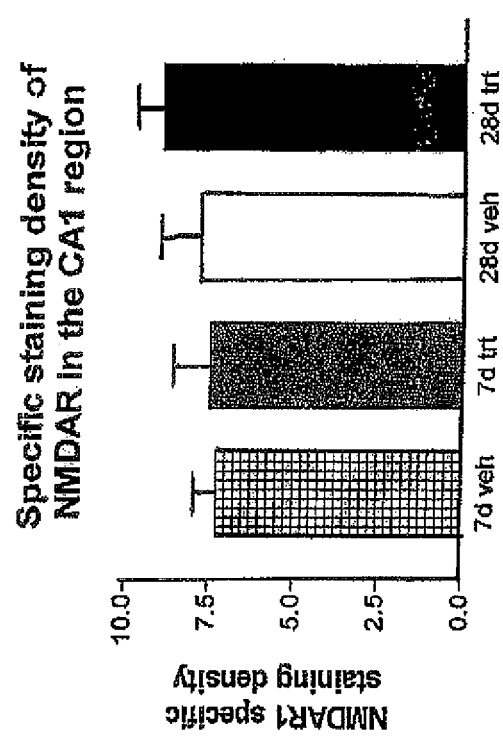

FIGS. 9A, 9B, and 9C are graphs showing the effect of cG-2-AllylP treatment on the density of the NMDAR-1 in CA1 and CA3, respectively.

Figure 10:
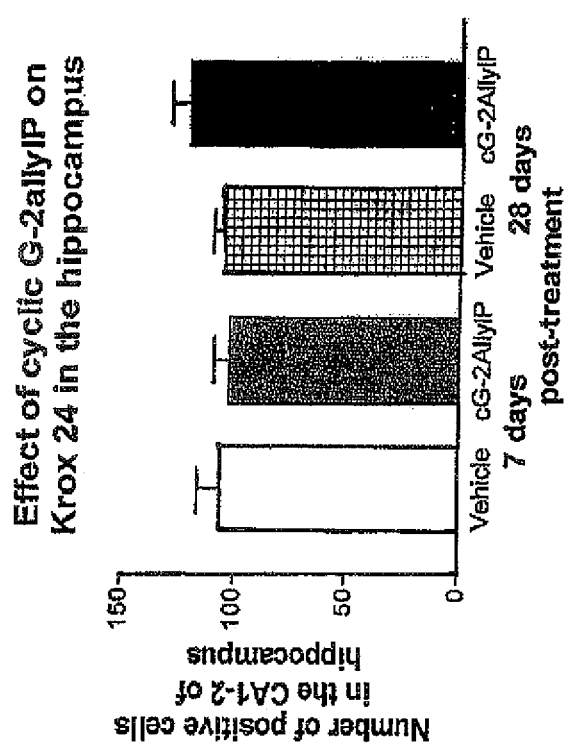

FIG. 10 is a graph showing the effects of cG-2-AllylP on the density of Krox24 staining in the CA1-2 of the hippocampus.

Figure 11:
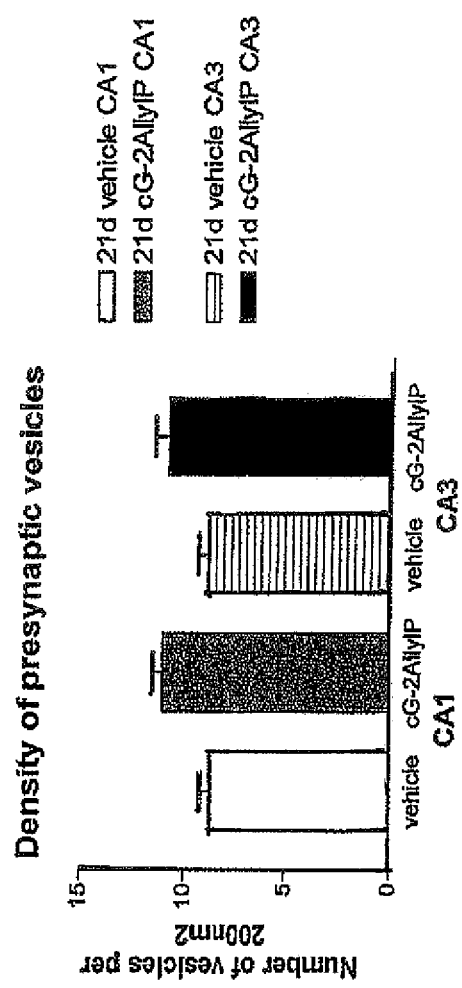

FIG. 11 is a graph showing the effects of cG-2-AllylP on the number of vehicles in a 200 nm$^2$ square apposing the post-synaptic density in subregions CA3 and CA1 of the hippocampus of middle aged rats (n=2 in each group).

Figure 12:
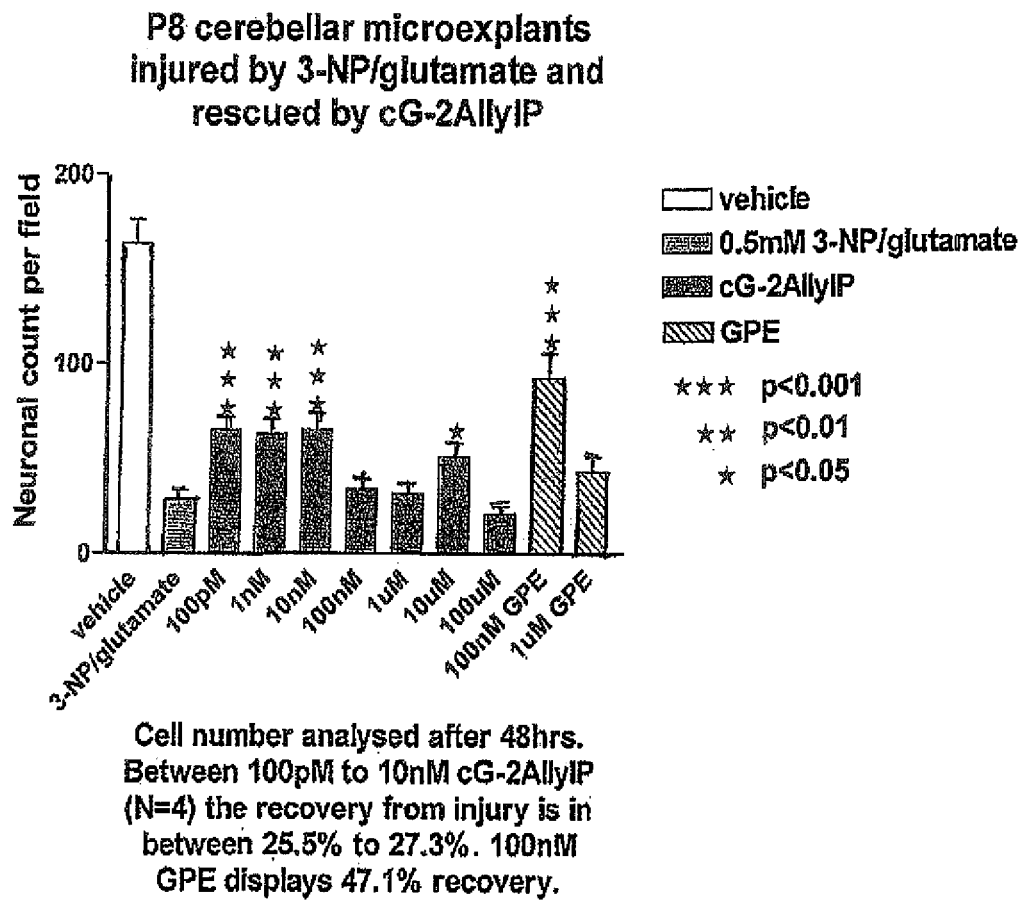

FIG. 12 is a graph showing effects of cyclic G-2-AllylP on neuronal survival in animals following excitotoxic oxidative stress.

Figure 13:
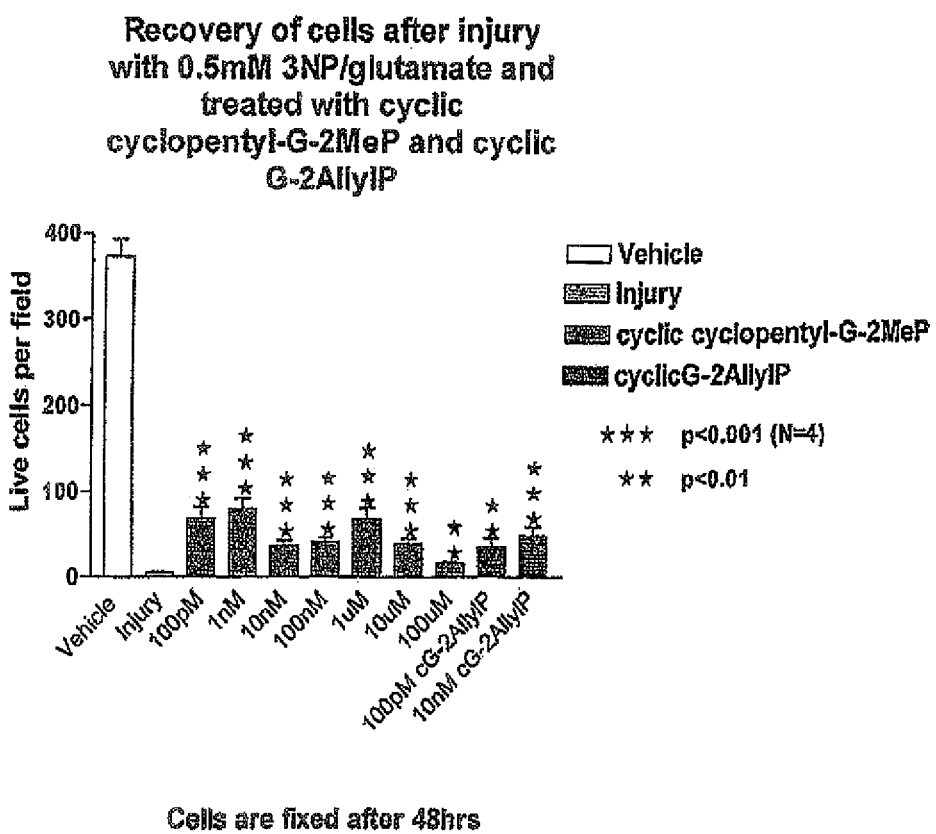

FIG. 13 is a graph showing effects of cyclic cyclopentylG-2-MeP on neuronal survival in animals following excitotoxic oxidative stress.

Figure 14:
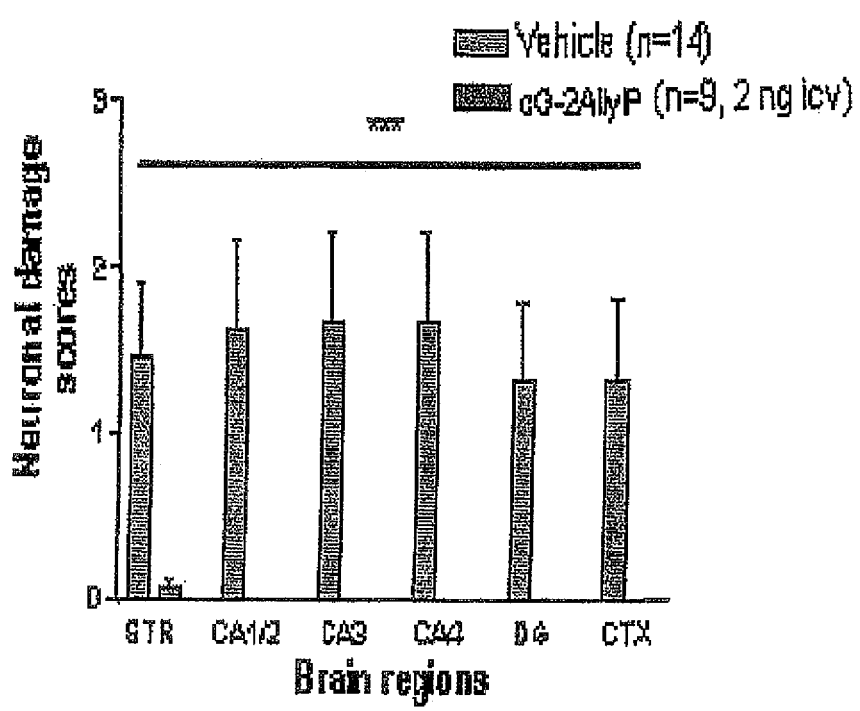

FIG. 14 is a graph showing the neuroprotective effects of cyclic G-2-AllylP in animals subjected to global brain ischaemia.

Figure 15:
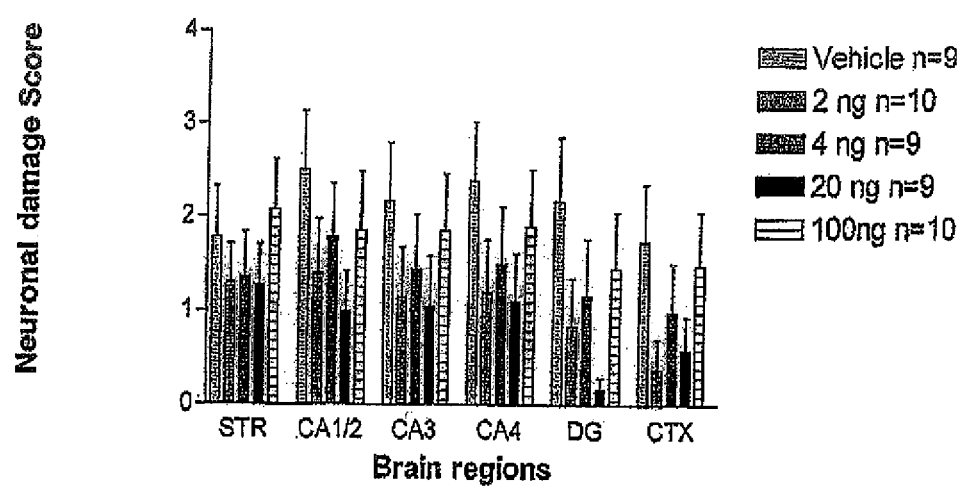

FIG. 15 is a graph showing effects of different doses of cyclic G-2-AllylP on neuroprotection in animals subjected to global brain ischaemia.

FIGS. 16A-D depict a chamber for studies of hippocampal neurons.

Figure 16A:
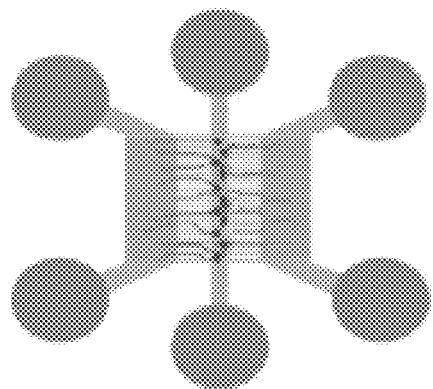

FIG. 16A depicts a chamber used for in vitro studies of hippocampal neurons.

Figure 16B:
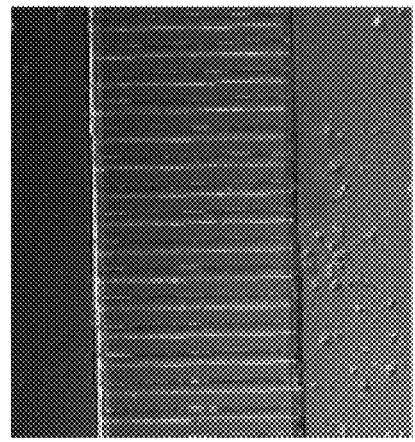

FIG. 16B depicts a photograph of hippocampal neurons after 17 days in culture.

Figure 16C:
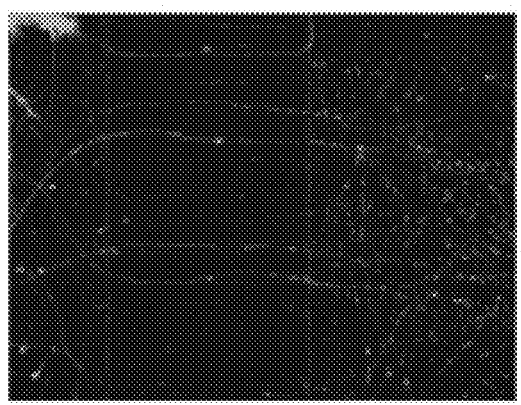

FIG. 16C depicts GFP labelled Fmr1 knockout hippocampal neurons.

Figure 16D:
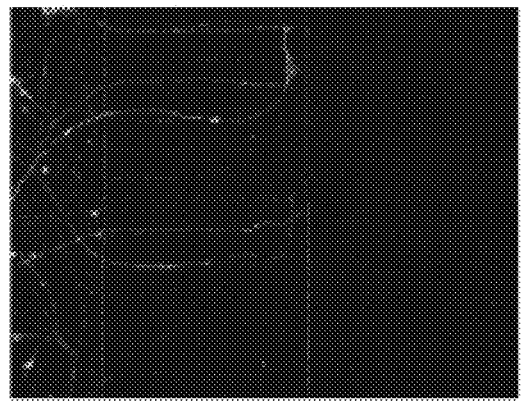

FIG. 16D depicts a photograph of hippocampal neurons from Fmr1 knockout mice treated with cG-2-2AllylP.

Figure 17:
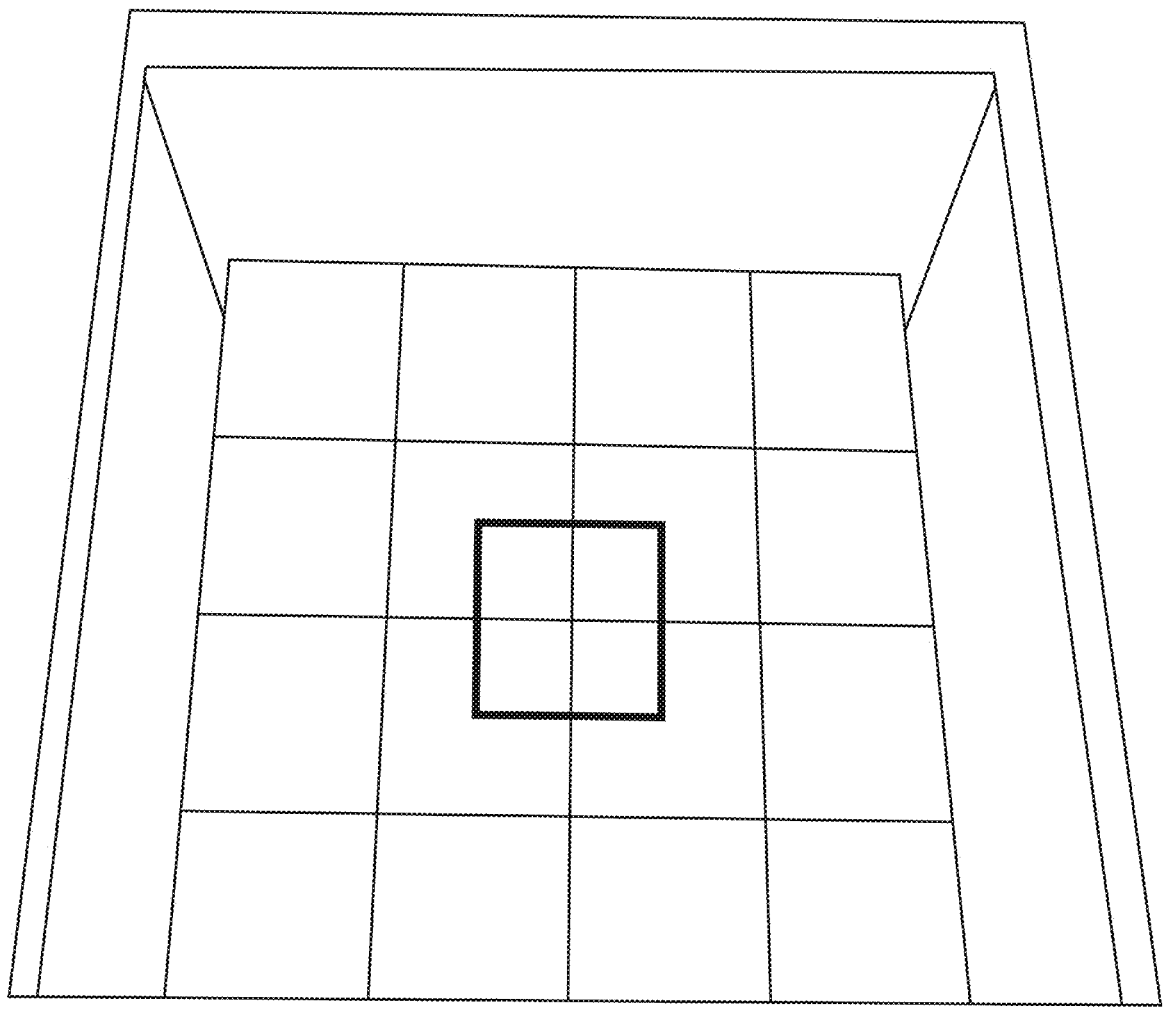

FIG. 17 depicts a photograph of an Open Field Test device used to test effects of cG-2-AllylP of this invention.

Figure 18:
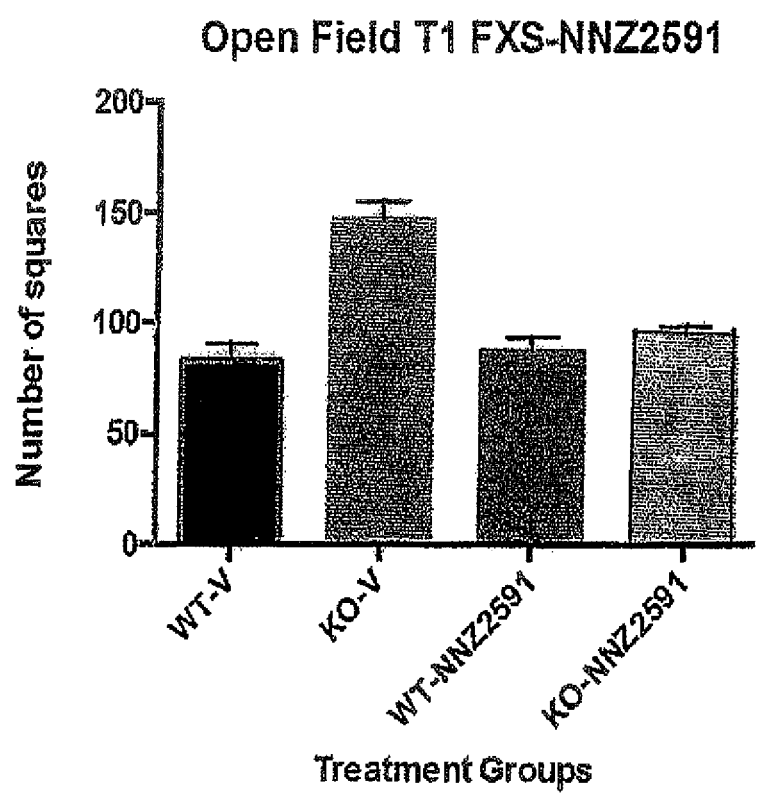

FIG. 18 depicts graph of the time T1 spent in Open Field Test of wild type animals and fmr1 knockout animals treated with either vehicle or cG-2-AllylP.

Figure 19:
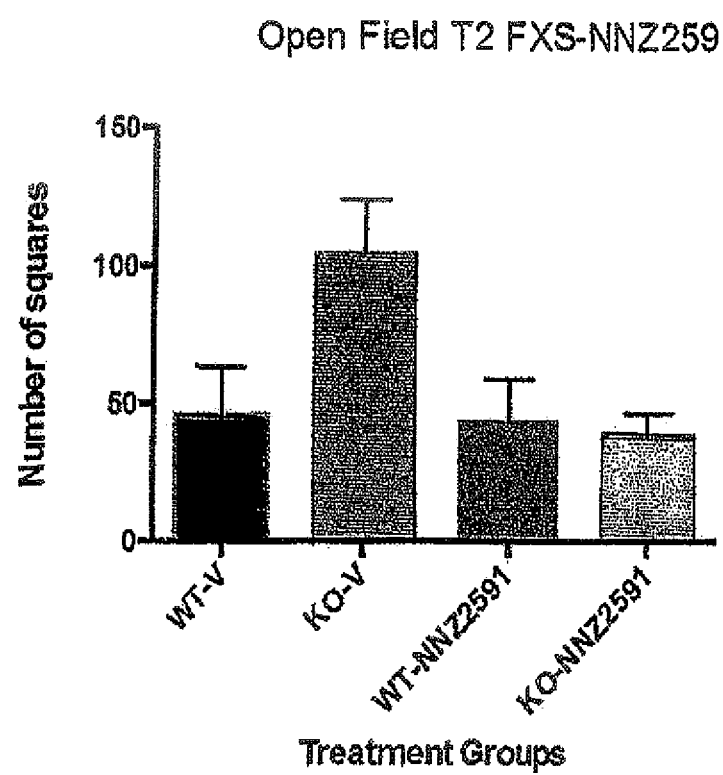

FIG. 19 depicts a graph of results of short-tem memory in an Open Field Test of wild-type animals and fmr1-knockout animals treated with either vehicle or cG-2-AllylP.

Figure 20:
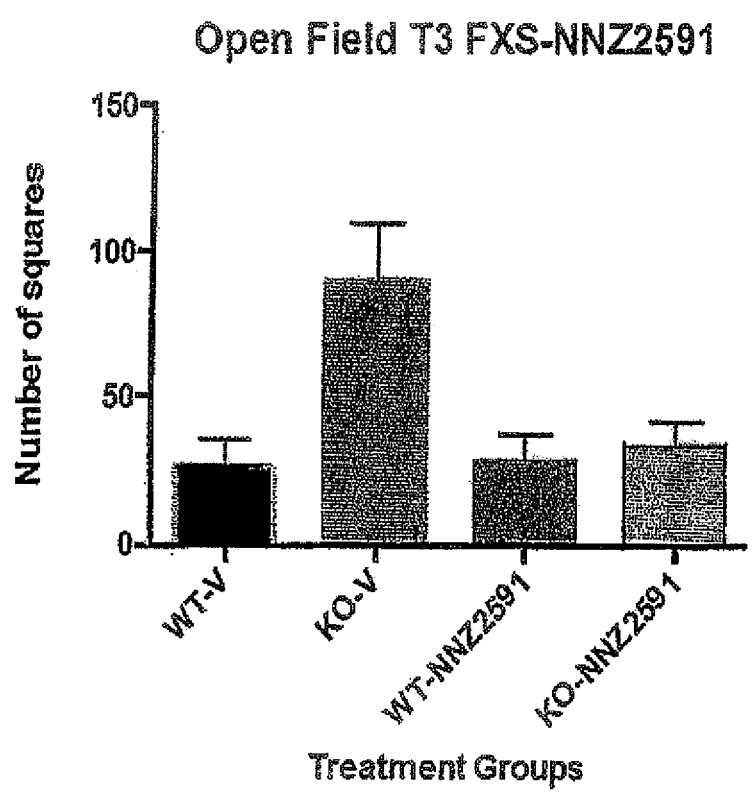

FIG. 20 depicts a graph of results of long-tem memory in an Open Field Test of wild-type animals and fmr1-knockout animals treated with either vehicle or cG-2-AllylP.

Figure 21:
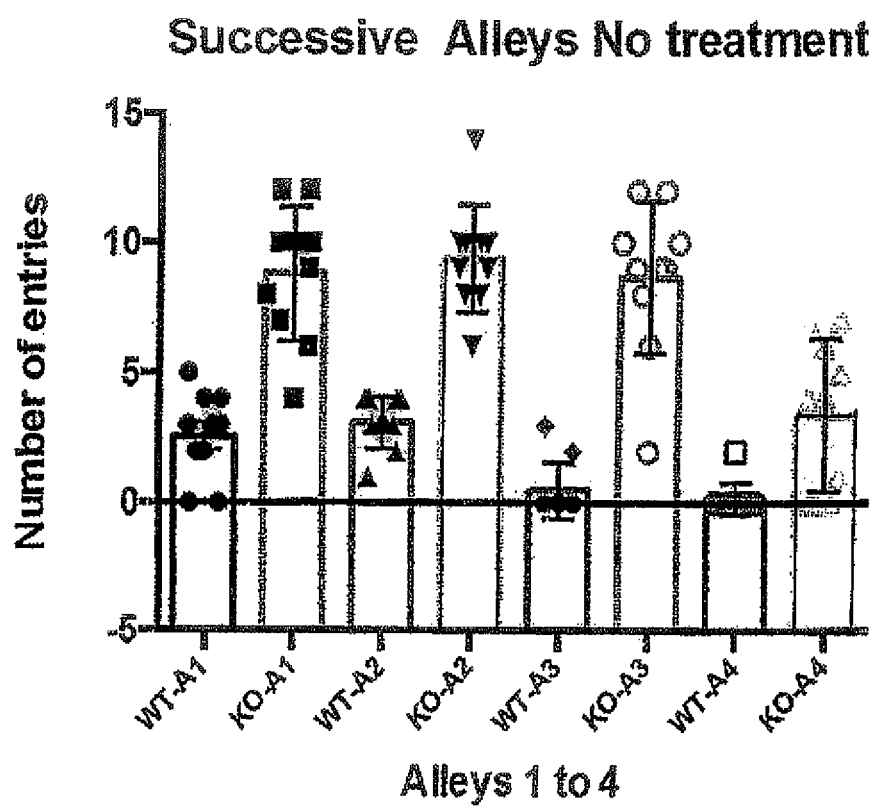

FIG. 21 depicts a graph of results of a Successive Alleys Test in wild-type animals and fmr1-knockout animals treated with vehicle.

Figure 22:
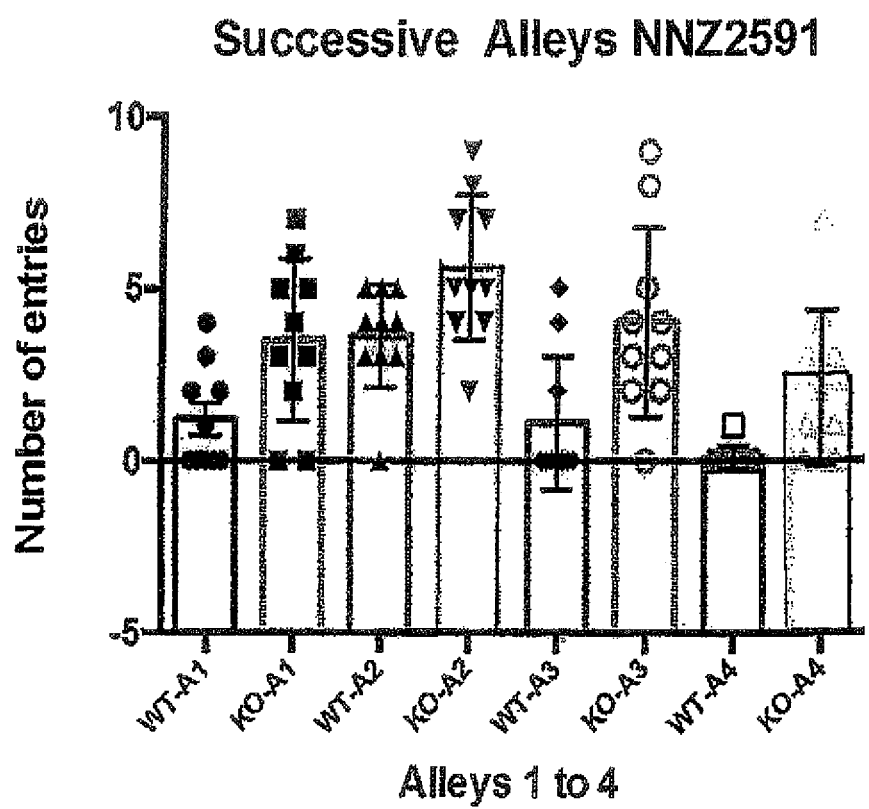

FIG. 22 depicts a graph of results of a Successive Alleys Test in wild-type animals and fmr1-knockout animals treated with cG-2-AllylP.

Figure 23:
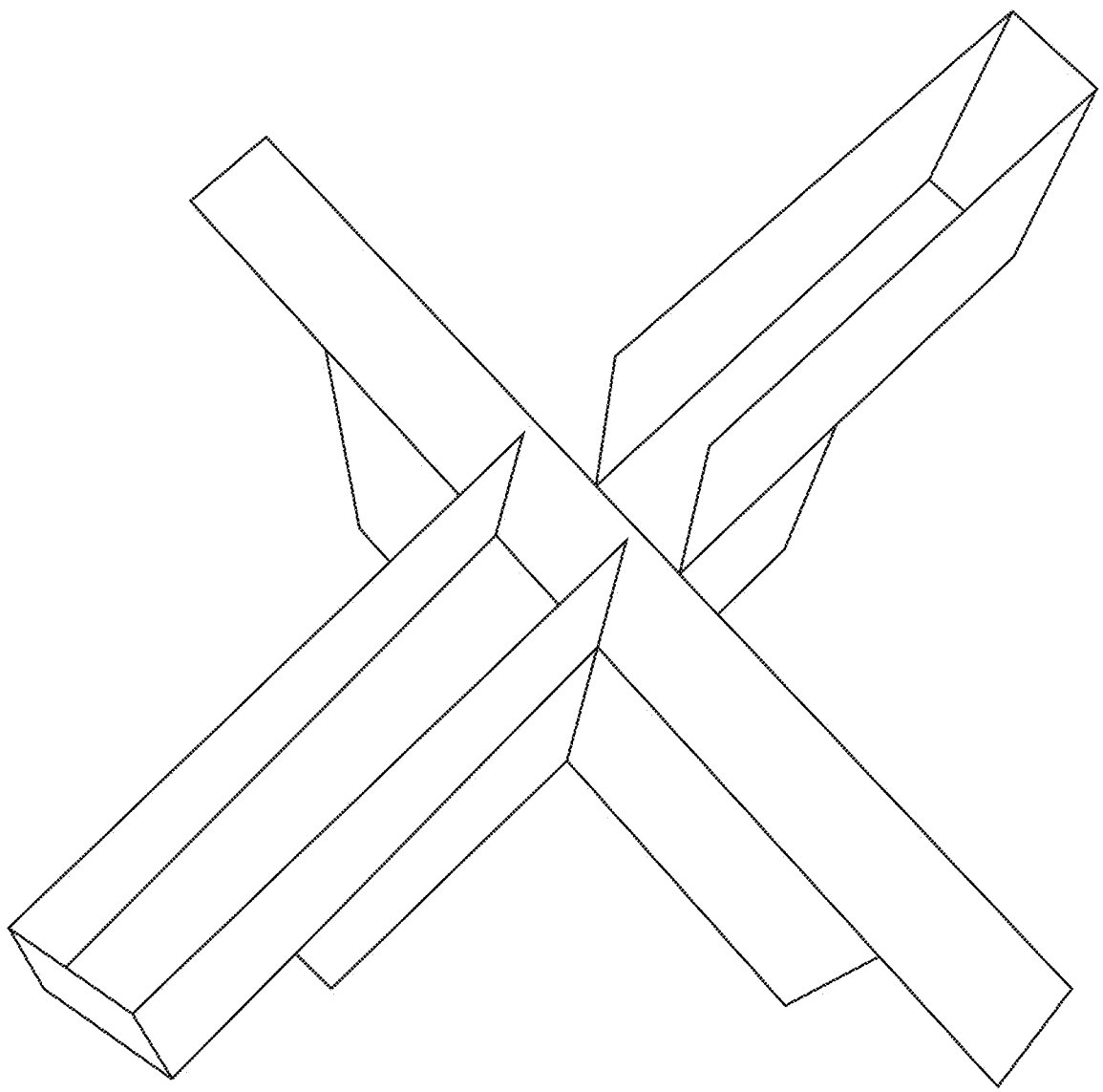

FIG. 23 depicts a photograph of an Elevated Plus Maze used in studies of effects of cG-2-AllylP of this invention in wild-type mice and fmr1-knockout mice.

Figure 24:
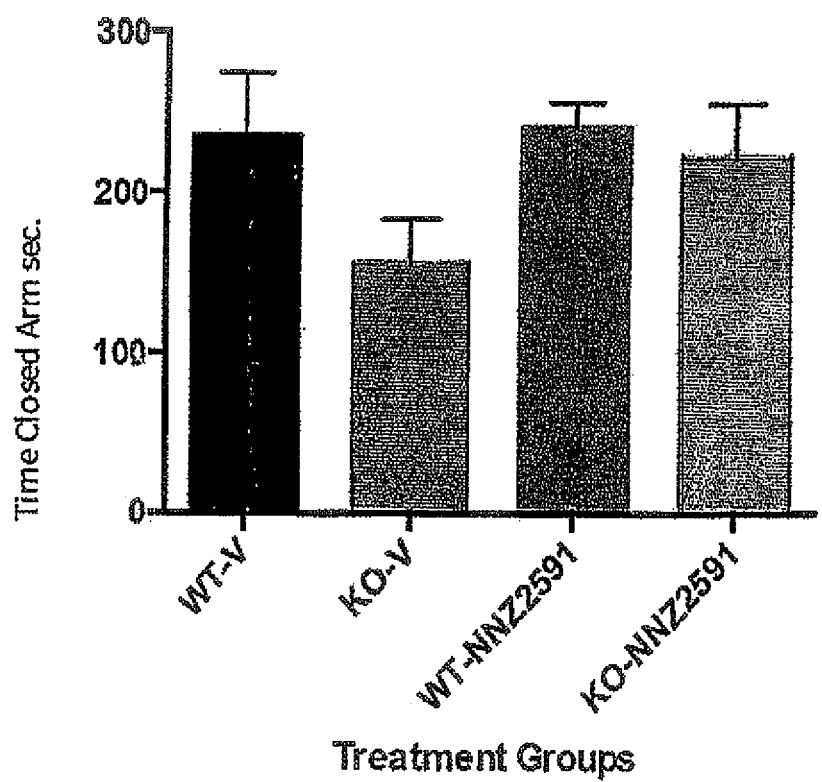

FIG. 24 depicts a graph of results in an Elevated plus Maze Closed Arm Test in wild-type animals and fmr1-knockout animals treated with either vehicle or cG-2-AllylP.

Figure 25:
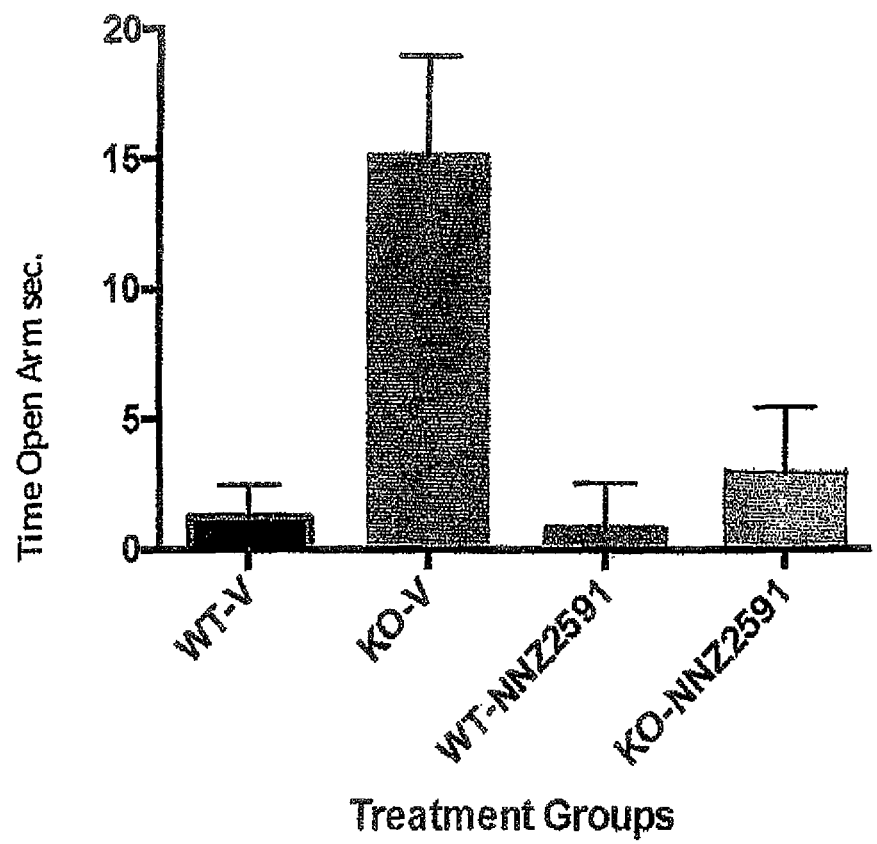

FIG. 25 depicts a graph of results in an Elevated Plus Maze Open Arm Test in wild-type animals and fmr1-knockout animals treated with either vehicle or cG-2-AllylP.

Figure 26:
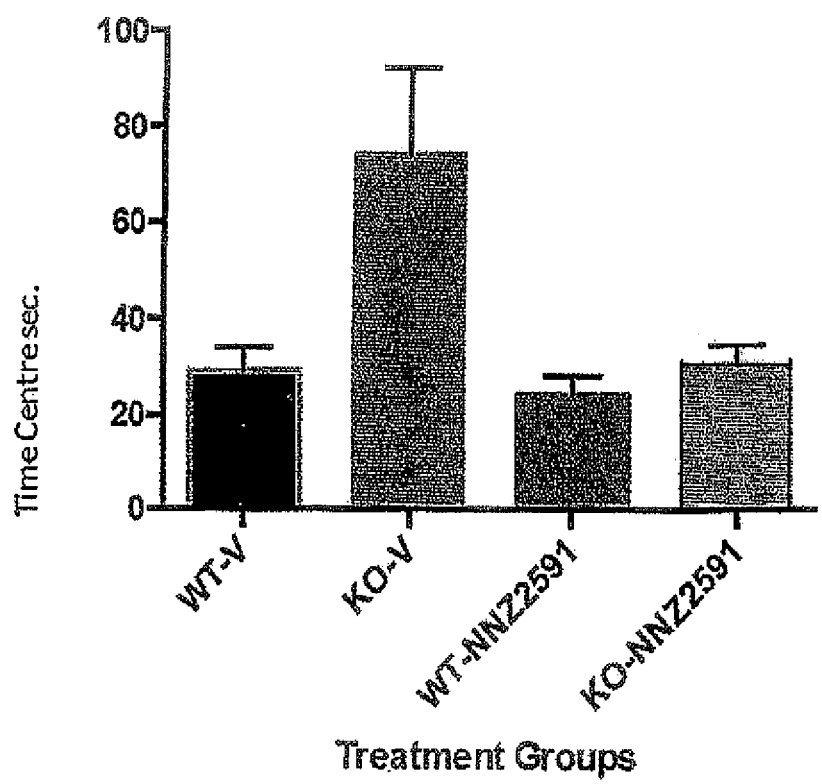

FIG. 26 depicts a graph of results in an Elevated Plus Maze Center Test in wild-type animals and fmr1-knockout animals treated with either vehicle or cG-2-AllylP.

Figure 27:
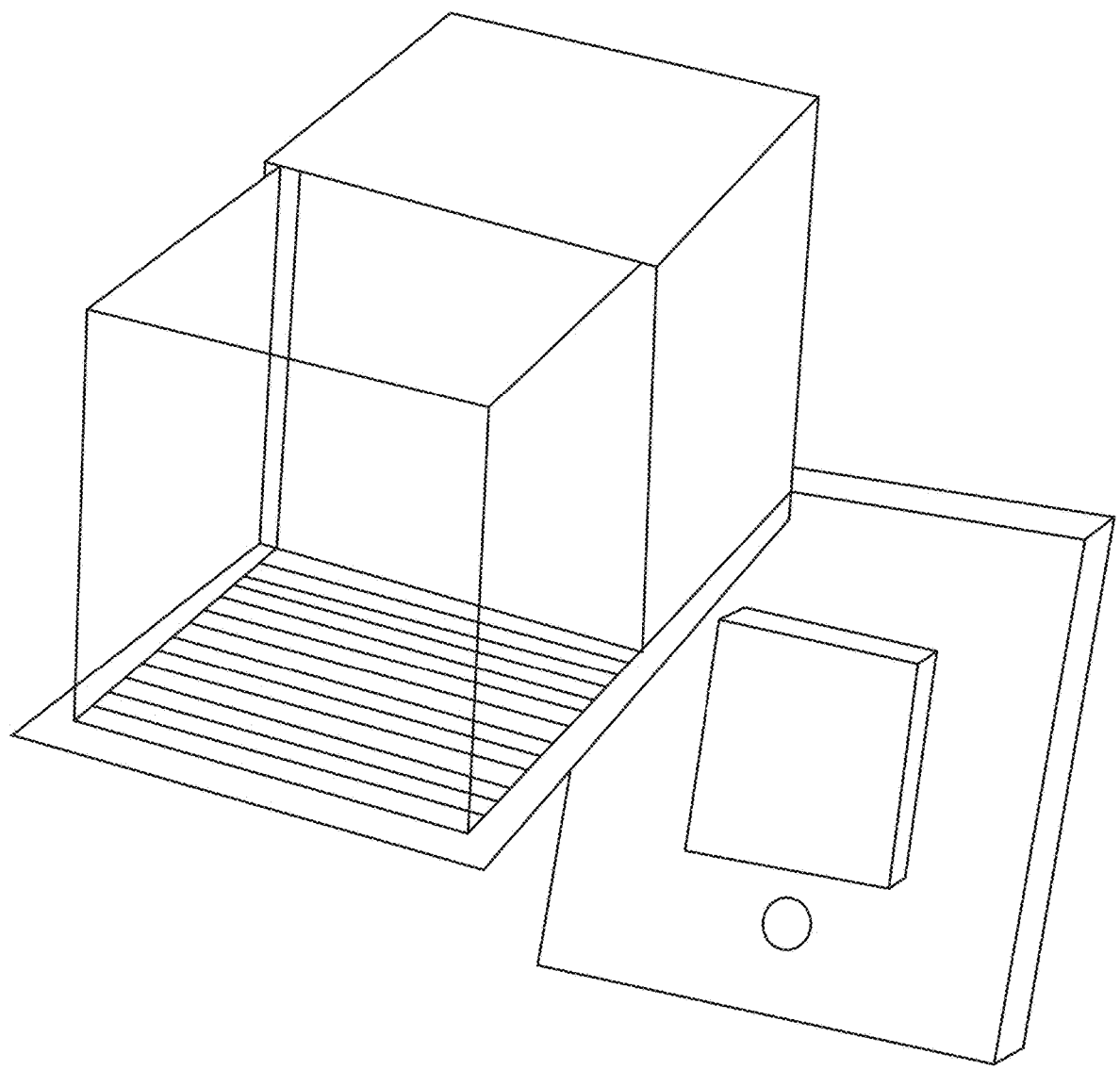

FIG. 27 depicts a photograph of a device used to study effects of cG-2-AllylP on fear conditioning in wild-type and fmr1-knockout mice.

Figure 28:
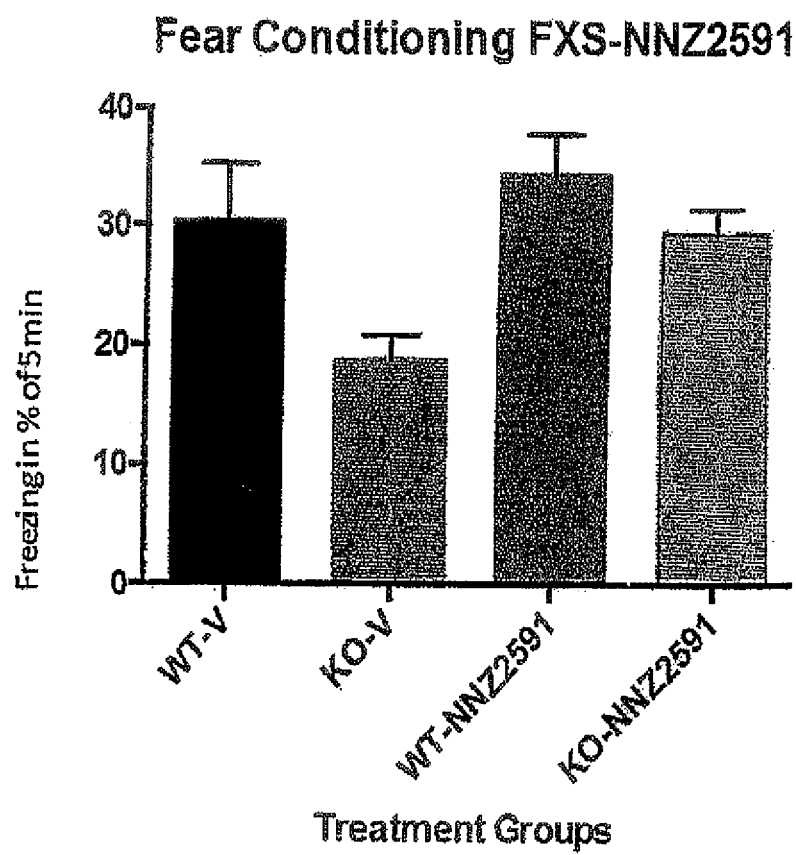

FIG. 28 depicts a graph of results in a Fear Conditioning Test in wild-type animals and fmr1-knockout animals treated with either vehicle or cG-2-AllylP.

FIGS. 29A-E depict photographs of nesting scores used in evaluating effects of cG-2-AllylP on nesting behavior in wild-type mice and fmr1-knockout mice.

Figure 29A:
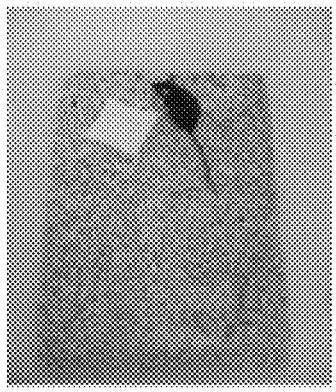
Figure 29B:
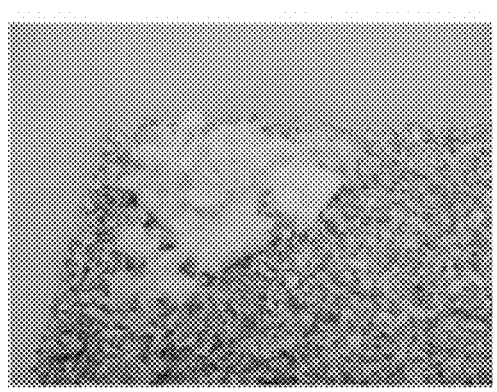

FIG. 29A depicts score of 1.

FIG. 20B depicts a score of 2.

Figure 29C:
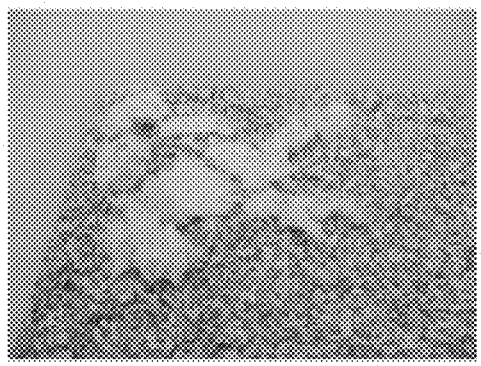

FIG. 29C depicts a score of 3.

FIG. 20D depicts a score of 4.

Figure 29D:
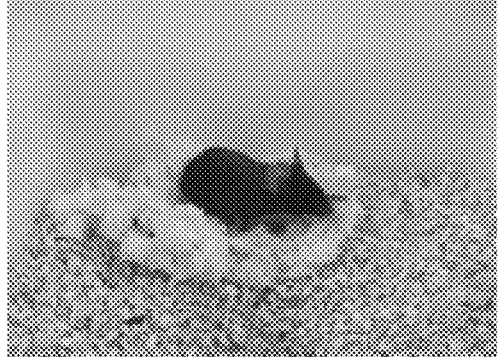
Figure 29E:
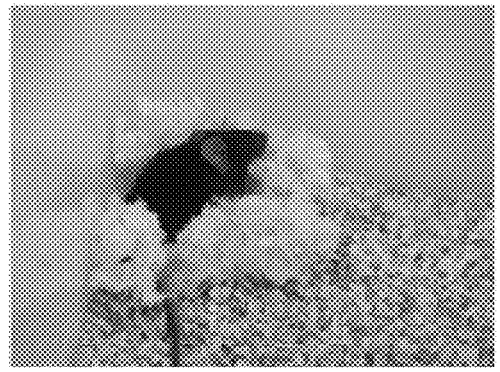

FIG. 29E depicts a score of 5.

Figure 30:
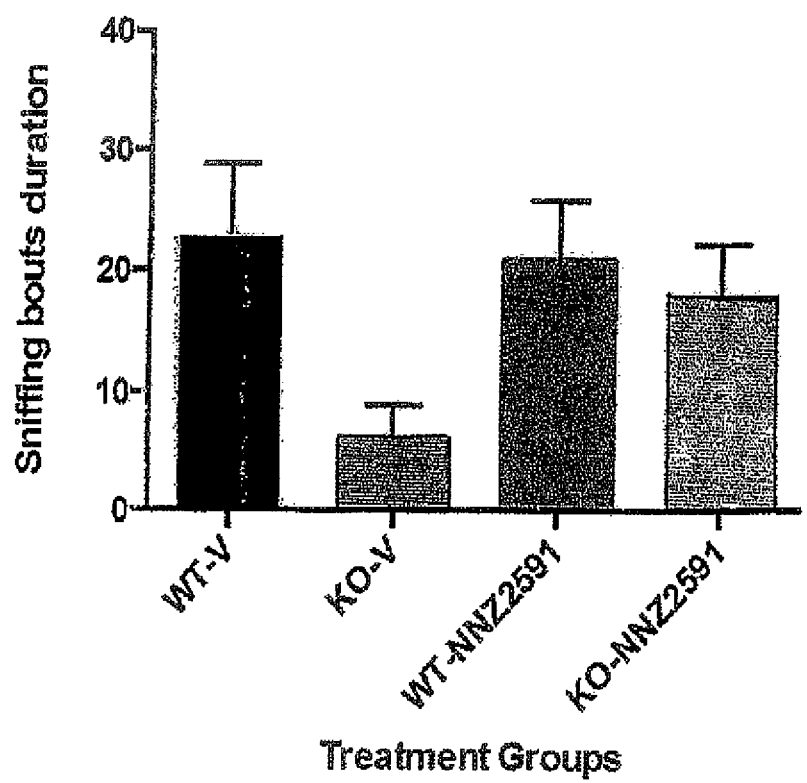

FIG. 30 depicts a graph of results in a Sociability Test in wild-type animals and fmr1-knockout animals treated with either vehicle or cG-2-AllylP.

Figure 31:
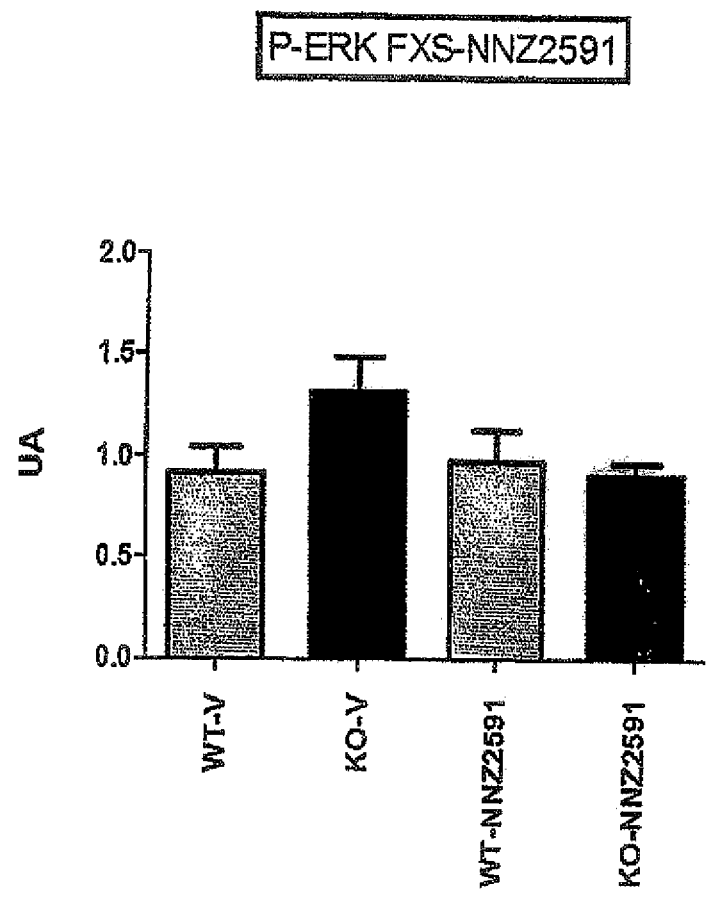

FIG. 31 depicts a graph of results expression levels of pERK in wild-type animals and fmr1-knockout animals treated with either vehicle or cG-2-AllylP.

Figure 32:
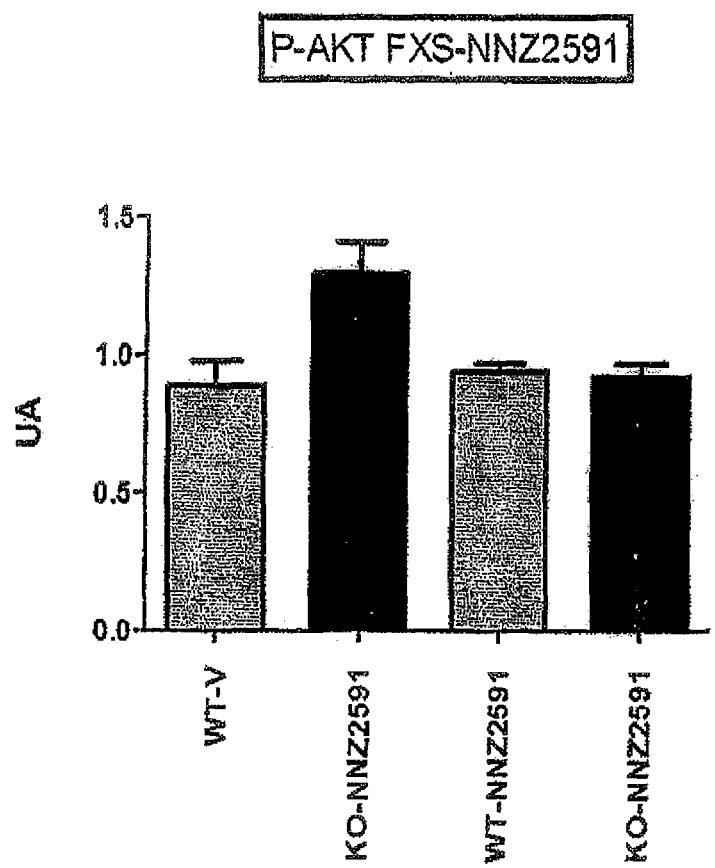

FIG. 32 depicts a graph of results of expression levels of pAKT in wild-type animals and fmr1-knockout animals treated with either vehicle or cG-2-AllylP.

FIGS. 33A, 33B, 33C, 33D, 33E, and 33F depict graphs of results of effects of PBBI and cG-2-AllylP on expression of inflammatory mediators interleukin 1-beta ("IL1-beta") and interleukin 6 ("IL-6").

Figure 33A:
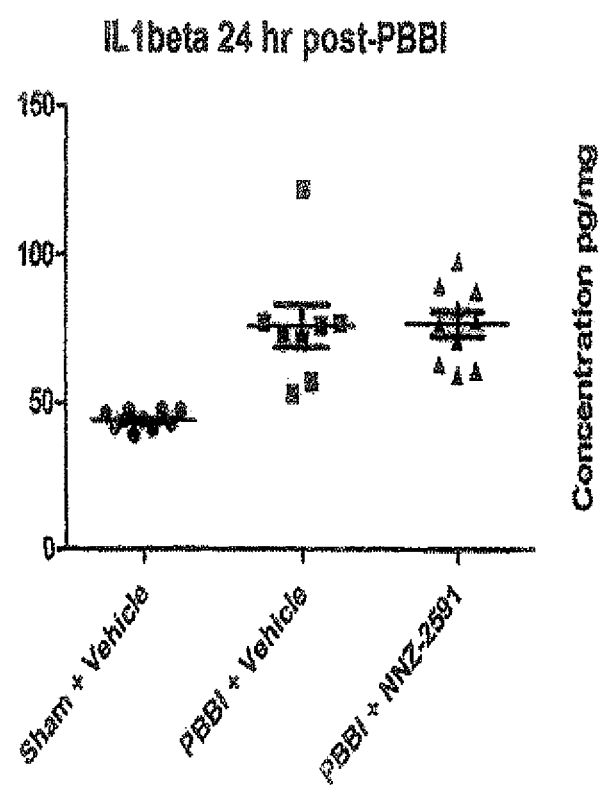
Figure 33B:
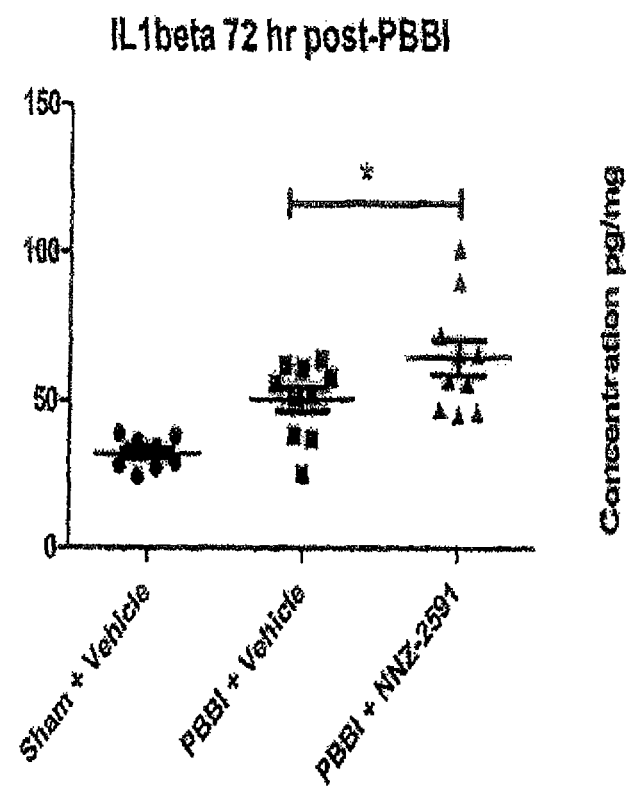
Figure 33C:
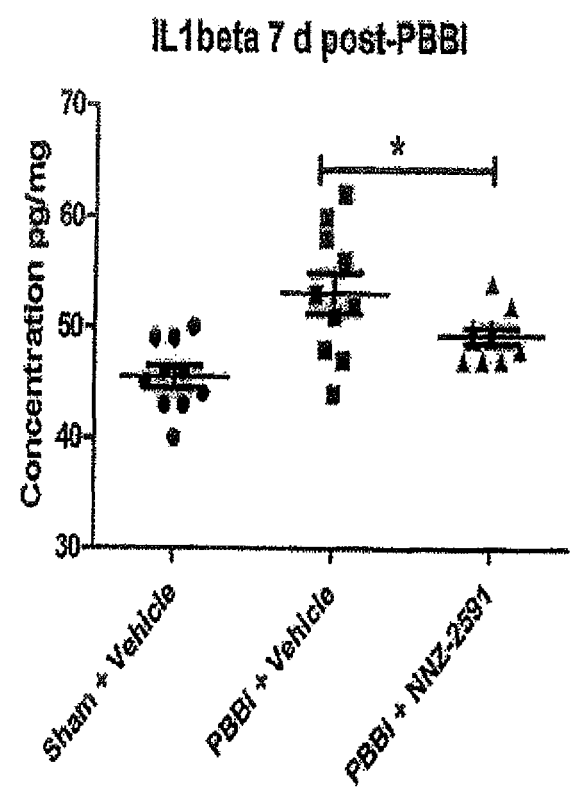

FIGS. 33A, 33B, and 33C depict results for IL1-beta and

Figure 33D:
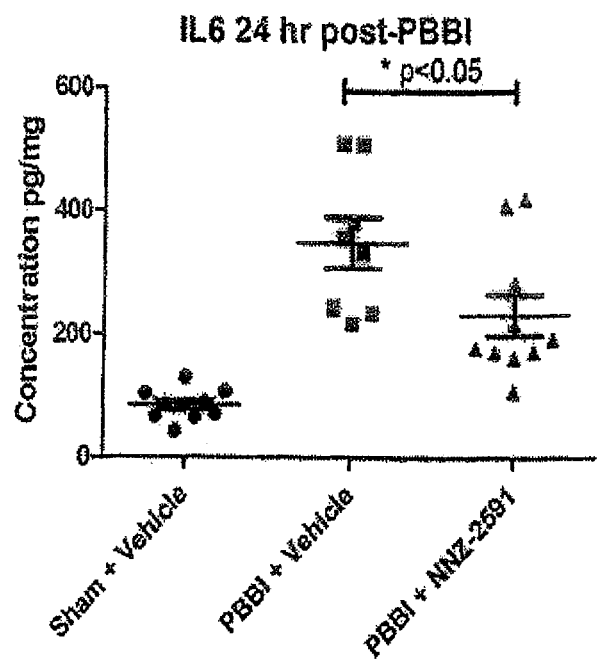
Figure 33E:
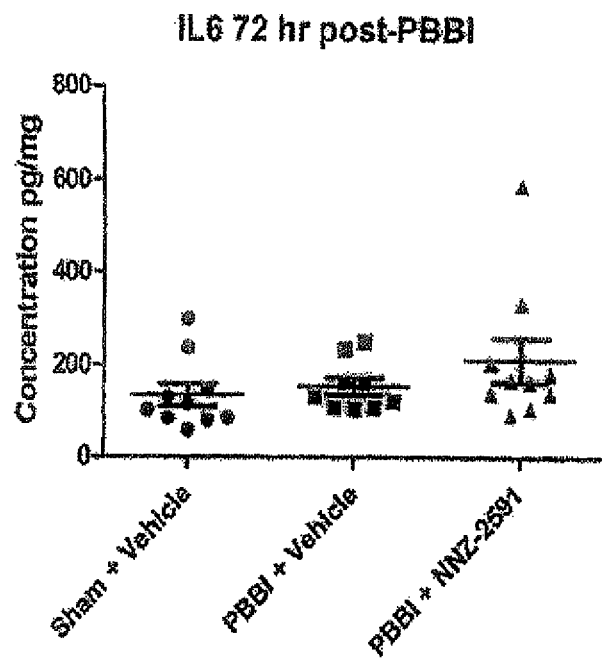
Figure 33F:
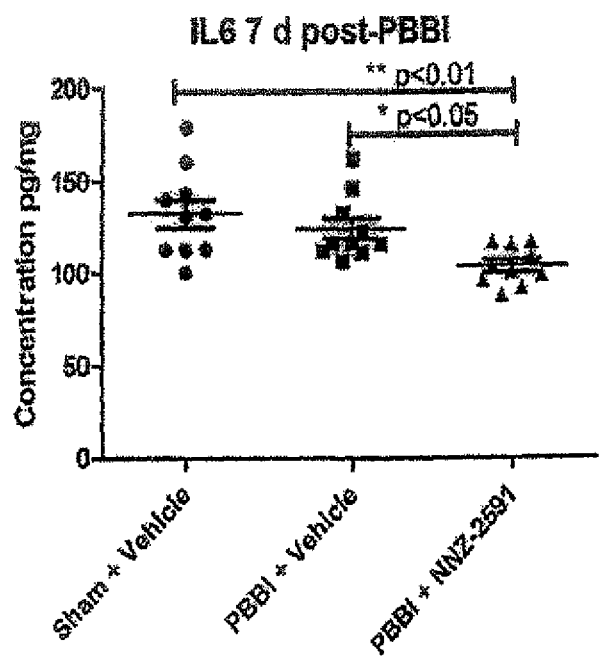

FIGS. 33D, 33E, and 33F depict results for IL-6.

FIG. 34A, 34B, 34C, 34D, 34E, 34F, 34g, and 34 H depict graphs of results of effects of PBBI and cG-2-AllylP on expression of BAX and BCL-2.

Figure 34A:
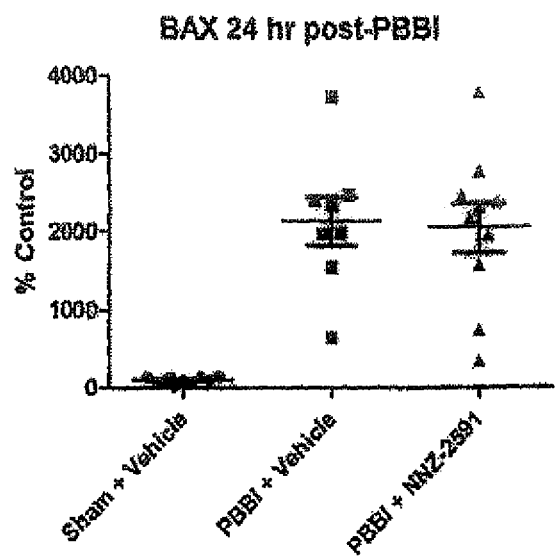
Figure 34B:
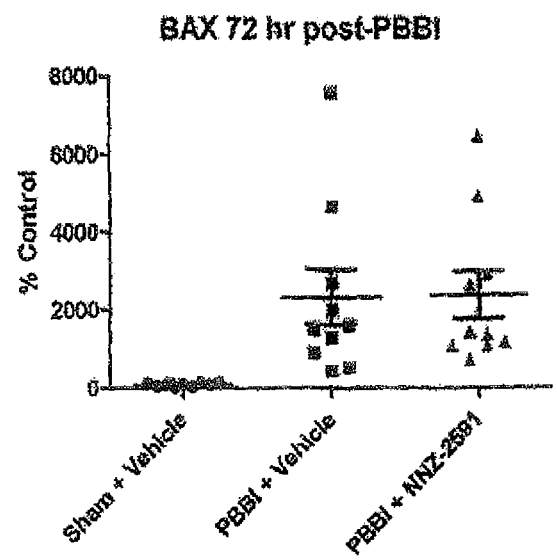
Figure 34C:
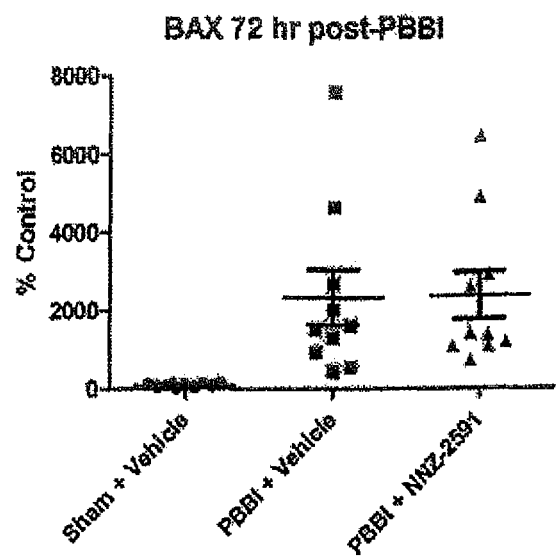
Figure 34D:
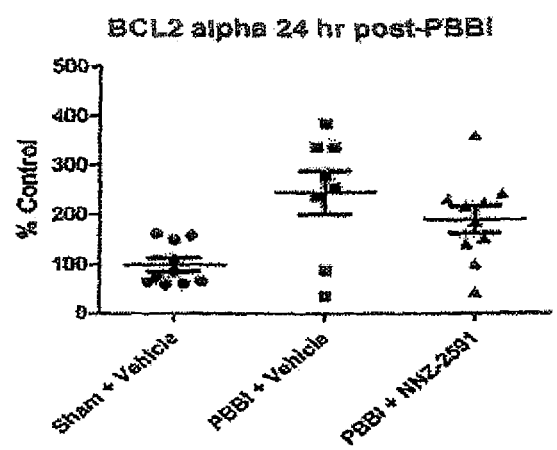
Figure 34E:
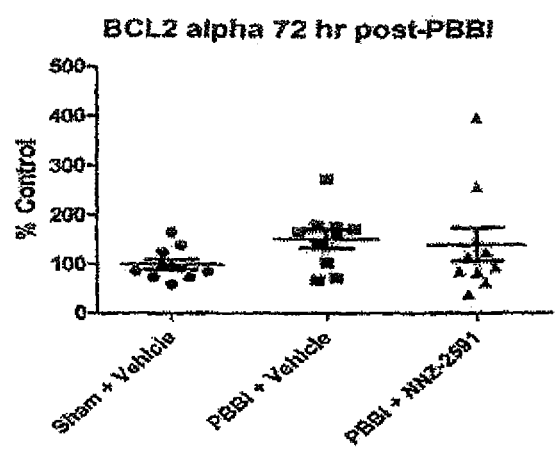
Figure 34F:
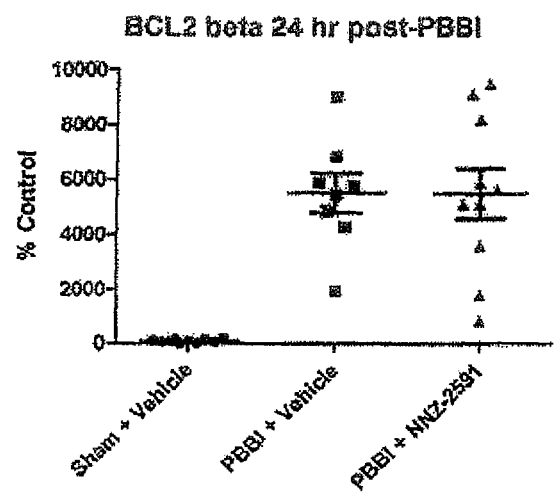
Figure 34G:
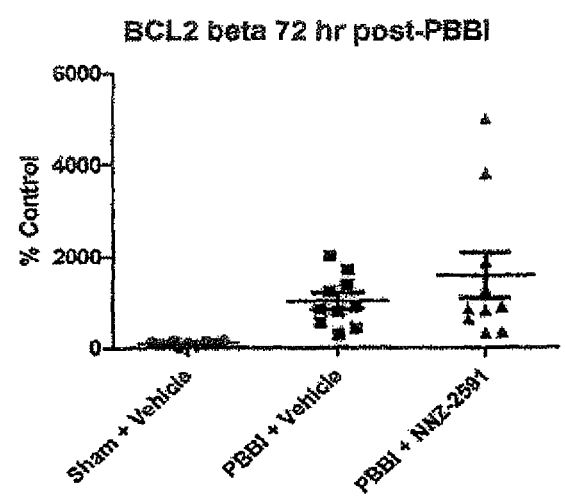
Figure 34H:
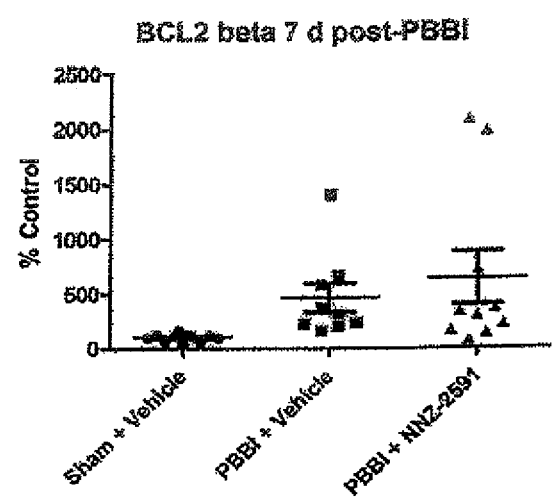

FIGS. 34A, 34B, and 34C depict results for BAX expression.

FIGS. 34D, 34E, 34F, 34G, and 34H depict results for BCL2 expression.

Figure 35A:
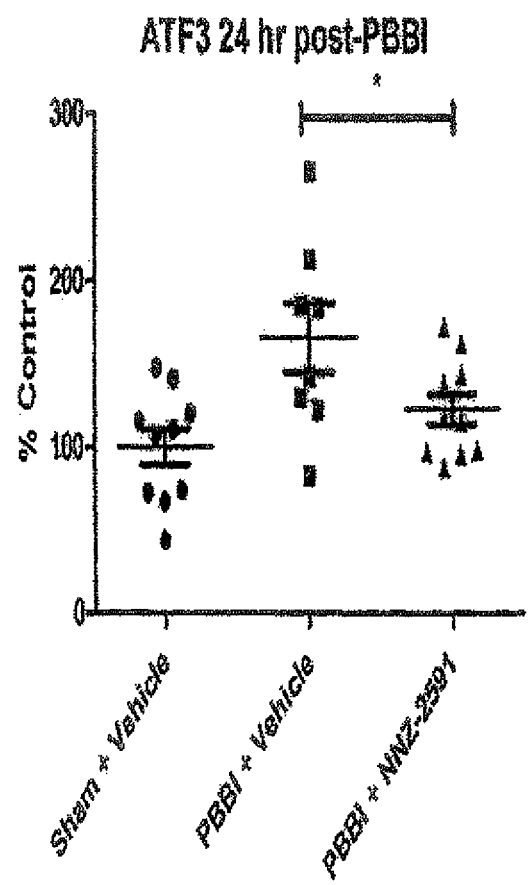
Figure 35B:
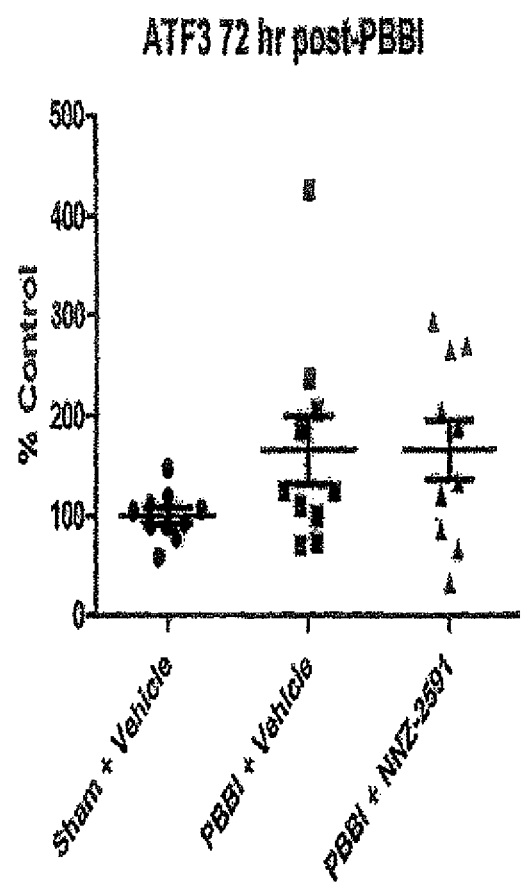
Figure 35C:
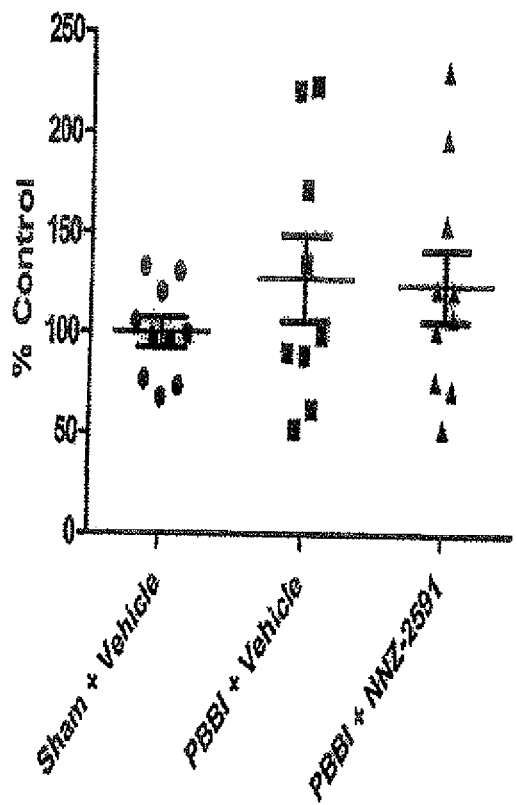

FIGS. 35A, 34B, and 35C depicts graphs of results of effects of PBBI and cG-2-AllylP on expression of ATF3 at three different time points.

Figure 36A:
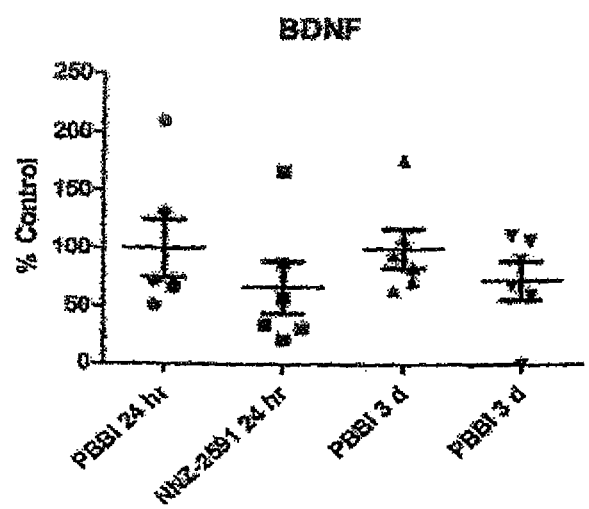
Figure 36B:
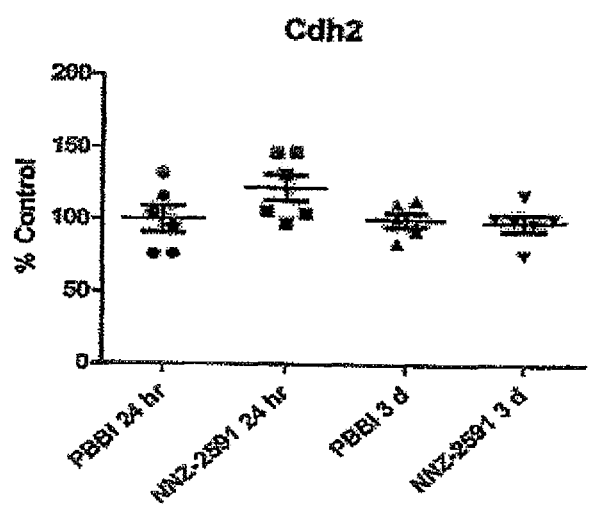
Figure 36C:
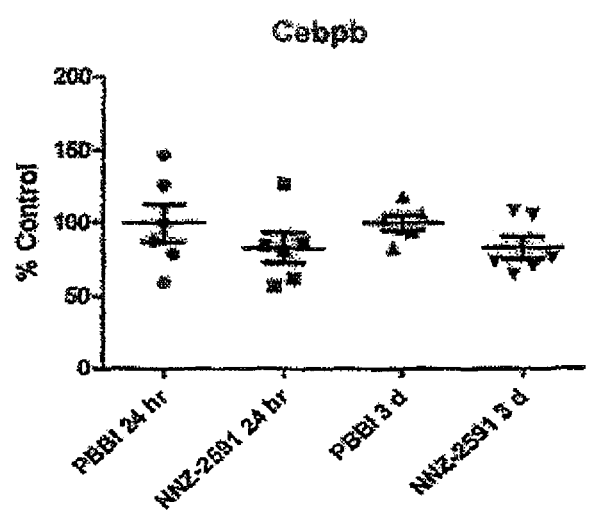
Figure 36D:
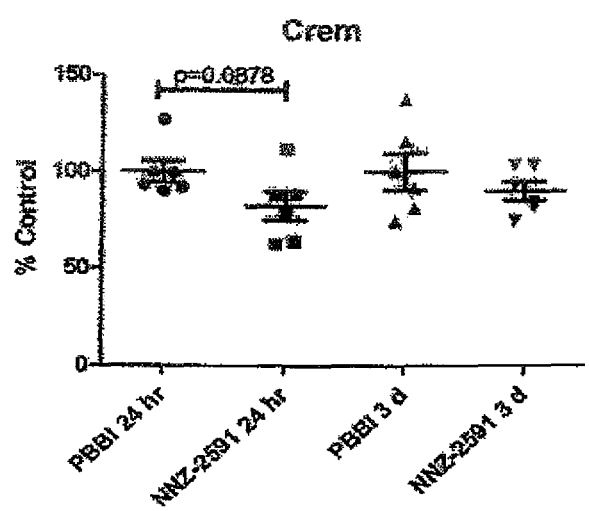
Figure 36E:
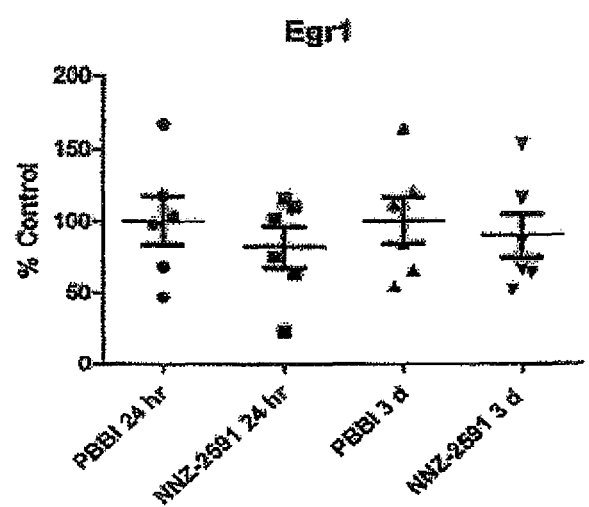
Figure 36F:
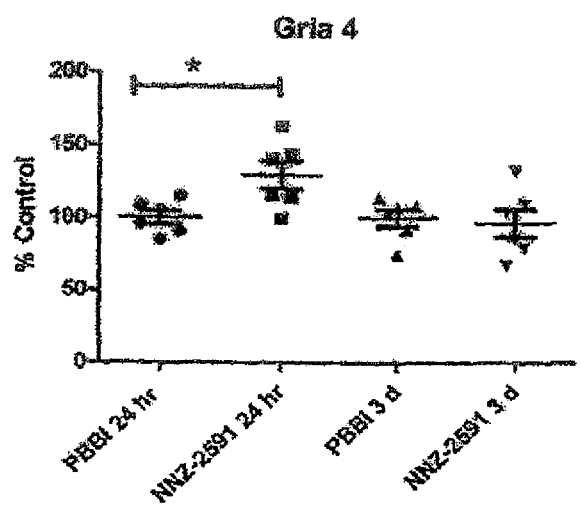
Figure 36G:
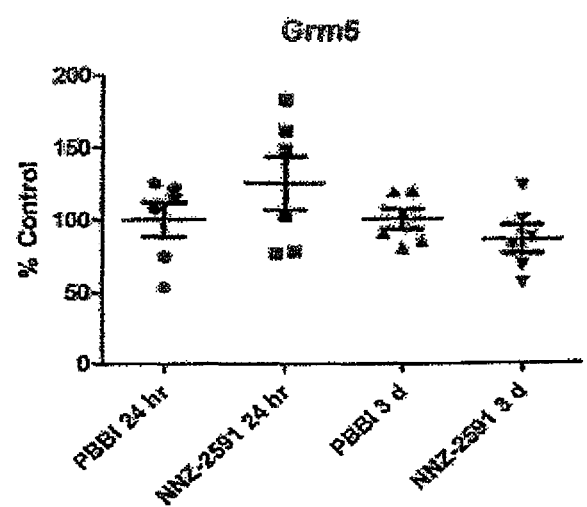
Figure 36H:
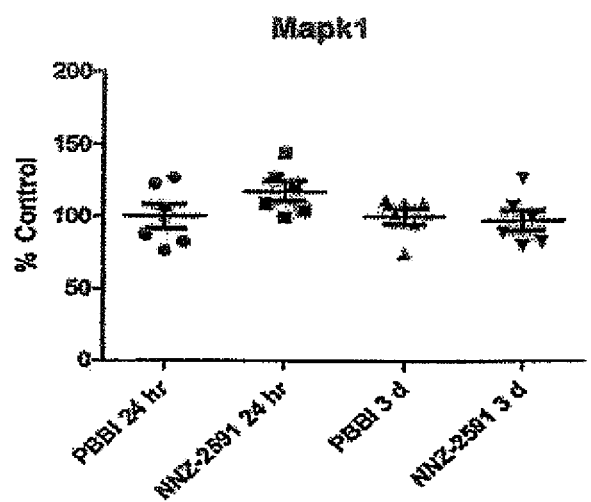
Figure 36I:
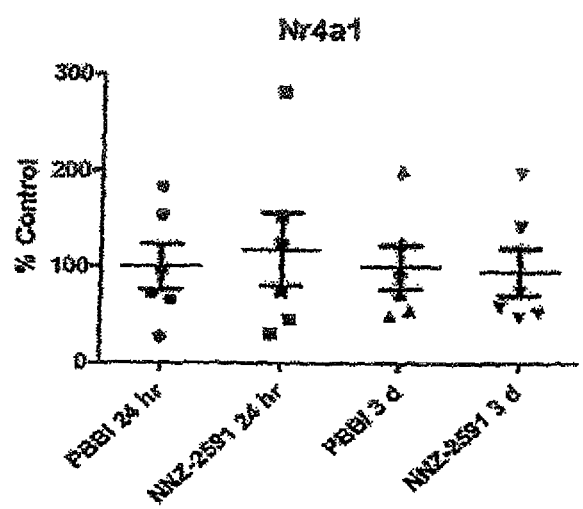
Figure 36J:
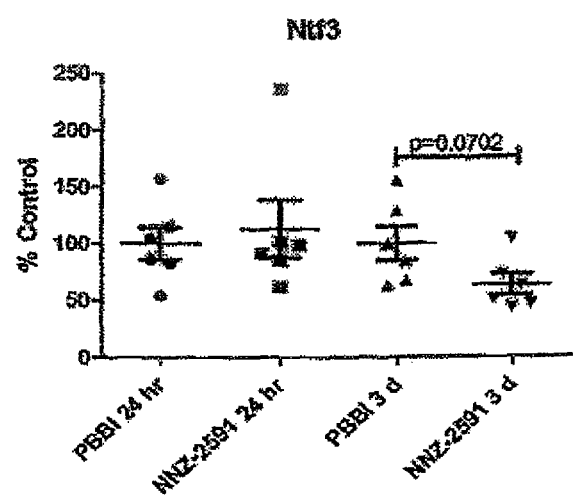
Figure 36K:
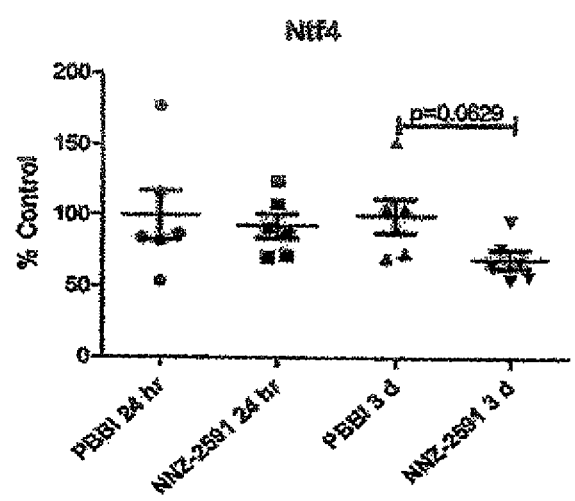
Figure 36L:
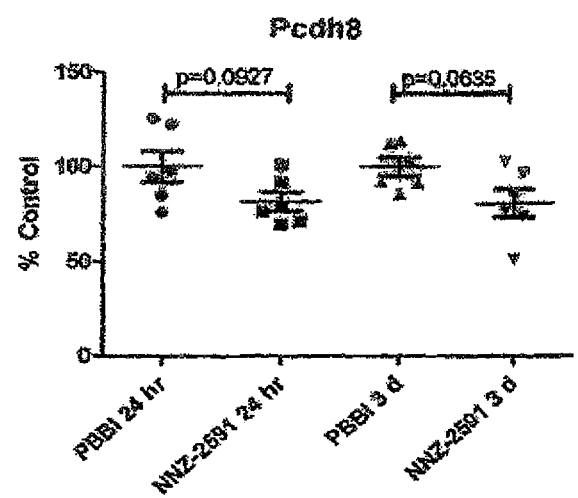
Figure 36M:
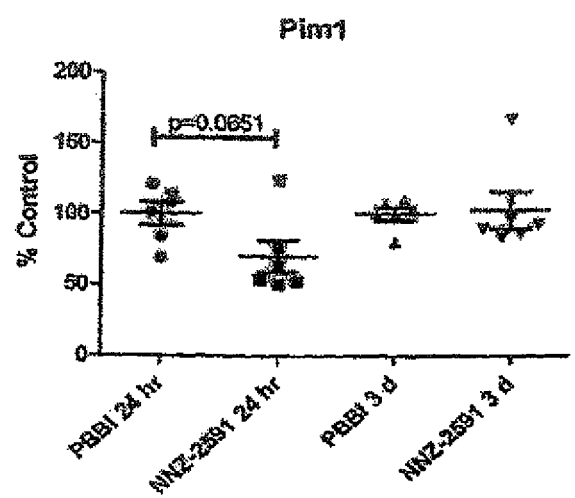
Figure 36N:
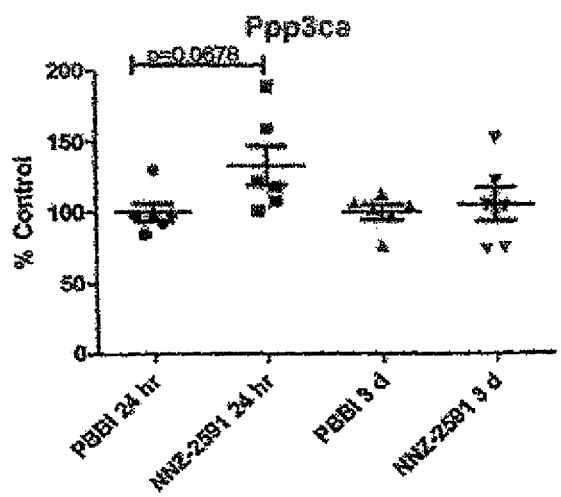
Figure 36O:
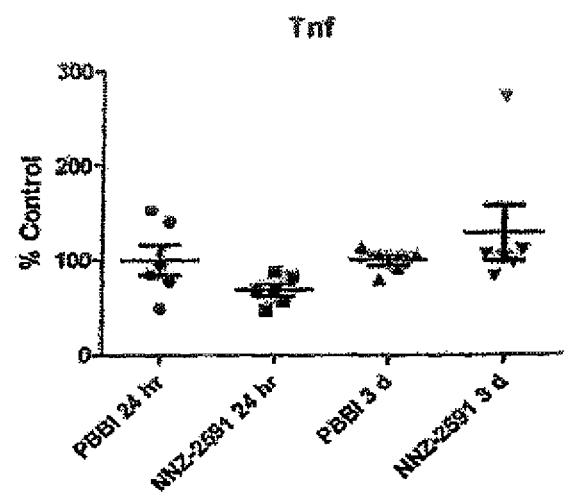

FIG. 36A through 36O depict graphs of results of effects of PBBI and cG-2-AllylP on expression of several genetic markers related to neuroplasticity. FIG. 36A depicts a graph of results of effects of PBBI and cG-2-AllylP on expression of BDNF. FIG. 36B depicts a graph of results of effects of PBBI and cG-2-AllylP on expression of Cdh2. FIG. 36C depicts a graph of results of effects of PBBI and cG-2-AllylP on expression of Cebpb. FIG. 36D depicts a graph of results of effects of PBBI and cG-2-AllylP on expression of Crem. FIG. 36E depicts a graph of results of effects of PBBI and cG-2-AllylP on expression of Egr1. FIG. 36F depicts a graph of results of effects of PBBI and cG-2-AllylP on expression of Gria4. FIG. 36G depicts a graph of results of effects of PBBI and cG-2-AllylP on expression of Grm5. FIG. 36H depicts a graph of results of effects of PBBI and cG-2-AllylP on expression of Mapk1. FIG. 36I depicts a graph of results of effects of PBBI and cG-2-AllylP on expression of Nt4a1. FIG. 36J depicts a graph of results of effects of PBBI and cG-2-AllylP on expression of Ntf3. FIG. 36K depicts a graph of results of effects of PBBI and cG-2-AllylP on expression of Ntf4. FIG. 36L depicts a graph of results of effects of PBBI and cG-2-AllylP on expression of Pcdh8. FIG. 36M depicts a graph of results of effects of PBBI and cG-2-AllylP on expression of Pim1. FIG. 36N depicts a graph of results of effects of PBBI and cG-2-AllylP on expression of Ppp3ca. FIG. 36O depicts a graph of results of effects of PBBI and cG-2-AllylP on expression of Tnf.

DETAILED DESCRIPTION

Definitions

"Alkenyl" refers to an unsaturated branched, straight chain or cyclic hydrocarbon radical having at least one carbon-carbon double bond. The radical may be in either the cis or trans conformation about the double bond(s). Exemplary alkenyl groups include allyl, ethenyl, propenyl, isopropenyl, butenyl, isobutenyl, cyclopentenyl and the like. In some embodiments the alkenyl groups are $(C_2-C_6)$ alkenyl, and in other embodiments, allyl can be particularly useful.

"Alkyl" refers to a saturated branched, straight chain or cyclic hydrocarbon radical. Exemplary alkyl groups include methyl, ethyl, isopropyl, cyclopropyl, tert-butyl, cyclopropylmethyl, hexyl and the like. In some embodiments the alkyl groups are $(C_1-C_6)$ alkyl.

"Alkynyl" refers to an unsaturated branched, straight chain or cyclic hydrocarbon radical having at least one carbon-carbon triple bond. Exemplary alkynyl groups include ethynyl, propynyl, butynyl, isobutynyl and the like. In some embodiments the alkynyl group is $(C_2-C_6)$ alkynyl.

"Aryl" refers to an unsaturated cyclic hydrocarbon radical with a conjugated π electron system. Exemplary aryl groups include phenyl, naphthyl and the like. In some embodiments the aryl group is $(C_3-C_{20})$ aryl.

"Arylalkyl" refers to a straight chain alkyl, alkenyl or alkynyl group wherein one of the hydrogen atoms bound to the terminal carbon is replaced with an aryl group. Exemplary arylalkyl groups include benzyl, naphthylmethyl, benzylidene and the like.

Cognitive impairment can be observed in patients having ASDs, NDDs, Alzheimer's disease, Parkinson's disease, Lewy-bodies dementia and other disorders, as well in aging animals, including humans.

"Comprising," and "Comprises" means including, but not limited to the elements listed.

"Growth factor" refers to an extracellularly active polypeptide that stimulates a cell to grow or proliferate by interacting with a receptor on the cell.

"Heteroalkyl" refers to an alkyl moiety wherein one or more carbon atoms are replaced with another atom such as N, P, O, S etc. Exemplary heteroalkyl groups include pyrrolidine, morpholine, piperidine, piperazine, imidazolidine, pyrazolidine, tetrahydrofuran, ($C_1$-$C_{10}$) substituted amines, ($C_2$-$C_6$) thioethers and the like.

"Heteroaryl" refers to an aryl moiety wherein one or more carbon atoms are replaced with another atom such as N, P, O, S etc. Exemplary heteroaryl groups include carbazole, furan, imidazole, indazole, indole, isoquinoline, purine, pyrazine, pyrazole, pyridazine, pyridine, pyrrole, thiazole, thiophene, triazole and the like.

"Injury" includes any acute or chronic damage of an animal that results in degeneration, dysfunction or death of cells in the nervous system. Such cells include neuronal cells and non-neuronal cells. Injury includes stroke, non-hemorrhagic stroke, traumatic brain injury, perinatal asphyxia associated with fetal distress such as following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycaemia, status epilepticus, episodes of cerebral asphyxia associated with coronary bypass surgery, hypotensive episodes and hypertensive crises, and cerebral trauma. It is to be understood that the above examples are by way of illustration only, and are not intended to be a complete listing of injuries capable of being treated by the compounds and methods of this invention.

A "pharmaceutically acceptable excipient" refers to an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

A "pharmaceutically acceptable salt" refers to a salt that is pharmaceutically acceptable and has the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminium. Suitable organic salts include those formed with organic bases such as the amine bases e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid mono-salt or a di-acid salt; and similarly where there are more than two acidic groups present, some or all of such groups can be present as salts.

A "protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete.

A "stereoisomer" is a molecule having the structure of cyclic G-2-Allyl Proline, but having a chiral center. The term "cyclic G-2-Allyl Proline" includes all stereoisomers.

"Substituted" refers to where one or more of the hydrogen atoms on an alkyl, heteroalkyl, alkenyl, alkynyl, aryl, heteroaryl or arylalkyl radical are independently replaced with another substituent. Substituents include —R', —OR', —SR', —NR'R', —NO$_2$, —CN, —C(O)R', —C(O)OR', —C(O)NR'R', —C(NR')NR'R', —NR'—C(NR')—OR', —NR'—C(NR')—SR', NR'—C(NR'NR'R', trihalomethyl and halogen where each R' is independently —H, alkyl, heteroalkyl, alkenyl, alkynyl, aryl, arylalkyl, heteroaryl or heteroarylalkyl.

"Symptom" or "symptoms" means one or more of cognitive impairment or cognitive dysfunction, one or more signs or symptoms of memory loss, loss of spatial orientation, decreased ability to learn, decreased ability to form short- or long-term memory, decreased episodic memory, decreased ability to consolidate memory, decreased spatial memory, decreased synaptogenesis, decreased synaptic stability, deficits in executive function, deficits in cognitive mapping and scene memory, deficits in declarative and relational memory, decreased rapid acquisition of configural or conjunctive associations, decreased context-specific encoding and retrieval of specific events, decreased episodic and/or episodic-like memory, anxiety, abnormal fear conditioning, abnormal social behaviour, repetitive behaviour, abnormal nocturnal behavior, seizure activity, abnormal locomotion, abnormal expression of Phospho-ERK1/2 and Phospho-Akt, and bradycardia.

A "therapeutically effective amount" means the amount that, when administered to an animal for treating a disease, is sufficient to effect treatment for a disease or an injury. A "therapeutically effective amount" means an amount that decreases adverse symptoms or findings, promotes desirable symptoms or findings, and/or treats an underlying disorder, and/or is curative.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

Implicit hydrogen atoms (such as the hydrogens on the pyrrole ring, etc.) are omitted from the formulae for clarity, but should be understood to be present.

"ATF3" means Activating Transcription Factor 3,

"BAX" means the apoptosis regulator BAX also known as bcl-2-like protein,

"BLC2 alpha" means the B-cell lymphoma-2,

"IL1-beta" means Interleukin 1-beta.

"IL-6" means Interleukin-6.

"BDNF" means Brain Derived Neurotropic factor.

"Cdh2" means Cadherin-2,

"Cebpb" means CCAAT/enhancer-binding protein beta,

"Crem" means cyclic-AMP response element binding,
"Egr1" means Early Growth Response Protein 1,
"Gria 4" means Glutamate Receptor Ionotropic AMPA 4,
"Grm5" means Metabotropic Glutamate Receptor 5,
"Mapk 1" means Mitogen-Activated Protein Kinase 1,
"MeCP2" means Methyl cPg Binding Protein 2,
"Nr4a1" means Nuclear Receptor Subfamily 4 Group A member 1, also known as Nerve Growth Factor IB,
"Ntf3" means Neurotrophin 3,
"Ntf4" means Neurotrophin 4,
"Pcdh8" means Protocadherin-8,
"Plm1" means Pre-mRNA Leakage Protein 1,
"Ppp3ca" means Protein Phosphatase 3, Catalytic Subunit, Alpha.
"Tnf" means Tumor Necrosis Factor.

Autism Spectrum Disorders

Autism spectrum disorders (ASDs) are a collection of linked developmental disorders, characterized by abnormalities in social interaction and communication, restricted interests and repetitive behaviours. In addition to classical Autism or Autistic Disorder, the fifth edition of the American Psychiatric Association's (APA) *Diagnostic and Statistical Manual of Mental Disorders* (DSM-3) recognises Asperger syndrome. Childhood Disintegrative Disorder and Pervasive Developmental Disorder Not Otherwise Specified (PDD-NOS) as ASDs.

Neurodevelopmental Disorders (NDDs) include Fragile X Syndrome (FXS), Angelman Syndrome, Tuberous Sclerosis Complex, Phelan McDermid Syndrome, Rett Syndrome, CDKL5 mutations (which also are associated with Rett Syndrome and X-Linked Infantile Spasm Disorder) and others. Many but not all NDDs are caused by genetic mutations and, as such, are sometimes referred to as monogenic disorders. Some patients with NDDs exhibit behaviors and symptoms of autism.

Clinical Tools for Evaluating ASDs and NDDs

ASDs and NDDs can be assessed using one or more clinical tests, for example. The Rett Syndrome Natural History/Clinical Severity Scale, Aberrant Behavior Checklist Community Edition (ABC), Aberrant Behavior Checklist (Stereotypy), Vinelands, Clinical Global Impression of Severity (CGI-S), the Caregiver Strain Questionnaire (CSQ), Children's Yale-Brown OC Scale (CYBOCS-PDD), Child Autism Rating Scale, Interview of Repetitive Behaviors, Nisonger Child Behavior Rating Scale, Pervasive Developmental Disorder Behav Inventory, Stereotyped Behav Scale, Repetitive Behavior Scale, Rossago Scale, Repetitive Behavior Questionnaire, and Stereotyped Behavior Scale, or one or more physiological test selected from the group consisting of electroencephalogram (EEG) spike frequency, overall power in frequency bands of an EEG, hand movement, QTc and heart rate variability (HRV), and respiratory irregularities compared to control animals not suffering from said disorder. Reliability and relevance of some of these tools as shown in Table 1 below.

As used in this section, the term "Appropriate" means a tool that measures a clinically relevant outcome with good to excellent reliability and validity with information available on all relevant categories. The term "Appropriate with Conditions" means a tool that measures a "clinically relevant outcome for which only certain subscales are relevant," or may be "only relevant for younger age range." The terms "Promising" and Potentially Appropriate" mean a tool that measures "a clinically relevant outcome but is emerging, or has inconsistent reliability and validity (e.g., good to excellent reliability/validity but data is not available in all categories, but a least 2, adequate in all categories."

TABLE 1

Clinical Tools Considered "Appropriate" or "Appropriate with Conditions" for Restricted and Repetitive Behaviors in ASDs and NDDs

| Measure | Type | Reliable and Valid | Sensitive to Change | Condition |
|---|---|---|---|---|
| CYBOCS-PDD | Clinician (interview) | Yes | Yes | Resistance item Not relevant |
| ABC Stereotypy | informant | Yes | Yes | Only 7 items |
| Repetitive Behav Scale | informant | Yesw (at least one study) | Not shown | ? Subscales vs. total score |
| Stereotyped Behav Scale | informant | Yes (adults) | Not shown | Fits for lower functioning |
| Repetitive Behav Questionnaire | informant | Yes | Not shown | Atyical scoring |

Anxiety can be assessed using one or more measures including, Anxiety, Depression and Mood Scale (ADAMS), Child and Adolescent Symptom Inventory (CASI), Child Behavior Checklist (CBCL), Multidimensional Anxiety Scale for Children (MASC), Pediatric Autism Rating Scale (PARS), Revised Child Anxiety and Depression Scale (RCAD), Screen for Child Anxiety Related Disorders (SCARED). Nisonger Child Behavior Rating Form, and Anxiety Diagnostic Interview Scale (ADIS). Reliability and relevance of some of these tools is presented below in Table 2.

TABLE 2

Clinical Tools Considered "Appropriate with Conditions" for Evaluating Anxiety

| Measure | Type | Reliaable & Valid | Sensitivity to Change | Condition |
|---|---|---|---|---|
| CASI-Anxiety | informant | Yes | Yes (pilot data in ASD) | Incomplete coverage |
| Multidimensional Anxiety Scale for Children (MASC) | Informant & Self-report | Yes | Yes (limited Use in ASD) | ↑ reliance on language |
| Pedi. Anxiety Rating Scale (PARS) | Clinician (interview) | Yes | Yes (limited Use in ASD) | ↑↑ reliance on language |
| Anxiety Diagnostic Interview Scale | Clinician (interview) | Yes | Yes (limited Use in ASD) | high-functioning individuals |

Potentially appropriate clinical tools for evaluating anxiety in ASDs and NDDs are shown below in Table 3.

TABLE 3

"Potentially Appropriate" Clinical Tools for Evaluating Anxiety in ASDs and NDDs

| Measure | Type | Reliable & Valid | Sensitive To Change | Comment |
|---|---|---|---|---|
| SCARED | Informant & self-report | Yes | Yes (limited use in ASD) | ↑ reliance on language |
| ADAMS | informant | Yes | Not shonw | Mood & anxiety Data in adults |
| RCADS | Informant & self-report | Yes | Not shown | Mood & anxiety |

Social communication can be assessed using clinical tools, for example, ABAS-II Domain scores, Aberrant Behavior Checklist (ABC)—Lethargy/Social Withdrawal, ADI-R, Autism Diagnostic Observation Scale-Generic (ADOS-G)—new severity scores, Autism Impact Measure, Autism Spectrum Rating Scales, Autism Treatment Evaluation Checklist (ATEC), Ball Toss Game, Behavior Assessment Scale (BAS), Behavior Assessment System for Children 2nd Edition BASC-2 (subscales relevant to social), Behavior Rating Inventory of Executive Function, California Verbal Learning Task-Children's Version (VLT-C) and Modified VLT-C (MVLT-C), Caregiver-Child Interaction, Jahromi 2009, CGI, Childhood Autism Rating Scale (CARS), Children's Social Behavior Questionnaire, Clinical Evaluation of Language Fundamentals (CELF-3 and 4)—Pragmatics Profile, Communication and Symbolic Behavior Scales (CSBS), Comprehension of Affective Speech Task, General Trust Scale, Gilliam Autism Rating Scale (GARS), Joint Attention Measure from the ESCS (JAMES), Let's Face It!, Observational Assessment of Spontaneous Expressive Language (OSEL), Parent Questionnaire, Nagaraj et al. 2006, Parent's Rating Questionnaire, Chan et al, 2009, Pervasive Developmental Disorder Behavior Inventory (PDD-BI) (Short version available: PDD-B 1-Screening Version), Reading the Mind in Films-Adult, Reading the Mind in Films-Child, Reading the Mind in the Eyes Task-Revised (RMET-R)-Adult, Reading the Mind in the Eyes Task-Revised (RMET-R)-Child, Reading the Mind in Voice-Adult, Social Communication Questionnaire (SCQ), Social Responsiveness Scale, Social Skills Improvement System (SSiS), Theory of Mind Test, and VABS-Socialization and Communication.

Of the tools used to assess social communication, the following are considered to be "Appropriate with Conditions:" Aberrant Behavior Checklist (ABC): Lethargy/Social Withdrawal subscale, BASC-2: social skills, withdrawal, functional subscale, CSBS, ESCS, JAMES, SSiS, Vineland Adaptive Behavior Scales socialization and communication subscales. Tools considered to be "Potentially Appropriate" include ABAS-II: conceptual and social domains, ADGS severity scores. Autism Spectrum rating Scales: social communication, CSBQ: understanding subscales, and PDD-BI.

Autism

Classical Autism is a highly variable neurodevelopmental disorder. It is typically diagnosed during infancy or early childhood, with overt symptoms often apparent from the age of 6 months, and becoming established by 2-3 years. According to the criteria set out in the DSM-5 diagnosis of Autism requires a triad of symptoms to be present, including (a) impairments in social interaction, (b) impairments in communication and (c) restricted and repetitive interests and behaviours. Other dysfunctions, such as atypical eating, are also common but are not essential for diagnosis. Of these impairments, social interaction impairments are particularly important for diagnosis, and two of the following impairments must be present for a diagnosis of autism:

(i) impairments in the use of multiple nonverbal behaviors (e.g., eye contact) to regulate social interaction;
(ii) failure to develop peer relationships appropriate to developmental level;
(iii) lack of spontaneous seeking to share enjoyment, interests, or achievements;
(iv) lack of social or emotional reciprocity.

Communication impairments in Autism may be manifested in one or more of the following ways: delay in (or total lack of) the development of spoken language; marked impairment in the ability to initiate or sustain a conversation; stereotyped and repetitive use of language; and/or a lack of spontaneous make-believe play. Restricted, repetitive, and stereotyped patterns of behavior is also required for diagnosis, such as preoccupation with one or more interest considered abnormal in intensity, inflexible adherence to routines or rituals, repetitive motor mannerisms and/or persistent focus on parts of objects.

Lastly, for a diagnosis of Autism, it is necessary that the impairment in the functioning of at least one area (i.e. social interaction, language, or imaginative play) should have an onset at less than 3 years of age.

Asperger Syndrome

Asperger Syndrome is similar to Autism and shares certain features. Like Autism, Asperger Syndrome is also characterized by impairment in social interaction, and this is accompanied by restricted and repetitive interests and behavior. Thus, diagnosis of Asperger Syndrome is characterized by the same triad of impairments as Autism. However, it differs from the other ASDs by having no general delay in language or cognitive development and no deficit in interest in the subject's environment. Moreover, Asperger Syndrome is typically less severe in symptomology than classical Autism and Asperger's patients may function with self-sufficiency and lead relatively normal lives.

Childhood Disintegrative Disorder

Childhood disintegrative disorder (CDD), also known as Heller syndrome, is a condition in which children develop normally until age 2-4 years (i.e. later than in Autism and Rett Syndrome), but then demonstrate a severe loss of social, communication and other skills.

Childhood Disintegrative Disorder is very much like Autism, and both involve normal development followed by significant loss of language, social play and motor skills. However, Childhood Disintegrative Disorder typically occurs later than Autism, involves a more dramatic loss of skills, and is far less common.

Diagnosis of CDD is dependent on dramatic loss of previously acquired skills in two or more of the following areas: language, social skills, play, motor skills (such as a dramatic decline in the ability to walk, climb, grasp, etc.), bowel or bladder control (despite previously being toilet-trained). The loss of developmental skills may be abrupt and take place over the course of days to weeks or may be more gradual.

Pervasive Developmental Disorder-Not Otherwise Specified (PDD-NOS)

Pervasive Developmental Disorder-Not Otherwise Specified (PDD-NOS) is an ASD that describes patients exhibiting some, but not all, of the symptoms associated with other well defined ASDs. The key criteria for diagnosis of an ASD include difficulty socializing with others, repetitive behaviors, and heightened sensitivities to certain stimuli. These may all be found in the ASDs described above. However, Autism, Asperger Syndrome, Rett Syndrome and CDD all have other features that enable their specific diagnosis. When specific diagnosis of one of these four disorders cannot be made, but ASD is apparent, a diagnosis of PDD-NOS is made. Such a diagnosis may result from symptoms starting at a later age than is applicable for other conditions in the spectrum.

Rett Syndrome

Rett Syndrome (RTT) is a neurodevelopmental disorder that almost exclusively affects females (1 in 10:000 live births). Until recently, RTT was classified as an autism spectrum disorder (Diagnostic and Statistical Manual of Mental Disorders, Fourth Edition-Revised (DSM-IV-R). Approximately 16,000 patients are currently affected by it in the U.S.A. (*Rett Syndrome Research Trust data*). For a diagnosis of Rett syndrome, the following symptoms are characteristic: impaired development from age 6-18 months; slowing of the rate of head growth starting from between age 3 months and 4 years; severely impaired language; repetitive and stereotypic hand movements; and gait abnormalities, e.g. toe-walking or unsteady stiff-legged walk. There are in addition, a number of supportive criteria that may help diagnosis of Rett syndrome, but are not essential for a diagnosis. These include breathing difficulties, EEG abnormalities, seizures, muscle rigidity and spasticity, scoliosis (curving of the spine), teeth-grinding, small hands and feet in relation to height, growth retardation, decreased body fat and muscle mass, abnormal sleep patterns, irritability or agitation, chewing and/or swallowing difficulties, poor circulation and constipation.

The onset of RTT usually begins between 6-18 months of age with a slowing of development and growth rates. This is followed by a regression phase (typically in children aged 1-4 years of age), pseudo-stationary phase (2-10 years of age) and a subsequent progressive late motor deterioration state. RTT symptoms include sudden deceleration of growth and regression in language and motor skills including purposeful hand movements being replaced by stereotypical movements, autistic features, panic-like attacks, sleep cycle disturbances, tremors, seizures, respiratory dysfunctions (episodic apnea, hyperpnea), apraxia, dystonia, dyskinesia, hypotonia, progressive kyphosis or scoliosis and severe cognitive impairment. Most RTT patients survive into adulthood with severe disabilities and require 24-hour-a-day care.

Between 85% and 95% cases of RTT are reported to be caused by a mutation of the Mecp2 gene (Amir et al. 1999. Nat Genet 23:185-188; Rett Syndrome Research Trust)—a gene encoding methyl-CpG-binding protein 2 (MeCP2). Mecp2 maps to the X-chromosome (location Xq28) and for this reason, mutations to the gene in males are usually lethal. While RTT is a genetic disorder, less than 1% of recorded cases are inherited; almost all mutations of Mecp2 occur de novo, with two thirds caused by mutations at 8 CpG dinucleotides (R106, R133, T158, R168, R255, R270, R294 and R306) located on the third and fourth exons.

MeCP2 is a protein that binds methylated CpG dinucleotides to exert transcriptional silencing of DNA in the CNS. The key effect of a reduction or absence of MeCP2 appears to be an impairment of dendritic spine development and the formation of synapses. MeCP2 expression appears to temporally correlate with brain maturation, explaining why symptoms typically appear around 18 months of age.

Presenting Features Common to ASDs

Taking the ASDs together, it is clear that there are commonalities in presenting symptoms among all 5 forms. These common features are impairments in normal social competences, and repetitive behaviours. In all but Asperger Syndrome there is also a consistent presentation of delayed intellectual development most commonly manifest as a shortfall in language skills. Cognitive loss relative to normal parameters for the age is often quite marked in autism, Rett Syndrome, CDD and PDD-NOS.

Genetic Models of ASDs

To offer validity, animal models of ASDs must demonstrate similar symptoms to the clinical conditions and have a reasonable degree of face validity regarding the etiology of those symptoms. It is known that classical Autism may be caused by many different genetic impairments and no single genetic defect is thought to account for more than a few percent of autism cases. Indeed, recent studies have revealed numerous de novo structural variations of chromosome locations thought to underlie ASD, in addition to rare inherited genetic defects (Marshall et al, 2008; Sebat et al, 2007). Thus, copy number variation (CNV), translocation and inversion of gene sequences at 20 key sites or more, including 1p, 5q, 7q, 15q, 16p, 17p and Xq, have been mapped as ASD loci.

However, despite the polygenetic background underlying ASD and the complexity of the etiology, it is known that certain genetic defects can produce ASD. Some of the best characterized defects arise from chromosomal aberrations of genes that code for a cluster of postsynaptic density proteins, including neuroligin-3 (NLGN3), neuroligin-4 (NLGN4), neurexin-la (NRXN1) and shank3 (Sebat et al, 2007).

NLGN3 and NLGN4 are postsynaptic cell-adhesion molecules present in glutamatergic synapses. They play a role of coordinating presynaptic contact to the postsynaptic site and also interact with the postsynaptic scaffolding protein shank3. Mutations to NLGN3 and NLGN4 have been observed in the ASD population and account for perhaps 1% of all ASD cases (Lintas & Persico, 2008). Jamain and colleagues first reported a missense to NLGN3 and a frameshift to NLGN4 in two unrelated subjects, resulting in Asperger Syndrome and classical Autism, respectively (Jamain et al, 2003). While the incidence of NLGN3 or NLGN4 mutations in the ASD population is certainly low (indeed, no such mutations were observed in a study of 96 ASD patients in a Canadian study; Gauthier et al, 2003), it has been confirmed in preclinical studies that neuroligin mutations can indeed produce of model of autistic symptoms. Thus, introduction to mice of the same R431C missense to NLGN3 that has been reported clinically results in a mutant mouse strain showing reduced social interaction and enhanced inhibitory synaptic transmission (Tabuchi et al, 2007).

The R431C mutant therefore mouse represents a model for ASD based upon NLGN3 mutation. In this case, mutation at the R451 position of NLGN3 results in a 'gain-of-function' mutation.

In contrast, modeling the clinical mutation of NLGN4 in mice is achieved by a 'loss-of-function' mutation of NLGN4 (a classical knockout model). In this model, mutant mice display a social interaction deficit and reduced ultrasonic vocalization (Jamain et al, 2008). Communication deficits are central to clinical ASDs and in the NLGN4 knockout mice a reduction in ultrasonic vocalizations from male mice exposed to wild-type female counterparts supports the face validity of the strain as a model of ASD.

Presynaptic neurexin proteins induce postsynaptic differentiation in apposing dendrites through interactions with postsynaptic neuroligin counterparts. Mutations of the neurexin-la (NRXN1) gene have been reported in numerous studies (Sebat et al, 2007; Marshall et al, 2008; Kim et al, 2008; Yan et al, 2008) and these have been observed in the form of copy-number variants. As with NLGN mutations, when a mutation of the NRXN1 gene is introduced to mice (in the form of gene knockout), a mutant strain with certain ASD-like features is produced (Etherton et al, 2009). These NRXN1 knockout mice show a decrease in hippocampal miniature excitatory postsynaptic current (mEPSC) frequency and a decreased input-output relationship of evoked currents. These electrophysiological effects relate to decreased excitatory transmission in the hippocampus. In addition to decreased excitatory neurotransmission, NRXN1 knockout mice exhibit a decrease in pre-pulse inhibition, though social behaviour appears to be unaffected (Etherton et al, 2009).

Sharing certain features with the neurexin-NLGN trans-synaptic construct, cell adhesion molecule 1 (CADM1) is an immunogolbulin family protein present both pre- and post-synaptically that is also involved in synaptic trans-cell adhesion activity (Biederer et al, 2002). Mutations to the CADM1 gene have been detected in ASD patients and appear to represent a further possible cause of these conditions (Zhiling et al, 2008).

Analysis of CADM1 knockout mice reveals that these animals show increased anxiety-related behavior, impaired in social interaction and impaired social memory and recognition. In addition CADM1 knockout mice demonstrate poorer motor skills (Takayanagi et al, 2010). These dysfunctions are again consistent with ASD symptomology.

22q13 deletion syndrome (also known as Phelan-McDermid Syndrome), is a rare genetic disorder caused by a microdeletion at the q13.3 terminal end of chromosome 22. This microdeletion is rarely uncovered by typical genetic screening and a fluorescence in situ hybridization test is recommended to confirm the diagnosis. Recent work indicates the syndrome is caused by errors in the gene shank3 which codes for a postsynaptic density protein critical for normal neuronal functioning. Interestingly, errors in this gene have also been associated with ASD and 22q13 deletion syndrome can commonly lead to an ASD diagnosis (Durand et al, 2007; Moessner et al, 2007; Sykes et al, 2009). Given the close association of 22q13 deletion syndrome and the consequential diagnosis of ASD, a mutant mouse model of this mutation has been developed.

The shank3 knockout mouse exhibits several deficits that mirror ASD symptoms, including reduced ultrasonic vocalizations (i.e., diminished social communication) as well as impaired social interaction time between mice. In addition, these mice also have impaired hippocampal CA1 excitatory transmission, measured by input-output relationship of evoked currents and impaired long-term potentiation (LTP). LTP is believed to be a physiological process underlying memory formation and consolidation. Thus, the model exhibits a similar phenotype to the NLGN4 knockout, consistent with ASD.

As has been noted, 22q13 deletion syndrome itself is very rare. However, it provides important information that involvement of specific genes may have a definitive role in the etiology of ASDs. In addition to shank3, this disorder reveals a further possible gene defect in ASD. Of the 50 or so cases of 22q13 deletion syndrome described, all but one have a gene deletion that extends beyond shank3 to include a further gene, known as the Islet Brain-2 gene (IB2) (Sebat et al, 2007). The IB2 protein interacts with many other proteins including MAP kinases and amyloid precursor protein, appears to influence protein trafficking in neurites and is enriched at postsynaptic densities (Giza et al, 2010). Mice lacking the protein (IB2-/- knockout mice) exhibit impaired social interaction (reduced social sniffing and interaction time), reduced exploration and cognitive and motoric deficits (Giza et al, 2010). This behavioural phenotype was associated with reduced excitatory transmission in cerebellar cells. As with shank3 knockout, the phenotype of IB2 mutation is therefore also consistent with ASD.

In addition to the animal models of postsynaptic density protein defects described above, other monogenetic syndromes that share various features with ASDs can lead to autism offer another avenue for drug targeting of ASD.

Recently, Fragile X Syndrome has been assigned to another family of disorders, called Neurodevelopmental Disorders (NDDs). The descriptions herein make no distinction based on the official classification of the disorder. If, in the future, one or other ASD or NDD is reclassified, this descriptions and disclosures herein will apply to those new classifications, regardless of their name(s).

Fragile X Syndrome

Fragile X Syndrome (FXS) is caused by the expansion of a single trinucleotide gene sequence (CGG) on the X-chromosome that results in failure to express the protein coded by the fmr1 gene. FMR1 (fragile X mental retardation 1) is a protein required for normal neural development. Fragile X Syndrome can cause a child to have autism (Hagerman et al, 2010); in 2-6% of all children diagnosed with Autism the cause is FMR1 gene mutation. Moreover, approximately 30% of children with FXS have some degree of Autism and a further 30% are diagnosed with PDD-NOS (Hagerman et al, 2010). Indeed, Fragile X Syndrome is the most common known single gene cause of Autism. FMR1 knockout mice have been developed as a model of FXS, and therefore, as a further model a mutation of the fmr1 gene has been shown to result in abnormal dendritic spine development and pruning (Comery et al, 1997), along with an associated dysregulation of dendritic scaffold proteins (including shank 1) and glutamate receptor subunits in postsynaptic densities (Schütt et al, 2009). These effects of dendrite morphology result in impaired LTP in the cortex and amygdala (Zhao et al, 2005) and hippocampus (Lauterbom et al, 2007), as well as impaired cognition (Kreuger et al, 2011) and an enhancement in social anxiety (Spencer et al, 2005).

Rett Syndrome

In contrast to the ASD of autism, Asperger, CDD and PDD-NOS, Rett Syndrome appears to have an almost monogenetic basis and may be modelled in mice with good face validity. Rett Syndrome is thought be caused, in up to 96% of cases, by a defect in the Mecp2 gene (Zoghbi, 2005). As a result, MeCP2 knockout mutant mice provide an animal model with all the hallmarks of clinical Rett Syndrome, with a phenotype showing some overlap with the NLGN4, shank3 and IB2 knockout models of ASD. Thus, MeCP2 knockout mice display a clear impairment in LTP in the hippocampus along with a corresponding decrease in social and spatial memory (Moretti et al, 2006) and impaired object recognition (Schaevitz et al, 2010).

Thus, ASDs in human beings share many features of cognitive or developmental disorders in animals, including rodents. Therefore, studies of therapies of ASDs in rodents such as mice and rats are reasonably predictable of results obtained in human beings.

Compounds of the Invention

Certain embodiments of this invention include novel derivatives of cyclic Prolyl-Glutamate ("cPG") having structures as described below.

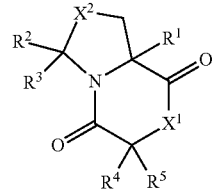

Formula 1

In certain embodiments, compounds of Formula 1 include substituents where:

$X^1$ is selected from the group consisting of NR', O and S;

$X^2$ is selected from the group consisting of $CH_2$, NR', O and S;

$R^1$, $R^2$, $R^3$, $R^4$ and $R^5$ are independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^4$ and $R^5$ taken together are —$CH_2$—$(CH_2)_n$—$CH_2$— where n is an integer from 0-6;

or $R^2$ and $R^3$ taken together are —$CH_2$—$(CH_1)_n$—$CH_2$— where n is an integer from 0-6;

with the proviso that when $R^1$=methyl and $R^2$=$R^3$=$R^4$=H then $R^5 \neq$ benzyl and;

when $R^1$=H, at least one of $R^2$ and $R^3 \neq$ H.

In further embodiments, compounds of Formula 1 include substituents where:

$R^1$=methyl, $R^2$=$R^3$=$R^4$=$R^5$=H, $X^1$=NH, $X^2$=$CH_2$;
$R^1$=allyl, $R^2$=$R^3$=$R^4$=$R^5$=H, $X^1$=NH, $X^2$=$CH_2$;
$R^1$=$R^4$=$R^5$=H, $R^2$=$R^3$=methyl, $X^1$=NH, $X^2$=$CH_2$;
$R^1$=$R^4$=$R^3$=H, $R^2$=$R^3$=methyl, $X^1$=NH, $X^2$=$CH_2$.

In other embodiments of the invention, compounds of Formula 1 include substituents where:

$R^4$ and $R^5$ taken together are —$CH_2$—$(CH_2)_n$—$CH_2$— and:

$R^1$=methyl, $R^2$=$R^3$=H, n=0, $X^1$=NH, $X^2$=$CH_2$;
$R^1$-methyl, $R^2$=$R^3$=H, n=2, $X^1$=NH, $X^2$=$CH_2$;
$R^1$=allyl, $R^2$=$R^3$=H, n=0, $X^1$=NH, $X^2$=$CH_2$;
$R^1$=allyl, $R^2$=$R^3$=H, n=2, $X^1$=NH, $X^2$=$CH_2$.
$R^1$-methyl, $R^2$=$R^3$=H, n=3, $X^1$=NH, $X^2$=$CH_2$;
$R^1$=allyl, $R^2$=$R^3$=H, n=3, $X^1$=NH, $X^2$=$CH_2$.

In still other embodiments of the invention, compounds of Formula 1 include substituents where $R^1$=methyl or allyl, $R^2$=$R^3$=$R^4$=H and $R^5$ is selected from the group consisting of the side chains of the amino acids: alanine, arginine, asparagine, aspartic acid, cysteine, glutamic acid, glutamine, histidine, isoleucine, leucine, lysine, methionine, proline, serine, threonine, tryptophan, tyrosine, valine, norvaline, norleucine, citruline, ornithine, homocysteine, homoserine, alloisoleucine, isovaline, sarcosine and the like.

In yet further embodiments of the invention, compounds of Formula 1 include substituents where:

$R^1$=methyl, $R^2$=$R^3$=methyl, $R^4$=$R^5$=H, $X^1$=NH and $X^2$S;
$R^1$-allyl, $R^2$=$R^3$=methyl, $R^4$=$R^5$H, $X^1$=NH, and $X^2$=S.

Those with skill in the art will appreciate that the above structural representations can contain chiral centres, the number of which will depend on the different substituents. The chirality may be either R or S at each centre. The structural drawings can represent only one of the passible tautomeric, conformational diastereomeric or enantiomeric forms, and it should be understood that the invention encompasses any tautomeric, conformational isomeric diastereomeric or enantiomeric form, which exhibits biological or pharmacological activity as described herein.

Pharmacology and Utility

Cyclic Glycyl-2-Allyl Proline (cG-2-AllylP) is described in U.S. Utility application Ser. No. 11/399,974 filed Apr. 7, 2006, entitled "Cyclic G-2Allyl Proline in Treatment of Parkinson's Disease," now U.S. Pat. No. 7,776,876, issued Aug. 17, 2010, U.S. Utility application Ser. No. 10/570,393, filed Mar. 2, 2006 entitled "Neuroprotective Bicyclic Compounds and Methods for Their Use," now U.S. Pat. No. 8,067,425, PCT International Patent Application No: PCT/US2004/028308, entitled "Neuroprotective Bicyclic Compounds and Methods for Their Use," U.S. Provisional Patent Application Ser. No. 60/499,956 filed Sep. 3, 2003, entitled "Neuroprotective Bicyclic Compounds and Methods for Their Use," and U.S. patent application Ser. No. 13/043,215 filed Mar. 8, 2011, entitled "Cyclic Glycyl-2-AllylProline Improves Cognitive Performance in Impaired Animals." Each of the above patent applications and patents is expressly incorporated herein fully by reference.

Certain aspects of this invention include the use of cyclic G-2-AllylP in treatment of cognitive impairment associated with aging with neurodegenerative conditions or in situations in which cognitive impairment is found with no apparent neurodegeneration.

Scopolamine is commonly used in animal models of cholinergic hypofunction associated with Alzheimer's disease. The functional deficits observed after scopolamine treatment include those found in human patients with Alzheimer's disease. Thus, scopolamine treatment is reasonably predictive of cognitive impairment found in human diseases. Additionally, scopolamine treatment mimics cognitive dysfunction in humans who do not have neurodegenerative disorders.

cG-2-AllylP administered to animals treated with scopolamine-induced cognitive dysfunction produces clinical improvement in those animals, similar to the therapeutic improvement observed in people suffering from cholinergic hypofunction. For example, cholinergic hypofunction associated with Alzheimer's disease. Thus, studies of effects of Cyclic G-2-AllylP scopolamine treated animals are reasonably predictive of effects observed in human beings suffering from cholinergic dysfunction.

Other agents can be administered along with a compound of this invention. Such other agents may be selected from the group consisting of for example, growth factors and associated derivatives, e.g., insulin-like growth factor-1 (IGF-I), insulin-like growth factor-II (IGF-U), the tripeptide GPE, transforming growth factor-β1, activin, growth hormone, nerve growth factor, growth hormone binding protein, and/or IGF-binding proteins. Additional compounds include Glycyl-2-Methyl Prolyl Glutamate and/or other compounds disclosed in U.S. patent application Ser. No. 10/133,864, now U.S. Pat. No. 7,041,314, issued May 9, 2006, expressly incorporated herein fully by reference.

Therapeutic Applications

Compositions and methods of the invention find use in the treatment of animals, such as human patients, suffering from cognitive impairment and symptoms associated with ASDs and NDDs. Still more generally, the compositions and methods of the invention find use in the treatment of mammals, such as human patients, suffering from memory impairment, intellectual disability, impaired social interaction, impairments in communication, restricted and repetitive interests and behaviours and seizures.

Pharmaceutical Compositions and Administration

Cyclic G-2-AllylP can be administered as part of a medicament or pharmaceutical preparation. This can involve combining a compound of the invention with any pharmaceutically appropriate carrier, adjuvant or excipient. The selection of the carrier, adjuvant or excipient will of course usually be dependent upon the route of administration to be employed.

In general, compounds of this invention will be administered in therapeutically effective amounts by any of the usual modes known in the art, either singly or in combination with other conventional therapeutic agents for the disease being treated. A therapeutically effective amount may vary widely depending on the disease or injury, its severity, the age and relative health of the animal being treated, the potency of the compound(s), and other factors. As anti-apoptotic, anti-inflammatory and anti-necrotic agents, therapeutically effective amounts of cyclic G-2-

AllylP may range from 0.001 to 100 milligrams per kilogram mass of the animal, with lower doses such as 0.001 to 0.1 mg/kg being appropriate for administration through the cerebrospinal fluid, such as by intracerebroventricular administration, and higher doses such as 1 to 100 mg/kg being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

Cyclic G-2-AllylP and other cGP related compounds may be administered peripherally via any peripheral route known in the art. These can include parenteral routes for example injection into the peripheral circulation, subcutaneous, intraorbital, ophthalmic, intraspinal, intracisternal, topical, infusion (using e.g. slow release devices or minipumps such as osmotic pumps or skin patches), implant, aerosol, inhalation, scarification, intraperitoneal, intracapsular, intramuscular, intranasal, oral, buccal, transdermal, pulmonary, rectal or vaginal. The compositions can be formulated for parenteral administration to humans or other mammals in therapeutically effective amounts (e.g. amounts which eliminate or reduce the patient's pathological condition) to provide therapy for the neurological diseases described above.

Desirably, if possible, when administered as anti-apoptotic, anti-inflammatory and anti-necrotic agent, cyclic G-2-AllylP can be administered orally. The amount of a compound of this invention in the composition may vary widely depending on the type of composition, size of a unit dosage, kind of excipients, and other factors well known to those of ordinary skill in the art. In general, the final composition may comprise from 0.0001 percent by weight (% w) to 10% w of the compound of this invention, preferably 0.001% w to 1% w, with the remainder being the excipient or excipients.

Other convenient administration routes include subcutaneous injection (e.g. dissolved in a physiologically compatible carrier such as 0.9% sodium chloride) or direct administration to the CNS. Using stereotactic devices and accurate maps of an animals' CNS, a compound may be injected directly into a site of neural damage. Such routes of administration may be especially desired in situations in which perfusion of that location is compromised either by decreased vascular perfusion or by decreased cerebral spinal fluid (CSF) flow to that area. Examples include administration by lateral cerebroventricular injection or through a surgically inserted shunt into the lateral cerebroventricle of the brain of the patient, intravenously, direct injection into the desired location, either directly or indirectly via the circulation, or other routes.

By "directly or indirectly via the circulation" we mean administration of cG-2-AllylP to any tissue that has blood flow sufficient to deliver the agent into the circulation. Non-limiting examples include the skin, nose, pharynx, gastrointestinal tract, or other such tissue. When administered to such a tissue, the agent is absorbed by the tissue, where the agent enters the interstitial fluid of the tissue, and subsequently is absorbed by venules, capillaries, arterioles or lymph ducts. The agent is then carried into the general systemic circulation, where it can be delivered to the affected site, including the brain. When the agent is administered subcutaneously or peritoneally, the agent is absorbed by an adjacent tissue, and the agent then enters the circulation locally, and subsequently is delivered to the general circulation, where it can be transported to the brain. When the agent approaches the blood-brain barrier, the agent then can diffuse into the brain, either to neural tissue, or into the cerebrospinal fluid, where it can be delivered to neural tissues.

The effective amount of compound in the CNS may be increased by administration of a pro-drug form of a compound, which comprises a compound of the invention and a carrier, where the carrier is joined to a compound of the invention by a linkage which is susceptible to cleavage or digestion within the patient. Any suitable linkage can be employed which will be cleaved or digested following administration.

However, there is no intention on the part of the applicants to exclude other forms of administration.

In further embodiments of the invention, restoring nerve function in an animal can comprise administering a therapeutic amount of cyclic G-2-AllylP in combination with another neuroprotective agent, selected from, for example, growth factors and associated derivatives (insulin-like growth factor-I (IGF-I), insulin-like growth factor-II (IGF-II), transforming growth factor-01, activin, growth hormone, nerve growth factor, growth hormone binding protein, IGF-binding proteins (especially IGFBP-3), basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1), FHF-2, FHF-3 and FHF-4, karatinocyte growth factor 2, glial-activating factor, FGF-10 and FGF-16, ciliary neurotrophic factor, brain derived growth factor, neurotrophin 3, neurotrophin 4, bone morphogenetic protein 2 (BMP-2), glial-cell line derived neurotrophic factor, activity-dependent neurotrophic factor, cytokine leukaemia inhibiting factor, oncostatin M, interleukin), $\alpha$-, $\beta$-, $\gamma$-, or consensus interferon, and TNF-$\alpha$. Other forms of neuroprotective therapeutic agents include, for example, clomethiazole; kynurenic acid, Semax, tacrolimus, L-threo-1-phenyl-2-decanoylamino-3-morpholino-1-propanol, adrenocorticotropin-(4-9) analogue (ORG 2766) and dizolcipine (MK-801), selegiline; glutamate antagonists such as, NPS 1506, GV1505260, MK-801, GV150526; AMPA antagonists such as 2,3-dihydroxy-6-nitro-7-sulfamoylbenzo(f)quinoxaline (NBQX), LY303070 and LY300164; anti-inflammatory agents directed against the addressin MAdCAM-1 and/or its integrin $\alpha$4 receptors ($\alpha$4$\beta$1 and $\alpha$4$\beta$7), such as anti-MAdCAM-1 mAb MECA-367 (ATCC accession no. HB-9478).

Cyclic G-2-AllylP and other cGP related compounds are suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 38,481), copolymers of L-glutamic acid and gamma-ethyl-L-glutamate (Sidman et al., 1983, Biopolymers: 22: 547-36), poly(2-hydroxyethyl methacrylate) (Langer et al., 1981, J. Biomed. Mater. Res.: 15: 267), ethylene vinyl acetate (Langer et al., 1981, J. Biomed. Mater. Res.: 15: 267), or poly-D-(−)-3-hydroxybutyric acid (EP 133,988). Sustained-release compositions also include a liposomally entrapped compound. Liposomes containing the compound are prepared by methods known per se: DE 3,218,121, EP 52,322, EP 36,676, EP 88,046, EP 143,949, EP 142,641, Japanese Pat. Appln. 83-118008, U.S. Pat. Nos. 4,485,045 and 4,544, 545, and EP 102,324. Ordinarily, the liposomes are of the small (from or about 200 to 800 Angstroms) unilamellar type in which the lipid content is greater than about 30 mol percent cholesterol, the selected proportion being adjusted for the most efficacious therapy.

For parenteral administration, in one embodiment cyclic G-2-AllylP can be formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation.

For delivery of a compound of this invention to a mucosal tissue, one can incorporate the compound into a gel formulation. Once delivered to the mucosa (e.g., oral cavity, gastrointestinal tract, rectum), the agent can diffuse out of the gel, or the gel can be degraded, thereby releasing the agent into the tissue, where it can be absorbed into the circulation. Exemplary gel formulations can include those made with carboxypolysaccharides such as carboxymethyl cellulose, carboxyethyl cellulose, chitin, chitosan, starch, cellulose, proteins such as hyaluronic acid, or other polymers, such as polyvinylpyrollidine, polyvinyl alcohols, as well as other gel materials known in the art Generally, the formulations are prepared by contacting cyclic G-2-AllylP with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

A carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counterions such as sodium; non-ionic surfactants such as polysorbates, poloxamers, or polyethylene glycol (PEG); and/or neutral salts, e.g., NaCl, KCl, $MgCl_2$, $CaCl_2$, etc.

Cyclic G-2-AllylP and other cGP compounds typically formulated in such vehicles at a pH of from or about 4.5 to 8. It will be understood that use of certain of the foregoing excipients, carriers, or stabilizers will result in the formation of salts of the compound. The final preparation may be a stable liquid or lyophilized solid.

Formulations of cyclic G-2-AllylP in pharmaceutical compositions can also include adjuvants. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavouring agent such as peppermint, wintergreen, or cherry. When dosage forms are tablets, cyclic G-2-AllylP compositions can include binders and optionally, a smooth coating. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a colouring agent, and a flavouring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired, buffers, preservatives, antioxidants, and the like can be incorporated according to accepted pharmaceutical practice.

For injection, intraventricular administration, and other invasive routes of administration, cyclic G-2-AllylP must be sterile. Sterility may be accomplished by any method known in the art, for example filtration through sterile filtration membranes (e.g., 0.2 micron membranes). Therapeutic compositions generally are placed into a container having a sterile access port, for example, an intravenous solution bag or vial having a stopper able to be pierced by a hypodermic injection needle.

A pharmaceutical formulation containing cyclic G-2-AllylP ordinarily will be stored in unit or multi-dose containers, for example, in sealed ampoules or vials, as an aqueous solution or as a lyophilized formulation for reconstitution. As an example of a lyophilized formulation, 10 mL vials are filled with 5 mL of sterile-filtered 1% (w/v) aqueous solution of compound, and the resulting mixture is lyophilized. The infusion solution is prepared by reconstituting the lyophilized compound using bacteriostatic Water-for-Injection. It can be readily appreciated that other dosage forms and types of preparations can be used, and all are considered to be part of this invention.

Preparation of the Compounds

Starting materials and reagents used in preparing cyclic G-2-AllylP are either available from commercial suppliers such as Aldrich Chemical Company (Milwaukee, Wis.), Bachem (Torrance, Calif.), Sigma (St. Louis, Mo.), or are prepared by methods well known to the person of ordinary skill in the art following procedures described in such references as Fieser and Fieser's Reagents for Organic Synthesis, vols 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, $4^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art.

Starting materials, intermediates, and final products this invention may be isolated and purified using conventional techniques, including filtration, distillation, crystallization, chromatography, and the like. They may be characterized using conventional methods, including physical constants and spectral data.

Cyclic G-2-AllylP is a cyclic dipeptide (bicyclic 2,5-diketopiperazine), and is a member of the class of compounds known as cyclic GPx ("cGP"). In general, cGPs and cyclic G-2-AllylP may be prepared by methods such as are already well-known to persons of ordinary skill in the art of peptide and modified peptide synthesis, following the reaction schemes set forth in the Figures following this specification, or by following other methods well-known to those of ordinary skill in the art of the synthesis of peptides and analogues. See for example, Bodanzsky: Principles of Peptide Synthesis, Berlin, N.Y.: Springer-Verlag 1993.

Synthesis of the diketopiperazine compounds of this invention may be by solution-phase synthesis as discussed in the Examples or via the solid-phase synthesis method exemplified by Merrifield et al. 1963 *J. Amer. Chem. Soc.*: 83, 2149-2136. Solid phase synthesis may be performed using commercial peptide synthesizers, such as the Applied Biosystems Model 430A, using the protocols established for the instrument.

Specific examples of diketopiperazine synthesis can be found in the Examples following and in, for example, Fischer, 2003, *J. Peptide Science:* 9:9-33 and references therein. A person of ordinary skill in the art will have no difficulty, taking account of that skill and the knowledge available, and of this disclosure, in developing one or more suitable synthetic methods for compounds of this invention.

The choice of appropriate protecting groups for the method chosen (solid-phase or solution-phase), and of appropriate substrates if solid-phase synthesis is used, will be within the skill of a person of ordinary skill in the art. Appropriate protecting groups for peptide synthesis include r-butyloxycarbonyl (Boc), fluorenylmethyloxycarbonyl (Fmoc), Benzyl (Bzl), r-amyloxycarbonyl (Aoc), tosyl (Tos), benzyloxycarbonyl (Z or Cbz), o-bromo-benzyloxycarbonyl (BrZ) and the like. Additional protecting groups are identified in Goodman M. (ed.), "Synthesis of Peptides and Peptidomimetics" in Methods of organic chemistry (Houben-Weyl) (Workbench Edition, E22a,b,c,d,e; 2004; Georg Thieme Verlag, Stuttgart, N.Y.).

The choice of coupling agent for the method chosen will also be within the skill of a person of ordinary skill in the art. Suitable coupling agents include DCC (N, N'-Dicyclohexylcarbodiimide), Bop (Benzotriazole-1-yl-oxy-tris-(dimethylamino)-phosphonium hexafluorophosphate), PyBop (Benzotriazol-1-yl-oxytripyrrolidinophosphonium hexafluorophosphate), BopCl (bis(2-oxo-3-oxazolidinyl) phosphinic chloride), 2-Chloro-1,3-dimethylimidazolidinium hexafluorophosphate (CIP) and the like. Other compounds may be used in the synthesis e.g. to prevent racemisation, such as HOBt (N-Hydroxybenzotriazole) and HOAt (1-Hydroxy-7-azabenzotriazole).

EMBODIMENTS

The specific embodiments presented below are not intended to be limiting to the scope of the invention. Persons of skill in the art can create other embodiments by incorporating one or more of the elements in the listing below into combinations not specifically set forth herein. All such embodiments are considered to be within the scope of the invention.

Embodiment 1. A method for treating a symptom of an Autism Spectrum Disorder (ASD) or Neurodevelopmental Disorder (NDD) in an animal suffering from such a disorder, comprising administering to the animal, a compound having the formula:

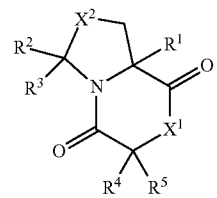

or a pharmaceutically acceptable salt or hydrate thereof, wherein
$X^1$ is selected from the group consisting of NR', O and S;
$X^2$ is selected from the group consisting of $CH_2$, NR', O and S;
$R^1$, $R^2$, $R^3$, $R^4$ and $R^5$ are independently selected from the group consisting of —H, —OR', —SR', —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;
or $R^4$ and $R^5$ taken together are —$CH_2$—$(CH_2)_n$—$CH_2$— where n is an integer from 0-6;
or $R^2$ and $R^3$ taken together are —$CH_2(CH_2)_n$—$CH_2$— where n is an integer from 0-6;
with the proviso that when $R^1$=methyl and $R^2$=$R^3$=$R^4$=H then $R^5 \neq$ benzyl and;
when $R^1$=H, at least one of $R^2$ and $R^3 \neq$H.

Embodiment 2. A method for treating a symptom of an Autism Spectrum Disorder (ASD) or Neurodevelopmental Disorder (NDD) in an animal suffering from such a disorder, comprising administering to the animal, a compound has the formula:

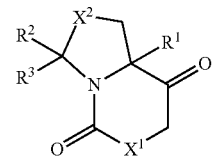

or a pharmaceutically acceptable salt or hydrate thereof, wherein
$X^1$ is selected from the group consisting of NR', O and S;
$X^2$ is selected from the group consisting of $CH_2$, NR', O and S;
$R^1$, $R^2$ and $R^3$ are independently selected from the group consisting of group consisting of —H, —OR', —SR'. —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;
or $R^2$ and $R^3$ taken together are —$CH_2$—$(CH_2)_n$—$CH_2$— where n is an integer from 0-6;
with the proviso that at least one R $4 \neq$ H.

Embodiment 3. A method for treating a symptom of an Autism Spectrum Disorder (ASD) or Neurodevelopmental Disorder (NDD) in an animal suffering from such a disorder, comprising administering to the animal, a compound has the formula:

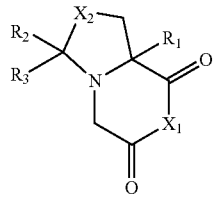

or a pharmaceutically acceptable salt or hydrate thereof, wherein
$X^1$ is selected from the group consisting of NR', O and S;
$X^2$ is selected from the group consisting of $CH_2$, NR', O and S;
$R^1$, $R^2$ and $R^3$ are independently selected from the group consisting of group consisting of —H, —OR', —SR', —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;
or $R^2$ and $R^3$ taken together are —$CH_2$—$(CH_2)_n$—$CH_2$— where n is an integer from 0-6.

Embodiment 4. A method for treating a symptom of an Autism Spectrum Disorder (ASD) or Neurodevelopmental Disorder (NDD) in an animal suffering from such a disorder, comprising administering to the animal, a compound of the formula:

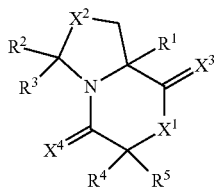

or a pharmaceutically acceptable salt or hydrate thereof, wherein
$X^1$, $X^3$, and $X^4$ are independently selected from the group consisting of S, O, and NH;
$X^2$ is selected from the group consisting of S, O, $CH_2$ and NH;
$R^1$, $R^2$, $R^3$, $R^4$ and $R^5$ are independently selected from the group consisting of —H, —OR', —SR', —NR'R', —$NO_2$. —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;
or $R^4$ and $R^3$ taken together are —$CH_2$—$(CH_2)_n$—$CH_2$— where n is an integer from 0-6;
or $R^2$ and $R^3$ taken together are —$CH_2$—$(CH_2)_n$—$CH_2$— where n is an integer from 0-6;
with the proviso that at least one R≠H and that both $X^3$ and $X^4$≠O.

Embodiment 5. A method for treating a symptom of an Autism Spectrum Disorder (ASD) or Neurodevelopmental Disorder (NDD) in an animal suffering from such a disorder, comprising administering to the animal, a compound of the formula;

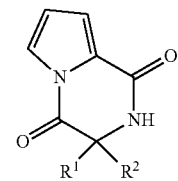

or a pharmaceutically acceptable salt or hydrate thereof, wherein
$R^1$ and $R^2$ are independently selected from the group consisting of group consisting of —H, —OR', —SR', —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;
or $R^1$ and $R^2$ taken together are —$CH_2$—$(CH_2)_n$—$CH_2$— where n is an integer from 0-6.

Embodiment 6. A method for treating a symptom of an Autism Spectrum Disorder (ASD) or Neurodevelopmental Disorder (NDD) in an animal suffering from such a disorder, comprising administering to the animal, a compound of the formula:

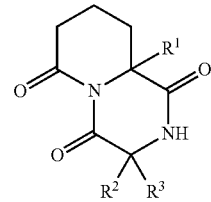

or a pharmaceutically acceptable salt or hydrate thereof, wherein
$R^1$, $R^2$ and $R^1$ are independently selected from the group consisting of group consisting of —H, —OR', —SR', —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^2$ and $R^3$ taken together are —$CH_2$—$(CH_2)_n$—$CH_2$— where n is an integer from 0-6.

Embodiment 7. A method for treating a symptom of an Autism Spectrum Disorder (ASD) or Neurodevelopmental Disorder (NDD) in an animal suffering from such a disorder, comprising administering to the animal, a compound of the formula:

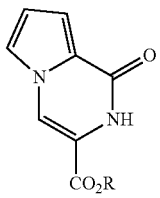

or a pharmaceutically acceptable salt or hydrate thereof, wherein

R is selected from the group consisting of alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl.

Embodiment 8. The method of any of embodiments 1 to 4 or 6 where $R^1$=methyl.

Embodiment 9. The method of any of embodiments 1 to 4 or 6 where $R^1$=allyl.

Embodiment 10. The method of any of embodiments 1 to 4 where $R^2$=$R^3$=methyl and $X^2$=S.

Embodiment 11. The method of embodiment 1 where $R^1$=allyl, $R^2$=$R^3$=$R^4$=$R^5$=H, $X^1$=NH, $X^2$=$CH_2$.

Embodiment 12. The method of embodiment 1 where $R^1$=methyl, $R^2$=$R^3$=H, $R^4$ and $R^5$ taken together are —$CH_2$—$(CH_2)_3$—$CH_2$—, $X^1$=NH, $X^2$=$CH_2$.

Embodiment 13. The method of embodiment 1 where $R^1$=methyl, $R^2$=$R^3$=H, $R^4$ and $R^5$ taken together are —$CH_2$—$(CH_2)_2$—$CH_2$—, $X^1$=NH, $X^2$=$CH_2$.

Embodiment 14. The method of any of embodiments 1 to 13, further comprising administering a pharmaceutically acceptable excipient.

Embodiment 13. The method of any of embodiments 1 to 13, further comprising administering a pharmaceutically acceptable excipient and a binder.

Embodiment 16. The method of any of embodiments 1 to 13, further comprising administering a pharmaceutically acceptable excipient and a capsule.

Embodiment 17. The method of any of embodiments 1 to 13, further comprising administering at least one other anti-apoptotic, anti-necrotic or neuroprotective agent.

Embodiment 18. The method of embodiment 17 where the other anti-apoptotic or neuroprotective agent is selected from selected from growth factors and associated derivatives (insulin-like growth factor-I [IGF-I], insulin-like growth factor-II [IGF-II], transforming growth factor-β1, activin, growth hormone, nerve growth factor, growth hormone binding protein, IGF-binding proteins [especially IGFBP-3], basic fibroblast growth factor, acidic fibroblast growth factor, the hst/Kfgk gene product, FGF-3, FGF-4, FGF-6, keratinocyte growth factor, androgen-induced growth factor, int-2, fibroblast growth factor homologous factor-1 (FHF-1), FHF-2, FHF-3 and FHF-4, keratinocyte growth factor 2, glial-activating factor, FGF-10 and FGF-16, ciliary neurotrophic factor, brain derived growth factor, neurotrophin 3, neurotrophin 4, bone morphogenetic protein 2 [BMP-2], glial-cell line derived neurotrophic factor, activity-dependent neurotrophic factor, cytokine leukaemia inhibiting factor, oncostatin M, an interleukin, α-interferon, β-interferon, γ-interferon, consensus interferon, TNF-α, clomethiazole; kynurenic acid, Semax, tacrolimus, L-threo-1-phenyl-2-decanoylamino-3-morpholino-1-propanol, adrenocorticotropin-(4-9) analogue [ORG 2766], dizolcipine [MK-801], selegiline, a glutamate antagonist, an AMPA antagonist, and an anti-inflammatory agent.

Embodiment 19. The method of embodiment 18 wherein said glutamate antagonist is selected from the group consisting of NPS1506, GV1505260, MK-801, and GV150526.

Embodiment 20. The method of embodiment 18 wherein said AMPA antagonist is selected from the group consisting of 2,3-dihydroxy-6-nitro-7-sulfamoylbenzo(f)quinoxaline (NBQX), LY303070 and LY300164.

Embodiment 21. The method of embodiment 18, wherein said anti-inflammatory agent is selected from the group consisting of an anti-MAdCAM-1 antibody and an antibody against an integrin α4β1 receptor and an integrin α4β7 receptor.

Embodiment 22. The method of embodiment 21 wherein said anti-MAdCAM-1 antibody is MECA-367.

Embodiment 23. The method of embodiment 1, wherein said compound is cyclic G-2-AllylP.

Embodiment 24. The method of embodiment 1, wherein said compound is cyclic cyclohexyl-G-2MeP.

Embodiment 23. The method of embodiment 1, wherein said compound is cyclic cyclopentyl-G-2MeP.

Embodiment 26. A method for treating a symptom of an Autism Spectrum Disorder (ASD) or Neurodevelopmental Disorder (NDD) in an animal suffering from such a disorder, comprising administering to the animal, a pharmaceutically effective amount of cyclic Glycyl-2-Allyl Proline (cG-2-AllylP) to said mammal.

Embodiment 27. The method of embodiment 26, wherein said cG-2-AllylP comprises an aqueous solution and one or more pharmaceutically acceptable excipients, additives, carriers or adjuvants.

Embodiment 28. The method of embodiment 26, further comprising one or more excipients, carriers, additives, adjuvants or binders in a tablet or capsule.

Embodiment 29. The method of any of embodiments 1 to 28, where the disorder is selected from the group consisting of Autistic Disorder, Asperger Syndrome, Childhood Disintegrative Disorder and Pervasive Developmental Disorder Not Otherwise Specified (PDD-NOS), and Pathological Demand Avoidance (PDA).

Embodiment 30. The method of any of embodiments 1 to 28, where the disorder is selected from the group consisting of Fragile X Syndrome (FXS), Angelman Syndrome, Tuberous Sclerosis Complex, Phelan McDermid Syndrome, Rett Syndrome, CDKL5 mutations, and X-Linked Infantile Spasm Disorder.

Embodiment 31. The method of any of embodiments 1 to 30, where the compound is administered either directly or indirectly via the circulation.

Embodiment 32. The method of any of embodiments 1 to 31, where said compound is administered via an oral, intraperitoneal, intravascular, peripheral circulation, subcutaneous, intraorbital, ophthalmic, intraspinal, intracisternal, topical, infusion, implant, aerosol, inhalation, scarification, intraperitoneal, intracapsular, intramuscular, intranasal, buccal, transdermal, pulmonary, rectal, or vaginal route.

Embodiment 33. The method of any of embodiments 1 to 32, where said effective amount has a lower limit of about 0.001 milligrams per kilogram mass (mg/kg) of the animal and an upper limit of about 100 mg/kg.

Embodiment 34. The method of any of embodiments 1 to 33, where assessment of efficacy is via measurement of phosphorylated ERK (pERK) or phosphorylated Akt (pAkt) in lymphocytes of the animal, where normalization of either pERK or pAkt indicates reduction in severity of said disorder.

Embodiment 33. The method of any of embodiments 1 to 33, wherein said treatment produces an improvement in a symptom of ASD or NDD as assessed using one or more clinical tests selected from the group consisting of The Rett Syndrome Natural History/Clinical Severity Scale, Aberrant Behavior Checklist Community Edition (ABC), Vineland Adaptive Behavior Scales, Clinical Global Impression of Severity (CGI-S), Clinical Global Impression Improvement (CGI-I), the Caregiver Strain Questionnaire (CSQ), or one or more physiological tests selected from the group consisting of electroencephalogram (EEG) spike frequency, overall power in frequency bands of an EEG, hemispheric coherence of EEG frequencies, stereotypic hand movement, QTc and heart rate variability (HRV), abnormal cellular expression of Phospho-ERK1/2 and Phospho-Akt, abnormal expression of growth-associated protein-43 (GAP-43), abnormal expression of synaptophysin (SYN), respiratory irregularities and coupling of cardiac and respiratory function compared to control animals not suffering from said disorder.

Embodiment 36. The method of any of embodiments 1-33, where said symptom of ASD is cognitive impairment or cognitive dysfunction, one or more signs or symptoms of memory loss, loss of spatial orientation, decreased ability to learn, decreased ability to form short- or long-term memory, decreased episodic memory, decreased ability to consolidate memory, decreased spatial memory, decreased synaptogenesis, decreased synaptic stability, deficits in executive function, deficits in cognitive mapping and scene memory, deficits in declarative and relational memory, decreased rapid acquisition of configural or conjunctive associations, decreased context-specific encoding and retrieval of specific events, decreased episodic and/or episodic-like memory, anxiety, abnormal fear conditioning, abnormal social behaviour, repetitive behaviour, abnormal nocturnal behavior, seizure activity, abnormal locomotion, abnormal cellular expression of Phospho-ERK1/2 and Phospho-Akt, and bradycardia.

Embodiment 37. A method for detecting presence of, severity, or evaluation of therapeutic efficacy of any of the preceding embodiments, comprising measuring expression of Phospho-ERK1/2 or Phospho-Akt in a peripheral lymphocyte of a subject with an ASD compared to the expression of Phospho-ERK1/2 or Phospho-Akt in a peripheral lymphocyte of a group of subjects not having an ASD, or to the expression Phospho-ERK1/2 or Phospho-Akt in a peripheral lymphocyte of the subject before treatment.

EXAMPLES

The present invention is further illustrated by the following examples. These examples are offered by way of illustration only and are not intended to limit the scope of the invention.

General Methods of Synthesis of Compounds

Flash chromatography was performed using Scharlau 60 (40-60 µm mesh) silica gel. Analytical thin layer chromatography was carried out on 0.20 mm pre-coated silica gel plates (ALUGRAM® SIL G/UV$_{254}$) and compounds visualized using UV fluorescence, or heating of plates dipped in potassium permanganate in alkaline solution.

Melting points in degrees Celsius (° C.) were determined on an Electrothermal® melting point apparatus and are uncorrected.

Optical rotations were measured at 20° C. on a Perkin Elmer 341 polarimeter using 10 cm path length cells and are given in units of $10^{-1}$ degcm$^2$ g$^{-1}$. Samples were prepared in the solvent indicated at the concentration specified (measured in g/100 cm$^3$). IR spectra were recorded on a Perkin Elmer Spectrum One FT-IR spectrometer. The samples were prepared as thin films on sodium chloride discs or as solids in potassium bromide discs. A broad signal indicated by br. The frequencies (☐) as absorption maxima are given in wavenumbers (cm$^{-1}$).

NMR spectra were recorded on a Broker AVANCE DRX400 ($^1$H, 400 MHz; $^{13}$C, 100 MHz) or a Broker AVANCE 300 ($^1$H, 300 MHz; $^{13}$C, 75 MHz) spectrometer at ambient temperatures. For $^1$H NMR data chemical shifts are described in parts per million downfield from SiMe$_4$ and are reported consecutively as position (5H), relative integral, multiplicity (s=singlet, d=doublet, t=triplet, dd=doublet of doublets, m=multiset, br=broad), coupling constant (J/Hz) and assignment. For $^{13}$C NMR data, chemical shifts are described in parts per million relative to CDCl$_3$ and are reported consecutively as position ($\delta_C$), degree of hybridization as determined by DEPT experiments, and assignment. $^1$H NMR spectra were referenced internally using SiMe$_4$ (δ 0.00) or CDCl$_3$ (δ 7.26). $^{13}$C NMR spectra were referenced internally using CDCl$_3$ (δ 77.0). When two sets of peaks arise in the NMR spectra due to different conformations around the glycine-proline amide bond, the chemical shift for the minor cis conformer is marked with an asterisk (*).

Accurate mass measurements were recorded on a VG-70SE mass spectrometer.

Hexane and dichloromethane were distilled prior to use. Methanol was dried using magnesium turnings and iodine, and distilled under nitrogen. Triethylamine was dried over calcium hydride and distilled under nitrogen.

Example 1: Synthesis of (8aS)-Methyl-hexahydro-pyrrolo[1,2-a]pyrazine-1,4-dione (Cyclic G-2MeP)

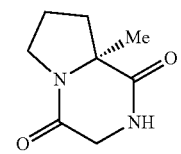

Scheme 1:

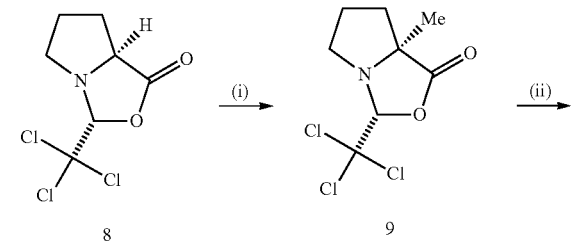

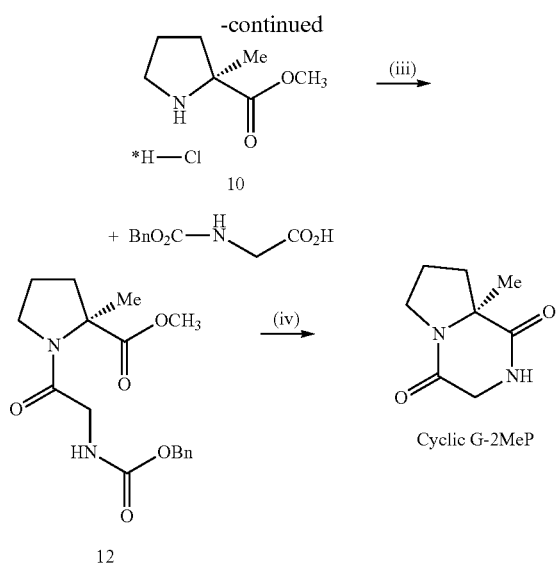

Reagents, conditions and yields: (i) LDA, THF, -78° C., iodomethane, -78 → -50° C., 2 h (63%); (ii) SOCl$_2$, CH$_3$OH, reflux, N$_2$, 2.5 H (98%); (iii) Et$_3$N, BoPCl, CH$_2$Cl$_2$, RT, N$_2$, 20.5 h (78%); (iv) 10% Pd/C, CH$_3$OH, RT, 15 h (98%).
(2R, 5S)-4-Methyl-2-trichloromethyl-1-aza-3-oxabicyclo[3.3.0]octane-4-one 9 n-BuLi (1.31 M, 4.68 cm$^3$, 6.14 mmol) was added dropwise to a stirred solution of diisopropylamine (0.86 cm$^3$, 6.14 mmol) in dry tetrahydrofuran (10 cm$^3$) at −78° C. under an atmosphere of nitrogen. The solution was stirred for 5 min, warmed to 0° C. and stirred for 15 min. The solution was then added dropwise to a solution of oxazolidinone 8 (1.00 g, 4.09 mmol) in dry tetrahydrofuran (20 cm$^3$) at −78° C. over 20 min (turned to a dark brown colour), stirred for a further 30 min then iodomethane (0.76 cm$^3$, 12.3 mmol) was added dropwise over 5 min. The solution was warmed to −50° C. over 2 h. Water (15 cm$^3$) was added and the solution warmed to room temperature and extracted with chloroform (3×40 cm$^3$). The combined organic extracts were dried (MgSO$_4$), filtered and evaporated to dryness in vacuo to give a dark brown semi-solid. Purification of the residue by flash column chromatography (15% ethyl acetate-hexane) afforded oxazolidinone 9 (0.67 g, 63%) as a pale yellow solid: mp 55-57° C. (lit., 57-60° C.); (300 MHz, CDCl$_3$) 1.53 (3H, s, CH$_3$), 1.72-2.02 (3H, m, Proβ-H and Proγ-H$_2$), 2.18-2.26 (1H, m, Proβ-H), 3.15-3.22 (1H, m. Proδ-H), 3.35-3.44 (1H, m, Proδ-H) and 4.99 (1H, s, NCH).

Methyl L-2-methylprolinate hydrochloride 10 a) Using acetyl chloride
Oxazolidinone 9 (0.60 g, 2.33 mmol) was dissolved in dry methanol (15 cm$^3$) under an atmosphere of nitrogen and acetyl chloride (0.33 cm$^3$, 4.66 mmol) was added drop wise to the ice-cooled solution. The solution was heated under reflux for 4.5 h, then the solvent removed under reduced pressure to give a brown oil which was purified by flash column chromatography (10% CH$_3$OH—CH$_2$Cl$_2$) affording the hydrochloride 10 (0.2 g, 48%) as a flaky white solid: mp 107-109° C. (lit., 106-108° C.); δ$_H$ (300 MHz, CDCl$_3$) 1.81 (3H, s, CH$_3$), 1.93-2.14 (3H, m, Proβ-H$_A$H$_B$ and Proγ-H$_2$), 2.33-2.39 (1H, m, Proβ-H$_A$H$_B$), 3.52-3.56 (2H, in, Proδ-H$_2$) and 3.82 (3H, s, CO$_2$CH$_3$).
b) Using thionyl chloride
An ice-cooled solution of oxazolidinone 9 (53 mg, 0.21 mmol) in dry methanol (1 cm$^3$) was treated dropwise with thionyl chloride (0.045 cm$^3$, 0.62 mmol). The solution was heated under reflux for 2.5 h, cooled and the solvent removed under reduced pressure to yield a brown oil. The oil was dissolved in toluene (5 cm$^3$), concentrated to dryness to remove residual thionyl chloride and methanol then purified by flash column chromatography (10% CH$_3$OH—CH$_2$Cl$_2$) to afford the hydrochloride 10 (16 mg, 43%) as a flaky white solid. The $^1$H NMR assignments were in agreement with those reported above.

Methyl-N-benzyloxycarbonyl-glycyl-L-2-methylprolinate 12

Dry triethylamine (0.27 cm$^3$, 1.96 mmol) was added dropwise to a solution of hydrochloride 10 (0.11 g, 0.61 mmol) and N-benzyloxycarbonyl-glycine 11 (98.5%) (0.17 g, 0.79 mmol) in dry dichloromethane (35 cm$^3$) under an atmosphere of nitrogen at room temperature, and the reaction mixture stirred for 10 min. Bis(2-oxo-3-oxazolidinyl) phosphinic chloride (BoPCl, 97%) (0.196 g, 0.77 mmol) was added and the resultant colourless solution was stirred for 20.5 h. The solution was washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (50-80% ethyl acetate-hexane; gradient elution) yielded dipeptide 12 (0.18 g, 92%) as a colourless oil. Amide 12 was shown to exist as a 98:2 trans:cis mixture of conformers by $^{13}$C NMR analysis (the ratio was estimated from the relative intensities of the resonances at δ 20.8 and 23.5 assigned to the Proγ-C atoms of the minor and major conformers, respectively): [α]$_D$ −33.0 (c 1.0 in MeOH); ν$_{max}$ (film)/cm$^{-1}$ 3406, 2952, 1732, 1651, 1521, 1434, 1373, 1329, 1310, 1284, 1257, 1220, 1195, 1172, 1135, 1107, 1082, 1052, 1029, 986, 965, 907, 876, 829, 775, 738 and 699; δ$_H$ (300 MHz, CDCl$_3$) 1.49 (3H, s, CH$_3$), 1.77-2.11 (4H, m, Proβ-H$_2$ and Proγ-H$_2$), 3.43-3.48 (2H, m, Proδ-H$_2$), 3.61 (3H, s, OCH$_3$), 3.85-3.89 (2H, in, Glyα-H$_2$), 5.04 (2H, s, PhCH$_2$). 5.76 (1H, br s, N—H) and 7.21-7.28 (5H, s, ArH); δ$_C$ (75 MHz, CDCl$_3$) 13.8* (CH$_3$, Proα-CH$_3$), 21.1 (CH$_3$, Proα-CH$_3$), 20.8* (CH$_2$, Proγ-C), 23.5 (CH$_2$, Proγ-C), 38.0 (CH$_2$, Proβ-C), 40.8* (CH$_2$, Proβ-C), 43.3 (CH$_2$, Glyα-C), 45.5* (CH$_2$, Glyα-C), 46.6 (CH$_2$, Proδ-C), 48.7* (CH$_2$, Proδ-C), 51.9* (CH$_3$, OCH$_3$), 52.1 (CH$_3$, OCH$_3$), 60.0* (quat., Proα-C), 66.0 (quat., Proα-C), 66.3 (CH$_2$, PhCH$_2$), 68.6* (CH$_2$, PhCH$_2$), 127.5 (CH, Ph), 127.6 (CH, Ph), 127.9* (CH, Ph), 128.1 (CH, Ph), 128.3* (CH, Ph), 136.2 (quat., Ph). 155.9 (quat., NCO$_2$), 166.0 (quat., Gly-CON), 169.4* (quat., Gly-CON) and 173.6 (quat., CO$_2$CH$_3$); m/z (EI+) 334.1535 (M$^+$. C$_{17}$H$_{22}$N$_2$O$_5$ requires 334.1529).

(8aS)-Methyl-hexahydropyrrolo[1,2-a]pyrazine-1,4-dione (Cyclic G-2MeP)

To a solution of dipeptide 12 (0.167 g, 0.51 mmol) in methanol (8.0 cm$^3$) was added 10% Pd on activated charcoal (8.1 mg, 0.076 mmol) and the vessel flushed with hydrogen gas. The resulting suspension was stirred vigorously under an atmosphere of hydrogen for 15 h. The mixture was then filtered through a Celite pad then a short plug of silica gel with methanol, and the solvent removed under reduced pressure to produce cyclic G-2MeP (83 mg, 98%) as a yellow solid: mp 133-135° C.; [α]$_D$ −128.1 (c 0.52 in MeOH); δ$_H$ (300 MHz, CDCl$_3$) 1.36 (3H, s, CH$_3$), 1.87-2.01 (3H, m, Proβ-H$_A$H$_B$ and Proγ-H$_2$), 2.07-2.21 (1H, m, Proβ-H$_A$H$_B$), 3.45-3.64 (2H, m, Proδ-H$_2$), 3.82 (1H, dd, J 17.1 and 4.1, CH$_A$H$_B$NH), 3.99 (1H, d, J 17.1, CH$_A$H$_B$NH) and 7.66 (1H, br s, N—H); δ$_C$ (75 MHz, CDCl$_3$) 20.2 (CH$_2$, Proγ-C), 23.2 (CH$_3$, Proα-CH$_3$), 35.0 (CH$_2$, Proβ-C), 44.7 (CH$_2$, Proδ-C), 45.9 (CH$_2$, CH$_2$NH), 63.8 (quat., Proα-C), 163.3 (quat., NCO) and 173.3 (quat., CONH); m/z (EI+) 168.08986 (M$^+$. C$_8$H$_{12}$N$_2$O$_2$ requires 168.08988).

Example 2: Synthesis of (8aS)-Methyl-spiro[cyclohexane-1,3(4H)-tetrahydropyrrolo[1,2-a]pyrazine]-1,4(2H)-dione (Cyclic cyclohexyl-G-2-MeP)

Scheme 2:

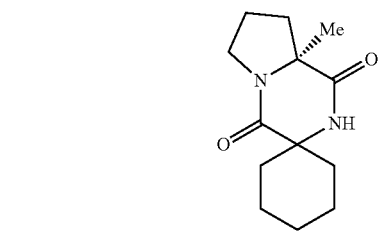

13

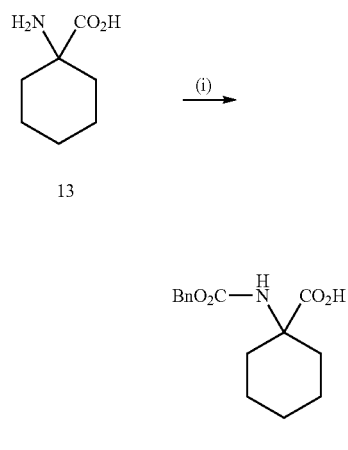

14

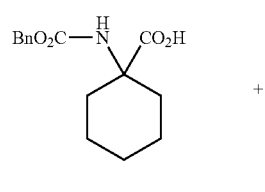

10

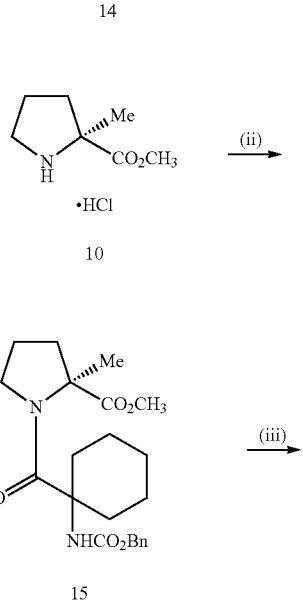

15

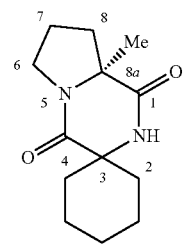

Cyclic cyclopentyl-G-2MeP

Reagents, conditions and yields: (i) BnO$_2$CCl, Na$_2$CO$_3$, H$_2$O-dioxane (3:1), 19 h, 96%; (ii) Et$_3$N, HOAt, CIP, 1,2-dichloroethane, reflux, N$_2$, 19 h (23%); (iii) 10% Pd/C, CH$_3$OH, RT, 17 h (65%).

N-benzyloxycarbonyl-1-aminocyclohexane-1-carboxylic acid (14)

To a suspension of 1-aminocyclohexanecarboxylic acid 13 (0.72 g, 5.02 mmol) and sodium carbonate (1.6 g, 15.1 mmol) were dissolved in water-dioxane (21 cm$^3$, 3:1) was added benzyl chloroformate (0.79 cm$^3$, 5.52 mmol) was added drop wise and the solution was stirred at room temperature for 19.5 h. The aqueous layer was washed with diethyl ether (60 cm$^3$), acidified with 2 M HCl and extracted with ethyl acetate (2×60 cm$^3$). The organic layers were combined, dried (MgSO$_4$), filtered and evaporated under reduced pressure to produce a colourless oil, which solidified on standing to crude carbamate 14 (1.23 g, 88%) as a white solid: mp 152-154° C. (lit., 148-150° C.); 4 (400 MHz, CDCl$_3$) 1.27-1.56 (3H, m, 3× cyclohexyl-H), 1.59-1.73 (3H, m, 3× cyclohexyl-H), 1.85-1.91 (2H, m, 2× cyclopentyl-H), 2.05-2.09 (2H, m, 2× cyclopentyl-H), 5.02 (1H, br s, N—H), 5.12 (2H, s, OCH$_2$Ph) and 7.27-7.36 (5H, s, Ph); 4(100 MHz, CDCl$_3$) 21.1 (CH$_2$, 2× cyclohexyl-C), 25.1 (CH$_2$, 2× cyclohexyl-C), 32.3 (CH$_2$, cyclohexyl-C), 59.0 (quat., 1-C), 67.1 (CH$_2$, OCH$_2$Ph), 128.1 (CH, Ph), 128.2 (CH, Ph), 128.5 (CH, Ph), 136.1 (quat., Ph), 155.7 (quat., NCO$_2$) and 178.7 (quat., CO$_2$H).

Methyl-N-benzyloxycarbonyl-cyclohexyl-glycyl-L-2-methylprolinate (15)

Dry triethylamine (0.21 cm$^3$, 1.5 mmol) was added dropwise to a solution of hydrochloride 10 (84.0 mg, 0.47 mmol), carboxylic acid 14 (0.17 g, 0.61 mmol) and 1-hydroxy-7-azabenzotriazole (16 mg, 0.12 mmol) in dry 1,2-dichloroethane (26 cm$^3$) under an atmosphere of nitrogen at room temperature, and the reaction mixture stirred for 10 min. 2-Chloro-1,3-dimethylimidazolidinium hexafluorophosphate (0.13 g, 0.47 mmol) was added and the resultant solution heated under reflux for 21 h, then washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (40-50% ethyl acetate-hexane; gradient elution) yielded amide 15 (16 mg, 9%) as a white solid. Amide 15 was shown to exist as a 11:1 trans:cis mixture of conformers by $^{13}$C NMR analysis (the ratio was estimated from the relative intensities of the resonances at δ 41.3 and 48.2 assigned to the Proδ-C atoms of the minor and major conformers, respectively): mp 219-222° C.; [α]$_D$ −44.9 (c 1.31 in CH$_2$Cl$_2$); ν$_{max}$ (film)/cm$^{-1}$ 3239, 2927, 1736, 1707, 1617, 1530, 1450, 1403, 1371, 1281, 1241, 1208, 1194, 1165, 1150, 1132, 1089, 1071, 1028, 984, 912, 796, 749, 739 and 699; $\delta_H$ (400 MHz, CDCl$_3$) 1.24-2.10 (17H, m, Proα-CH$_3$, Proβ-H$_2$, Proγ-H$_2$ and 5× cyclohexyl-H$_2$), 3.25-3.48 (1H, br m, Proδ-H$_A$H$_B$), 3.61-3.87 (4H, br m, OCH$_3$ and Proδ-H$_A$/H$_B$). 4.92-5.19 (3H, m, N—H and OCH$_2$Ph) and 7.35-7.37 (5H, s, Ph); $\delta_C$ (100 MHz, CDCl$_3$) 21.26 (CH$_2$, cyclohexyl-C), 21.33 (CH$_2$, cyclohexyl-C). 21.7 (CH$_3$, Proα-CH$_3$), 24.8 (CH$_2$, cyclohexyl-C), 25.0 (CH$_2$, Proγ-O, 29.4* (CH$_2$, cyclohexyl-C), 29.7* (CH$_2$, cyclohexyl-C), 31.1 (CH$_2$, cyclohexyl-C), 31.6 (CH$_2$, cyclohexyl-C), 31.9* (CH$_2$, cyclohexyl-C), 32.2* (CH$_2$, cyclohexyl-C), 32.8* (CH$_2$, cyclohexyl-C), 37.3 (CH$_2$, Proβ-C), 41.4* (CH$_2$, Proδ-C), 48.2 (CH$_2$, Proδ-C), 52.1 (CH$_3$, OCH$_3$), 59.1 (quat., Glyα-C), 66.7 (CH$_2$, OCH$_2$Ph), 67.3* (CH$_2$, OCH$_2$Ph), 67.4 (quat., Proα-C), 128.0* (CH, Ph), 128.1* (CH, Ph). 128.3 (CH, Ph), 128.5 (CH, Ph), 128.7 (CH, Ph), 136.6 (quat., Ph), 153.7 (quat., NCO$_2$), 171.0 (quat., Gly-CO) and 174.8 (quat., CO$_2$CH$_3$); m/z (EI+) 402.2151 (M*. C$_{22}$H$_{30}$N$_2$O$_5$ requires 402.2155).

(8aS)-Methyl-spiro[cyclohexane-1,3(4H)-tetrahydro-pyrrolo[1,2-a]pyrazine]-1,4(2-dione (Cyclic cyclohexyl-G-2MeP)

To a solution of amide 15 (40 mg, 0.01 mmol) in methanol (3.3 cm$^3$) was added 10% Pd on activated charcoal (1.6 mg, 0.015 mmol) and the vessel flushed with hydrogen gas. The resulting suspension was stirred vigorously under an atmosphere of hydrogen for 61.5 h, then filtered through a Celite™ pad with methanol (15 cm$^3$). The filtrate was concentrated to dryness under reduced pressure to produce a yellow semi-solid which was purified by reverse-phase C18 flash column chromatography (0-10% CH$_3$CN/H$_2$O; gradient elution) to produce cyclic cyclohexyl-G-2MeP (19 mg, 81%) as a white solid: mp 174-177° C.; [α]$_D$ −63.8 (c 1.13 in CH$_2$Cl$_2$); ν$_{max}$ (film)/cm$^{-1}$ 3215, 2925, 2854, 1667, 1646, 1463, 1427, 1276, 1232, 1171, 1085, 1014, 900, 868, 818, 783, 726 and 715; $\delta_H$ (400 MHz, CDCl$_3$) 1.31-1.89 (12H, m, 9× cyclohexyl-H and 8a-CH$_3$), 1.94-2.15 (4H, m, 7-H$_2$ and 8-H$_2$), 2.26 (1H, td, J 13.7 and 4.5, 1× cyclohexyl-H), 3.44-3.51 (1H, m, 6-H$_A$H$_B$), 3.79-3.86 (1H, m, 6-H$_A$H$_B$) and 6.40 (1H, hr s, N—H); $\delta_C$ (100 MHz, CDCl$_3$) 19.5 (CH$_2$, 7-C), 20.6 (CH$_2$, cyclohexyl-C), 20.8 (CH$_2$, cyclohexyl-C), 24.5 (CH$_2$, cyclohexyl-C), 25.0 (CH$_3$, 8a-CH$_3$), 33.7 (CH$_2$, cyclohexyl-C), 36.3 (CH$_2$, 8-C), 36.5 (CH$_2$, cyclohexyl-C), 44.7 (CH$_2$, 6-C), 59.5 (quat., 8a-C), 64.0 (quat., 3-C), 168.1 (quat., 4-C) and 171.6 (quat., 1-C); m/z (EI+) 236.15246 (M$^+$. C$_{13}$H$_{20}$N$_2$O$_2$ requires 236.15248).

Example 3: Synthesis of (8aS)-Allyl-hexahydropyrrolo[1,2-a]pyrazine-1,4-dione (Cyclic G-2-AllylP)

Scheme 3:

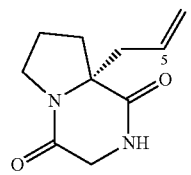

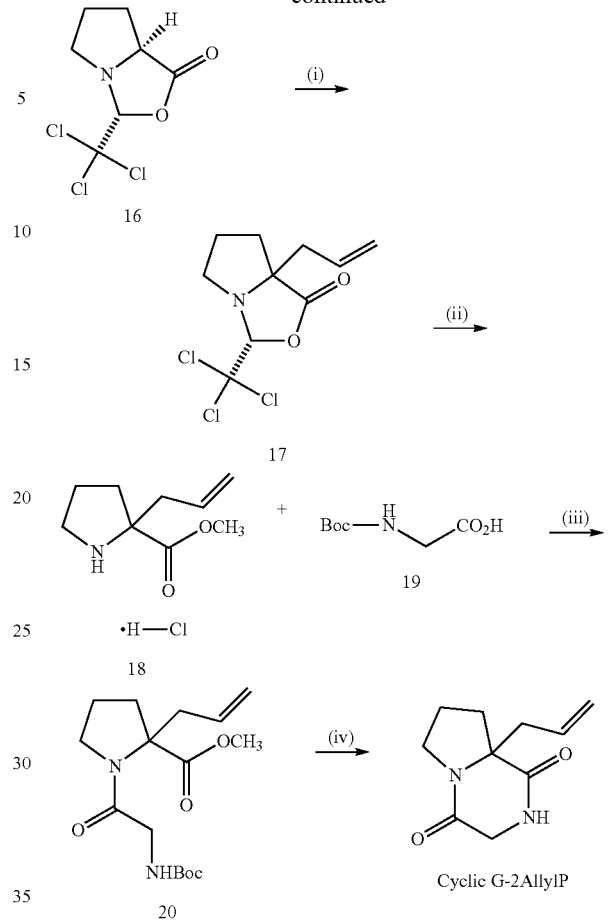

Reagents, conditions and yields: (i) LDA, THF, −78° C, allyl bromide, −78 → −30° C., N$_2$, 4 h (60%); (ii) acetyl chloride, CH$_3$OH, reflux, N$_2$, 24 h (63%); (iii) Et$_3$N, BoPCl, CH$_2$Cl$_2$, RT, N$_2$, 19.5 h (45%); (iv) TFA, CH$_2$Cl$_2$, 1 h, then Et$_3$N, CH$_2$Cl$_2$, 23 h (37%).

(2R,5S)-4-Allyl-2-trichloromethyl-1-aza-3-oxabicyclo[3.3.0]octan-4-one 17 n-BuLi (1.31 M, 9.93 cm$^3$, 13.0 mmol) was added dropwise to a stirred solution of diisopropylamine (1.82 cm$^3$, 13.0 mmol) in dry tetrahydrofuran (20 cm$^3$) at −78° C. under an atmosphere of nitrogen. The solution was stirred for 5 min, warmed to 0° C., stirred for 15 min then added dropwise to a solution of pro-oxazolidinone 16 (2.12 g, 8.68 mmol) in dry tetrahydrofuran (40 cm$^3$) at −78° C. over 20 min and the reaction mixture was stirred for a further 30 min then allyl bromide (2.25 cm$^3$, 26.0 mmol) was added dropwise over 5 min. The solution was warmed slowly to −30° C. over 4 h, quenched with H$_2$O (30 cm$^3$) and the mixture warmed to room temperature and extracted with chloroform (3×80 cm$^3$). The combined organic extracts were dried (MgSO$_4$), filtered and evaporated to dryness in vacuo to produce a dark brown semi-solid which was purified by flash column chromatography (10-20% ethyl acetate-hexane; gradient elution) to produce oxazolidinone 17 (1.48 g, 60%) as an orange oil which solidified at 0° C., for which the nmr data were in agreement with that reported in the literature: $\delta_H$ (400 MHz, CDCl$_3$) 1.58-1.92 (2H, m, Proγ-H$_2$), 1.96-2.14 (2H, m, Proβ-H$_2$), 2.50-2.63 (2H, m, Proδ-H$_2$), 3.12-3.23 (2H, m, CH$_2$—CH═CH$_2$), 4.97 (1H, s, NCH), 5.13-5.18 (2H, m, CH═CH$_2$) and 5.82-5.92 (1H, m, CH═CH$_2$;

δ$_C$ (100 MHz, CDCl$_3$) 25.1 (CH$_2$, Proγ-C), 35.1 (CH$_2$, Proβ-C), 41.5 (CH$_2$, Proδ-C), 58.3 (CH$_2$, CH$_2$CH=CH$_2$), 71.2 (quat., Proα-C), 100.4 (quat., CCl$_3$), 102.3 (CH, NCH), 119.8 (CH$_2$, CH$_2$CH=CH$_2$), 131.9 (CH, CH$_2$CH=CH$_2$) and 176.1 (quat., C=O); m/z (CI+) 284.0009 [(M+H)$^+$. C$_{10}$H$_{13}$$^{35}$Cl$_3$NO$_2$ requires 284.0012], 285.9980 [(M+H)$^+$. C$_{10}$H$_{13}$$^{35}$Cl$_2$$^{37}$ClNO$_2$ requires 285.9982], 287.9951 [(M+H)$^+$. C$_{10}$H$_{13}$$^{35}$Cl$^{37}$NO$_2$ requires 287.9953] and 289.9932 [(M+H)$^+$. C$_{10}$H$_{13}$$^{37}$Cl$_3$NO$_2$ requires 289.9923].

Methyl L-2-allylprolinate hydrochloride 18

An ice-cooled solution of oxazolidinone 17 (0.64 g, 2.24 mmol) in dry methanol (15 cm$^3$) was treated drop wise with a solution of acetyl chloride (0.36 cm$^3$, 5.0 mmol) in methanol (5 cm$^3$). The solution was heated under reflux for 24 h, then cooled and tire solvent removed under reduced pressure. The resultant brown oil was dissolved in toluene (40 cm$^3$) and concentrated to dryness to remove residual thionyl chloride and methanol, then purified by flash column chromatography (5-10% CH$_3$OH—CH$_2$Cl$_2$; gradient elution) to afford hydrochloride 18 (0.29 g, 63%) as a green solid for which the NMR data were in agreement with that reported in the literature: δ$_H$ (300 MHz, CDCl$_3$) 1.72-2.25 (3H, m, Proβ-H$_A$H$_B$ and Proγ-H$_2$), 2.32-2.52 (1H, m, Proβ-H$_A$H$_B$), 2.72-3.10 (2H, m, Proδ-H$_2$), 3.31-3.78 (2H, m, CH$_2$CH=CH$_2$), 3.84 (3H, s, CO$_2$CH$_3$). 5.20-5.33 (2H, m, CH=CH$_2$), 5.75-5.98 (1H, m, CH=CH$_2$) and 8.06 (1H, br s, N—H); m/z (CI+) 170.1183 [(M+H)$^+$. C$_9$H$_{16}$NO$_2$ requires 170.1181].

Methyl-N-tert-butyloxycarbonyl-glycyl-L-2-allyl-prolinate 20

Dry triethylamine (0.28 cm$^3$, 2.02 mmol) was added dropwise to a solution of hydrochloride 18 (0.13 g, 0.63 mmol) and N-tert-butyloxycarbonyl-glycine 19 (0.14 g, 0.82 mmol) in dry dichloromethane (35 cm$^3$) under an atmosphere of nitrogen at room temperature, and the reaction mixture was stirred for 10 min. Bis(2-oxo-3-oxazolidinyl) phosphinic chloride (BoPCl, 97%) (0.20 g, 0.80 mmol) was added and the solution stirred for 19.5 h, then washed successively with 10% aqueous hydrochloric acid (33 cm$^3$) and saturated aqueous sodium hydrogen carbonate (33 cm$^3$), dried (MgSO$_4$), filtered and evaporated to dryness in vacuo. Purification of the resultant residue by flash column chromatography (40% ethyl acetate-hexane) yielded dipeptide 20 (0.09 g, 45%) as a light yellow oil: [α]$_D$ +33.8 (c 0.83 in CH$_2$Cl$_2$); ν$_{max}$ (film/cm$^{-1}$ 3419, 3075, 2977, 2930, 2874, 1739, 1715, 1656, 1499, 1434, 1392, 1366, 1332, 1268, 1248, 1212, 1168, 1122, 1051, 1026, 1003, 943, 919, 867, 830, 779, 739, 699 and 679; δ$_H$ (300 MHz, CDCl$_3$) 1.42 [9H, s, C(CH$_3$)$_3$], 1.93-2.08 (4H, m, Proβ-H$_2$ and Proγ-H$_2$), 2.59-2.67 (1H, m, CH$_A$H$_B$CH=CH$_2$), 3.09-3.16 (1H, m, CH$_A$H$_B$CH=CH$_2$), 3.35-3.44 (1H, m, Proδ-H$_A$H$_B$), 3.56-3.62 (1H, m, Proδ-H$_A$H$_B$), 3.70 (3H, s, OCH$_3$), 3.89 (2H, d, J 4.2, Glyα-H$_2$), 5.06-5.11 (2H, m, CH=CH$_2$), 5.42 (1H, br s, Gly-NH) and 5.58-5.72 (1H, m, CH=CH$_2$); δ$_C$ (75 MHz, CDCl$_3$) 23.7 (CH$_2$, Proγ-C), 28.3 [CH$_2$, C(CH$_3$)$_3$], 35.0 (CH$_2$, Proβ-C), 37.6 (CH$_2$, CH$_2$CH=CH$_2$), 43.3 (CH$_2$, Glyα-C), 47.5 (CH$_2$, Proδ-C), 52.5 (CH$_3$, OCH$_3$), 68.8 (quat., Proα-C), 79.5 [quat., C(CH$_3$)$_3$], 119.4 (CH$_2$, CH=CH$_2$), 132.9 (CH, CH=CH$_2$), 155.7 (quat., NCO$_2$), 166.9 (quat., Gly-CON) and 173.8 (quat., CO$_2$CH$_3$); m/z (EI+) 326.1845 (M$^+$. C$_{16}$H$_{26}$N$_2$O$_5$ requires 326.1842).

(8aS)-Allyl-hexahydropyrrolo[1,2-a]pyrazine-1,4-dione (Cyclic G-2AllylP)

To a solution of dipeptide 20 (0.09 g, 0.28 mmol) in dichloromethane (9 cm$^3$) at room temperature was added trifluoroacetic acid (1 cm$^3$, 0.013 mmol) dropwise and the reaction mixture was stirred for 1 h under an atmosphere of nitrogen. The solution was evaporated under reduced pressure to give a colorless oil which was dissolved in dichloromethane (10 cm$^3$), dry triethylamine (0.096 cm$^3$, 0.69 mmol) was added and the reaction mixture stirred for 4.5 h, after which further triethylamine (0.0% cm$^3$, 0.69 mmol) was added. The reaction mixture was stirred overnight, concentrated to dryness to give a green oil which was purified by flash column chromatography (10% CH$_3$OH—CH$_2$Cl$_2$) to produce cyclic G-2AllylP (20 mg, 37%) as an off-white solid: mp 106-109° C.; [α]$_D$ −102.7 (c 0.95 in CH$_2$Cl$_2$); ν$_{max}$ (CH$_2$Cl$_2$)/cm$^{-1}$ 3456, 3226, 2920, 1666, 1454, 1325, 1306, 1299, 1210, 1133, 1109, 1028, 1010, 949, 928, 882, 793, 761 and 733; δ$_H$(400 MHz, CDCl$_3$) 1.92-2.01 (2H, m, Proγ-H$_2$), 2.09-2.16 (2H, m, Proβ-H$_2$). 2.39-2.56 (2H, m, CH$_2$CH$_2$=CH$_2$), 3.46-3.53 (1H, m, Proδ-H$_A$H$_B$). 3.78-3.87 (2H, m, Proδ-H$_A$H$_B$ and Glyα-H$_A$H$_B$). 4.09 (1H, d, J 17.2, Glyα-H$_A$H$_B$), 5.16-5.20 (2H, m, CH=CH$_2$), 5.73-5.84 (1H, m, CH=CH$_2$) and 7.17 (1H, br s, N—H); δ$_C$ (100 MHz, CDCl$_3$) 20.1 (CH$_2$, Proγ-C), 34.1 (CH$_2$, Proβ-C), 41.7 (CH$_2$, CH$_2$CH$_2$=CH$_2$), 44.9 (CH$_2$, Proδ-C), 46.4 (CH$_2$, Glyα-C), 67.2 (quat., Proα-C), 120.9 (CH$_2$, CH=CH$_2$), 131.0 (CH, CH=CH$_2$), 163.4 (quat., NCO) and 171.7 (quat., CONH); m/z (EI+) 195.1132 (M$^+$. C$_{10}$H$_{15}$N$_2$O$_2$ requires 195.1134).

Example 4: Synthesis of (8aS)-Methyl-spiro[cyclopentane-1,3(4H)-tetrahydropyrrolo[1,2-a]pyrazine]-1,4(2H)-dione (Cyclic Cyclopentyl-G-2-MeP)

Scheme 4:

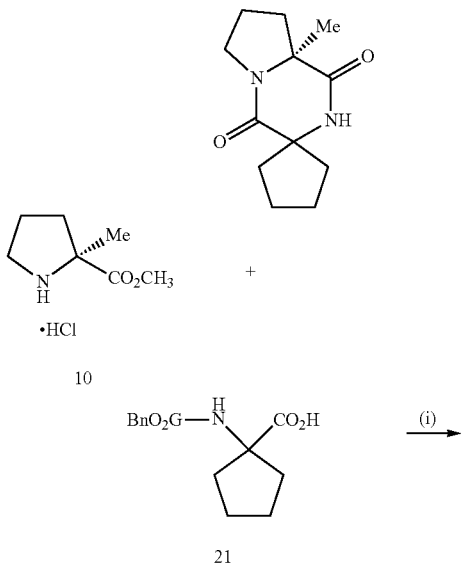

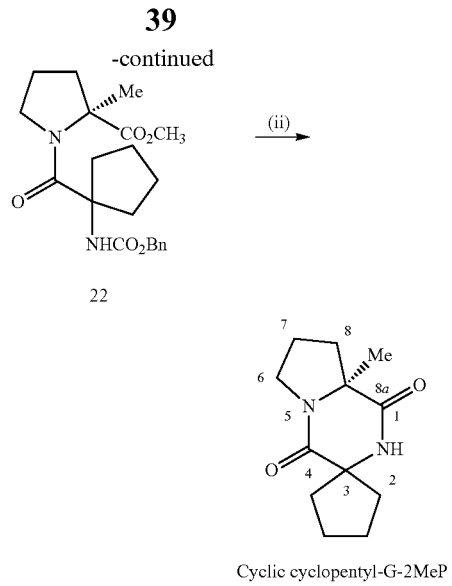

22

Cyclic cyclopentyl-G-2MeP

Reagents, conditions and yields: (i) Et$_3$N, HOAt, CIP, 1,2-dichloroethane, 83° C., N$_2$ 19 h (23%); (ii) 10% Pd/C, CH$_3$OH, RT, 17 h (65%).

N-Benzyloxycarbonyl-1-aminocyclopentane-1-carboxylic acid 21

A solution of benzyl chloroformate (0.290 g, 1.1 mmol) in dioxane (2.5 cm$^3$) was added dropwise to a solution of 1-aminocyclopentanecarboxylic acid (Fluka) (0.2 g, 1.54 mmol) and sodium carbonate (0.490 g, 4.64 mmol) in water (5 cm$^3$) at 0° C. Stirring was continued at room temperature overnight and the reaction mixture washed with ether. The aqueous layer was acidified with 2M hydrochloric acid, extracted with ethyl acetate, dried (Na$_2$SO$_4$), filtered and the solvent removed to afford carbamate 21 (0.253 g, 62%) as an oil which solidified on standing. Carbamate 21 was shown to be a 70:30 mixture of conformers by $^1$H NMR analysis (the ratio was estimated from the integration of the resonances at δ 5.31 and 7.29-7.40, assigned to the N—H protons of the major and minor conformers, respectively): mp 70-80° C. (lit.[1] 82-86° C., ethyl acetate, petroleum ether); δ$_H$ (400 MHz; CDCl$_3$; Me$_4$Si) 1.83 (4H, br s, 2× cyclopentyl-H$_2$), 2.04 (2H, br s, cyclopentyl-H$_2$), 2.20-2.40 (2H, m, cyclopentyl-H$_2$), 5.13 (2H, br s, OCH$_2$Ph), 5.31 (0.7H, br s, N—H) and 7.29-7.40 (5.3H, m, Ph and N—H*); δ$_C$ (100 MHz; CDCl$_3$) 24.6 (CH$_2$, cyclopentyl-C), 37.5 (CH$_2$, cyclopentyl-C), 66.0 (quat., cyclopentyl-C), 66.8 (CH$_2$, OCH$_2$Ph), 128.0 (CH, Ph), 128.1 (CH, Ph), 128.4 (CH, Ph), 136.1 (quat, Ph), 155.8 (quat., NCO$_2$) and 179.5 (quat., CO$_2$H).

* denotes resonance assigned to minor conformer.

Methyl N-benzyloxycarbonyl cyclopentyl-glycyl-L-2-methylprolinate 22

Dry triethylamine (0.19 cm$^3$, 1.4 mmol) was added dropwise to a solution of hydrochloride 10 (78 mg, 0.43 mmol), carboxylic acid 21 (0.15 g, 0.56 mmol) and 1-hydroxy-7-azabenzotriazole (Acros) (15 mg, 0.11 mmol) in dry 1,2-dichloroethane (24 cm$^3$) under an atmosphere of nitrogen at room temperature and the reaction mixture stirred for 10 min. 2-Chloro-1,3-dimethylimidazolidinium hexafluorophosphate (CIP) (Aldrich) (0.12 g, 0.43 mmol) was added and the resultant solution heated under reflux for 19 h, then washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (60% ethyl acetate-hexane) yielded amide 22 (39 mg, 23%) as a white solid. Amide 22 was shown to exist as a 3:1 trans:cis mixture of carbamate conformers by $^{13}$C NMR analysis (the ratio was estimated from the relative intensities of the resonances at δ 154.1 and 155.7 assigned to the carbamate carbonyl-C atoms of the major and minor conformers, respectively): mp 200-203° C.; [α]$_D$ −54.5 (c 1.52 in CH$_2$Cl$_2$); ν$_{max}$ (film)/cm$^{-1}$ 3432, 3239, 3042, 2953, 1736, 1712, 1627, 1540, 1455, 1417, 1439, 1374, 1282, 1256, 1216, 1194, 1171, 1156, 1136, 1100, 1081, 1042, 1020, 107, 953, 917, 876, 756 and 701; δ$_H$ (400 MHz, CDCl$_3$) 1.33-1.53 (3H, br m, Proα-CH$_3$), 1.62-2.20 (11H, m, Proβ-H$_2$, Proγ-H$_2$ and 7× cyclopentyl-H), 2.59-2.71 (1H, br m, 1× cyclopentyl-H), 3.31-3.42 (1H, br m, Proδ-H$_2$H$_B$), 3.58-3.79 (4H, br m, OCH$_3$ and Proδ-H$_A$H$_B$), 4.92-5.17 (3H, m, N—H and OCH$_2$Ph) and 7.27-7.42 (5H, s, Ph); δ$_C$ (100 MHz, CDCl$_3$) 21.7 (CH$_2$, Proα-CH$_3$), 24.1* (CH$_2$, cyclopentyl-C), 24.2 (CH$_2$, cyclopentyl-C), 24.4 (CH$_2$, Proγ-C), 24.5 (CH$_2$, cyclopentyl-C), 36.4 (CH$_2$, cyclopentyl-C), 37.1 (CH$_2$, cyclopentyl-C), 37.2* (CH$_2$, cyclopentyl-C), 37.7 (CH$_2$, Proβ-C), 38.2* (CH$_2$, cyclopentyl-C), 48.5 (CH$_2$, Proδ-C), 52.1 (CH$_2$, OCH$_3$), 66.6 (CH$_2$, OCH$_2$Ph), 66.9 (quat., Proα-C), 67.2 (quat., Glyα-C), 127.8 (CH, Ph), 128.2 (CH, Ph), 128.4 (CH, Ph), 136.6 (quat., Ph), 154.1 (quat., NCO$_2$), 155.7* (quat., NCO$_2$), 170.5 (quat., Gly-CO) and 174.7 (quat., CO$_2$CH$_3$); m/z (EI+) 388.1991 (M$^+$, C$_{21}$H$_{28}$N$_2$O$_5$ requires 388.1998).

(8aS)-Methyl-spiro[cyclopentane-1,3(4H)-tetrahydropyrrolo[1,2-a]pyrazine]-1,4(2H)-dione (Cyclic cyclopentyl-G-2MeP)

To a solution of amide 22 (54 mg, 0.14 mmol) in methanol (4.6 cm$^3$) was added 10% Pd on activated charcoal (2.2 mg, 0.021 mmol) and the vessel flushed with hydrogen gas. The resulting suspension was stirred vigorously under an atmosphere of hydrogen for 17 h, then filtered through a Celite™ pad with methanol (15 cm$^3$). The filtrate was concentrated to dryness under reduced pressure to give a yellow semi-solid which was purified by reverse-phase C18 flash column chromatography (0-10% CH$_3$CN/H$_2$O; gradient elution) to afford cyclic cyclopentyl-G-2MeP (20 mg, 65%) as a yellow solid: mp 160-163° C.; [α]$_D$ −97.9 (c 1.61 in CH$_2$Cl$_2$); ν$_{max}$ (film)/cm$^{-1}$ 3429, 2956, 2928, 2856, 1667, 1643, 1463, 1432, 1373, 1339, 1254, 1224, 1175, 1086, 1048, 976, 835, 774 and 730; δ$_H$ (300 MHz, CDCl$_3$) 1.47 (3H, hr s, 8a-CH$_3$), 1.56-2.19 (11H, m, 8-H$_2$, 7-H$_2$ and 7× cyclopentyl), 2.58-2.67 (1H, hr m, 1× cyclopentyl), 3.48-3.56 (1H, m, 6-H$_A$H$_B$), 3.72-3.82 (1H, m, 6-H$_A$H$_B$) and 6.56 (1H, br s, N—H); 4: (75 MHz, CDCl$_3$) 19.9 (CH$_2$, 7-C), 24.6 (CH$_2$, cyclopentyl), 24.92 (CH$_3$, 8a-CH$_3$), 24.93 (CH$_2$, cyclopentyl), 36.0 (CH$_2$, 8-C), 38.7 (CH$_2$, cyclopentyl), 41.9 (CH$_2$, cyclopentyl), 44.8 (CH$_2$, 6-C), 64.3 (quat., 8a-C), 66.8 (quat., 3-C), 168.3 (quat., 4-C) and 172.2 (quat, 1-C); m/z (EI+) 222.1369 (M$^+$, C$_{12}$H$_{18}$N$_2$O$_2$ requires 222.1368).

In Vitro and In Vivo Testing

The following pharmacological studies demonstrate efficacy of cyclic G-2-AllylP in attenuation of cognitive impairment. They are not intended to be limiting, and other compositions and methods of this invention can be developed without undue experimentation. All of those compositions and methods are considered to be part of this invention. All the following experiments were carried out using protocols developed under guidelines approved by the University of Auckland Animal Ethics Committee or comparable regulatory bodies.

Efficacy of nootropic drugs can be conveniently tested using models of cholinergic hypofunction. Cholinergic hypofunction has been shown to contribute to dementia-related cognitive decline and remains a target of therapeutic intervention for Alzheimer's disease (Hunter 2004). The cholinergic hypofunction model is also applicable to other conditions. For example, it has been shown that scopolamine-induced cholinergic hypofunction can selectively impair the recognition accuracy of disgust and anger facial expressions rendering the effect of scopolamine on emotion-recognition similar to those found in Huntington's disease patients (Kamboy 2006). Scopolamine has been commonly used to induce cholinergic hypofunction, and is a well-known model for human Alzheimer's disease, aging and other disorders of cognitive function (Liskowsky et at, Int. J. Dev. Neurosci, 24(2-3): 149-156 (2006), Lindner et al., Psychopharmacology (Berl.) September 27 (2006), Bouger et al., Eur. Neuropsychopharmacol 15(3):331-346 (2005), Ebert et al, Eur. J. Clin. Invest., 28(11):944-949 (1998), Barker et al, Int. J. Geriatr. Psychiatry, 13(4):244-247 (1998), G. Smith, Brain Res. 471(2):103-118 (1998), Flood et al, Behav. Neural. Biol. 45(2):169-184(1986)).

Example 5: Morris Water Maze (MWM) Model of Learning and Memory Used to Assess Effects of Cyclic G-2-AllylP on Cognitive Function The purpose of the study was to investigate cyclic G-2-AllylP in modes of cognitive deficit and affective state (anxiety).

Methods

The first part of the study involved acute testing of cG-2-AllylP in the Morris Water Maze Memory (MWM) model. The MWM test is one of the most frequently used tests for assessing spatial memory in rats and is well recognized to accurately predict effects of disease and treatment on spatial memory generally. Therefore, the MWM test reflects effects of disease and treatment in human subjects.

The standard procedure for MWM was followed. We used a circular swimming pool (80 cm depth×150 cm diameter) filled with opaque water, with the temperature maintained at 20° C. A platform was hidden 1 cm below the water surface, with a white flag (10 cm×10 cm) located either 20 cm above the platform for the visual cue and at 3 o'clock position in relation to the starting location for a spatial cue. On days 1-4 of the experiment rats underwent memory acquisition trials with 6 trials (60 seconds each) in each day of testing (habituation phase). Latency to reach the platform was recorded and the daily reduction of average latency was used to measure the capability to learn where the hidden platform was.

On day 3 of the experiment normal, non-aged Wistar rats were split into groups to receive either saline (n=28) or scopolamine (0.3 mg/kg, i.p., n=27) to induce memory deficit. Scopolamine 3 was administered half an hour before the probe test commenced.

10 min following the scopolamine treatment, the cyclic G-2AllylP was administered orally at 30 mg/kg (n=31) with vehicle-treated animals administered the diluent by oral gavage using an identical treatment protocol (n=24).

Acute effects of cG-2-AllylP were then tested in animals with scopolamine-induced memory impairment and in age-matched control animals with no memory impairment to determine any direct pharmacological effect on memory processing. Experimental groups are detailed in the Table 4 below.

TABLE 4

Animals Used to Test Effects of cG-2-AllylP on Memory

|  | Scopolamine | Vehicle |
|---|---|---|
| Vehicle | N = 12 | N = 12 |
| cG-2-AllylP | N = 15 | N = 16 |

On day 3, the probe MWM test was performed with the platform removed. There were 6 trials, each of maximum duration of 60s, at least 3 min rest between trials). The amount of tune the rats spend swimming near the platform provided a measure of how much they relied on visual and spatial cue to locate the platform, as opposed to using a non-spatial strategy. Data was collected and analysed using Any-maze (v4.2) software.

The data generated from behavioural tests was analysed using one-way ANOVA for determining the difference between the aged-groups. Two-way ANOVA was used for examining the progress of behavioral results with the time points treated as dependent factors. GraphPad Prism version 3.02 was used for data analysis.

Results

Treatment with scopolamine significantly impaired acquisition of spatial memory in treated animals (time to platform approximately 208% of control on day 4). Cyclic G-2AllylP (30 mg/kg; daily) significantly reversed the cognitive impairment induced by scopolamine (FIGS. 1A, 1B, 1C).

Example 6: cG-2-AllylP Improves Synaptic Plasticity and Aging-Related Memory Loss Methods Aged rats (male Wistar rats, 18-20 months old) were divided into four groups: two vehicle-treated (groups 1 and 3) and two G-2-AllylP treated (groups 2 and 4) (all groups n=6-8). Cyclic G-2-AllylP was synthesised by the Department of Medicinal Chemistry and dissolved in normal saline before the treatment. On day 1 a single dose of cyclic G-2-AllylP was given centrally (20 ng/animal, i.c.v.) to the animals in groups 2 and 4; saline was administered to groups 1 and 3. The memory tests using Novel Object Recognition Test started either on day 3 (groups 1 and 2) or 24 (groups 3 and 4) after the treatment. On the completion of the NORT, the rats were killed with an overdose of sodium pentobarbital and were perfused transcardially with normal saline followed by 10% formalin. Tissues collected at day 7 in groups 1 and 2, and at day 28 from groups 3 and 4. The brains were kept in the same fixative for a minimum of 2 days before being processed using a standard paraffin embedding procedure. Briefly, small blocks (10×10×3 mm) of tissue were fixed for up to 24 hrs. The blocks were then infiltrated and embedded with paraffin and cut in ribbons and mounted on slides. Slides were then stored until immunostaining was commenced. Synaptogenesis in brain tissue was examined using immunohistochemical staining.

Novel Object Recognition Test (NORT)

Exploratory activity is a typical learning behaviour displayed by animals including humans and rats in novel environments. Exploratory activity decreases over time when the novel becomes familiar and the habituation occurs. In familiar environments, exploratory activity can be reactivated by introducing a novel object. The increase in exploring behaviour once the environment is altered following a habituation provides a measure of the memory for the familiarity and the recognition of the novelty.

In this Example, we carried out two NORTs, one at days 3-6 and the other at 24-27 days. The rats were allowed to familiarise themselves with the testing arena (90×60×40 cm) in the first day of NORT. In the following two days of each test, four novel objects were placed into the testing arena and the rats had 2 trials each day (each of 15 min duration and 2 hours apart). The time spent on exploring the objects was reduced once the animal tested learned about the objects (training phase). In the last day (day 4 of each test), one familiar object was replaced by a novel object before the second trial (test 6, testing phase). The average time spent on exploring the 3 familiar objects and the time spent on exploration of the novel object was used as a measure for the memory of familiarity and the novelty recognition.

Effects of cG-2-AllylP on Expression of NMDA Receptors, AMPA Receptors, rKrox-24 and Synaptophysin mRNA in the Hippocampus It is accepted that the hippocampal formations in humans and animals play a crucial role in a number of memory types (Morris et al. 2006 Europ. J. Neurosci. 23, 2829). The specific functionality remains under dispute, but there is an understanding that hippocampus plays a key role in the automatic encoding and initial storage of attended experiences (episodic memory formation), memory consolidation and novelty detection. The first aspect, encoding and short-term storage of memories, is dependent on the synaptic plasticity and synaptic transmission, both of which are linked to glutamatergic neurotransmission.

Glutamatergic transmission is facilitated by two types of glutamate receptors: N-methyl-D-aspartate receptors (NMDAR) and a-amino-3-hydroxy-5-methyl-4-isoxalone propionic acid receptors AMPA or non-NMDA receptors.

APMA receptor subunit GluR1 is a post-synaptic receptor and has been commonly used for memory measurement. GluR1 is believed to mediate calcium influx, and has a vital function in synaptic plasticity related to learning. It has been previously suggested (Hayashi et al., 2000) that incorporation of GluR1 into synapses might be important for long-term potentiation (LTP), which is essential for learning and memory.

It had been demonstrated that NMDA receptor subunit NR1 is crucial for formation of spatial memory. In knockout models where the R1 subunit of the NMDA receptor in the pyramidal cells of the CA1 region was selectively knocked-out, the long-term potentiation was shown to be abolished (Tsien 1996).

Synaptophysin is a presynaptic vesicle protein. Its quantitative detection is established as a molecular marker of synaptic density.

The neuronal transcript factor Krox24 staining is used as a marker for neuronal plasticity. The protein products of the Krox24 family (as well as by brain-derived neurotrophic factor, BDNF) have recently linked with stabilizing synaptic modifications occurring during NMDA-receptor-mediated hippocampal LTP and LTD. (Dragunow. 2006. Behaviour genetics. 23; 293).

Immunohistochemical Staining

Conventional deparaffinisation and rehydration techniques were used to allow the water-based buffers and antibodies to penetrate the tissue slices. Antigen retrieval was used only prior to AMPA receptor (GluR1) staining, i.e. the slides were placed in boiling citrate buffer and allowed to cool.

The following antibodies were used:
i) primary rabbit antibody to NMDA NR1 subunit, at 1:200 concentration in buffer, incubated for 48 hrs (Chemicon—AB1516), followed by Sigma fluorescent secondary antibody (alexaFluor 394), at 1:200 dilution, incubated for 24 hours at 40C.
ii) primary antibody to AMPA GluR1 subunit, at 1:30 concentration in buffer, incubated for 48 hrs (Chemicon—AB1504) followed by 3,3'-diaminobenzidine (DAB) at 1:200 dilution, incubated for 24 hours at 40C.
iii) Primary antibody to mSynaptophysin (Sigma—S5768), at 1:200 concentration in buffer, followed by DAB at 1:200 dilution, incubated for 24 hours at 40C.
iv) Primary antibody to rKrox-24 (Santa Cruz—catalogue number SC-189) at 1:200 concentration in the buffer, followed by anti-rabbit secondary antibody at concentration of 1:200 dilution, incubated for 24 hours at 40C.
y) Antibodies were detected using light microscopy.

Results

NORT

A trend to improve the novelty recognition in the groups treated with cG-2-AllylP was observed after 27 days (FIG. 2), but not 6 days after the treatment (no figure). We conclude that the cG-2AllylP treatment improved novelty recognition in the drug-treated animals at 27 days.

AMPA Glutamate Receptor-1 Staining

Hippocampal slices from regions CA1 (granular cell layer, strata oriens and radiatum) and CA3 (pyramidal cell layer) were stained for AMPA receptors GluR1.

In CA3 there was no change in the number of receptors in each region on either day 7 or 28. There was however a significant increase in the number of AMPA receptors in CA1 (granular cell layer) (FIG. 4) and CA1 stratum oriens (FIG. 5) and on day 28.

That histological change was correlated with the improved performance in the novel object recognition test. The improved memory (FIG. 2) was correlated to the elevated AMPA glutamate receptor-1 (FIG. 3). We concluded that cG-2-AllylP improved glutamatergic neurotransmission (GluR1) at post-synaptic level.

We observed that cG-2-AllylP treatment resulted in a long term increase in GluR1 staining on the post-synapses and increased the density of pre-synaptic vesicles. As the majority of vesicles in the hippocampus are glutamic vesicles, we concluded that the long term memory improvement was associated with increased glutamic neurotransmission.

Synaptophysin Staining

We subsequently analysed effect of cG-2AllylP on the levels of synaptophysin staining in CA3 and CA1 regions of the hippocampus.

In all tested areas there was either a significant increase (CA3) or a clear trend towards (CA1—strata oriens and radiatum) the increase in the density of synaptophysin staining at 28 days post-treatment. That increase is a marker of increased synaptic plasticity and a clear indication of synaptogenesis which is a most likely cause of the improvement in the performance of the treated groups in applied memory tests.

NMDA Receptor-1 Staining

While there is a significant improvement in AMPA receptors post-treatment, the changes in the NMDA receptors are not so pronounced (FIGS. 9A, 9B and 9C).

Krox24 Staining

We analysed the density of the Krox24 staining in the CA1-2 regions of the hippocampus. We observed a trend towards the increased density in treatment group in comparison to the vehicle treated group. We conclude that the Krox24 staining results positively correlate with improved memory function (FIG. 10).

Example 7: cG-2-AllylP Increases the Number in Pre-Synaptic Vesicles in the Hippocampus of Middle Aged Rats Methods Four middle aged Wistar male rats (12 months) were divided into two groups: one vehicle-treated (n=2) and one cG-2-AllylP-treated (n=2). The rats were treated subcutaneously with 3 mg/kg/day of either saline or cG-2-AllylP for 7 days. On day 21 of the experiment the animals were sacrificed and the hippocampal tissue was harvested. Semi-thin sections of the tissue were fixed with $OsO_4$ and embedded in resin. CA1 stratum oriens and CA3 sections were then sliced into ultra-thin, 80 nm slices and stained with uranyl acetate and lead citrate. Approximately 30 synapses per animal were analysed, synapse type classified and vesicle density was measured using AnalySIS®.

Transmission electron microscopy was used to count the total number of vesicles on the slides. The average density was calculated by measuring the total area (using AxioVision software) and using the number of vesicles. We followed the protocol in Yoshida et al. 97, Journal of Neurochemistry to calculate the vesicle density in a 200 nm×200 nm square apposing the post-synaptic density (PSD).

Results

FIG. 6 is a graph showing the effect of cG-2-AllylP on the trend to increase the density of pre-synaptic stain in CA3 region of the hippocampus at day 24 post-treatment.

FIG. 7 is a graph showing the effect of cG-2-AllylP on the trend to increase the density of the pre-synaptic stain in the stratum oriens of the CA1 region on day 24 post-treatment.

FIG. 8 is a graph showing the effect of cG-2-AllylP to increase the density of the pre-synaptic stain in the stratum radiatum of the CA1 region on day 24 post-treatment.

The number of pre-synaptic vesicles in the CA1 and C3 subregions of the hippocampus was increased after cG-2-AllylP treatment (3 mg/kg/day×7 days, s.c.) compared to the vehicle treated animals at 21 days after the treatment (FIG. 11).

We conclude from these studies that scopolamine treatment can decrease cognitive function in animals, and that these changes can mimic cognitive impairment in human beings with one or more of a variety of neurological conditions. Additionally, we conclude that cG-2-AllylP can improve cognitive function in scopolamine-treated animals and in animals with normal aging-related cognitive impairment. Further, we conclude that cG-2-AllylP can increase synaptogenesis, increase AMPA receptors, increase neural plasticity, can stabilize synaptic modifications and can increase novelty recognition.

These studies therefore support the use of cG-2-AllylP as an effective pharmacological agent to treat a variety of cognitive impairments in animals including humans suffering from Alzheimer's disease, Parkinson's disease, and other chronic neural disorders, as well as cognitive impairment associated with aging.

Example 8: Effects of Cyclic G-2-AllylP and Cyclic cyclopentyl-G-2MeP on Cerebellar Cell Explants To determine the effects of cG-2-AllylP and cyclic cyclopentyl-G-2-MeP on neuronal cells in vitro, a series of studies was carried out using cerebellar explants from adult rats. In vitro systems are suitable for studying neuronal proliferation, neurite growth, formation of nerve bundles, and effects of toxins on neural cells, effects that parallel effects observed in vivo. Thus, results of studies using in vitro cerebellar explants are predictive of effects of interventions in vivo.

In a first series of studies, effects of glutamate on cerebellar explants were determined. At physiological concentrations, glutamate is a neurotransmitter in the CNS of mammals, including humans. However, at sufficiently high concentrations, glutamate is neurotoxic, resulting in neuronal cell death. Because glutamate is a naturally occurring neurotransmitter in the CNS of mammals, including humans, and because glutamate neurotoxicity is recognized in the art as reflective of neurotoxicity in general, and including cell death and degeneration, it is a valuable tool useful for identifying and characterizing agents effective in treatment of neurodegeneration and neural cell death.

Materials and Methods

Cover slips were placed into a large Petri dish and washed in 70% alcohol for 5 minutes, then washed with Millipore $H_2O$. The cover slips were air dried, and coated with Poly-D-Lysine (1 mg/ml stock solution in PBS, 90-100 µl) for 2 hours at 34° C.

Extraction of Cerebellar Tissue

Postnatal day 8 Wistar rats were used for the study. The rats were sacrificed and placed in ice for 1 minute, decapitated and the cerebellum removed and placed on ice. Cerebellum tissue was placed in 1 ml of 0.65% glucose-supplemented PBS (10 µl 65% stock D (+)glucose/1 ml PBS) in a large Petri dish, chopped up into smaller sections and triturated with a 1 ml insulin syringe via a 23 G (0.4 mm) needle, and then squirted back into the glucose solution in the large Petri dish. The tissue was sieved through (125 µm pore size gauze) and centrifuged (2 minutes at 60 g) twice to exchange the medium into serum-free BSA-supplemented START V medium (Biochrom, Germany). The second centrifugation step was done with 1 ml of START V medium. The microexplants were reconstituted into 500 µl of START V medium and put on ice.

Cultivation of Cerebellar Ceils

Two hours after PDL-coating, the slides were washed with Millipore $H_2O$ and air dried. Each slide was placed into a small Petri dish (diameter: 35 mm) and 40 µl of START V/cell suspension was added. The tissue was incubated for 2 hours at 34° C. (settlement period). START V-medium (1 ml) was then added to the Petri dish and cultivated at 34° C. in the presence of 5% $CO_2$ in air at 100% humidity for 48 hours.

Drug Application

For the study, certain explant cultures were exposed to vehicle (PBS) only. In the first study (Study 1) 10 µl of toxin 1 (L-glutamate—100 mM in Millipore water; final concentration; 1 mM) and 10 µl of toxin 2 (3-nitropropionic acid—50 mM—pH 7—in Millipore water, final concentration: 0.5 mM) was applied simultaneously with the drug to be tested (10 mM stock solution prepared in PBS and diluted to final concentrations between 1-100 nM). In each case, the drugs were left in contact with the explants for the duration of the study.

Methods for Determining Drug Effects

After explants were exposed to drugs for the study period, cells were then rinsed in PBS and then fixed in increasing concentrations of paraformaldehyde (500 μl of 0.4% PFA was applied; then 1.2% PFA; then 3% PFA and finally 4% PFA (each fixation step: 2-3 minutes). Finally, the microexplants were rinsed in PBS.

Neurons in the explants were then evaluated for morphology (presence of neurites) and counted as live cells per microscopic field. Four fields displaying highest cell density were counted per cover slip and the data presented as mean±standard error of the mean (SEM); n=4 each. Statistical significance was evaluated by using the non-paired Student's t-test.

Results

Cyclic G-2-AllylP

The results of the study are shown in FIG. 12. Glutamate treatment (1 mM; filled bar) resulted in about an 85% loss of cerebellar neurons having neurites compared to vehicle-treated controls (open bar). In contrast, cG-2-AllylP significantly increased the numbers of cells having neurites in a dose-dependent manner when administered simultaneously with glutamate (shaded bars). Treatment with low doses of cG-2-AllylP (100 pm to 10 nm) showed a significant decrease in glutamate-induced neurotoxicity.

Cyclic Cyclopentyl-G-2-MeP

The results of the study are shown in FIG. 13. Cyclic cyclopentyl-G-2MeP significantly increased the number of cells having neurites when simultaneously administered with glutamate (light shaded bars). Treatment with low doses of cyclic cyclopentyl-G-2MeP showed a significant decrease in glutamate-induced neurotoxicity.

Conclusions

Both cG-2-AllylP and cyclic cyclopentyl-G-2-MeP independently decreased or prevented glutamate-induced neurotoxicity, indicating that both drugs are neuroprotective and can be used to inhibit neuronal degeneration or cell death.

Example 9: Effects of cG-2-AllylP on Hypoxic-Ischemic Injury I

Materials and Methods

To determine whether cG-2-AllylP might prevent neuronal injury in response to stroke, cardiac arterial bypass graft surgery (CABG) or other hypoxic insults, a series of studies were carried out in rats that had been exposed to hypoxic-ischemic injury (HI).

Adult rats (Wistar, 280-310 g, male) were used. The modified Levine model preparation and experimental procedures were used (Rice et al, 1981, *Ann. Neurol.* :9: 131-141; Guan et al *J.*, 1993, *Cereb. Blood Flow Metab.*: 13(4): 609-16). These procedures in brief, consist of an HI injury induced by unilateral carotid artery ligation followed by inhalational asphyxia in the animals with an implanted lateral ventricular cannula. A guide cannula was stereotaxically placed on the top of the dura 1.3 mm to the right of the mid-line and 7.3 mm anterior to the interaural zero plane under halothane anaesthesia. The right carotid artery was double ligated two days after the cannulation. After 1 hour recovery from the anaesthesia, each of the rats were placed in an incubator where the humidity (90±5%) and temperature (31°±0.5° C.) were controlled for another hour, then exposed to hypoxia (6% oxygen) for 10 min. The animals were kept in the incubator for an additional 2 hours before treatment.

Nine pairs of rats were treated intracerebral ventricularly (icv) with either cG-2-AllylP (2 ng) or its vehicle (normal saline) 2 hours after hypoxic-ischemic insult. Rats in each group were simultaneously infused with cG-2-AllylP or its vehicle under light anaesthesia (1.3% halothane) 2 hours after the insult. A total volume of 20 μl was infused (icv) over 20 minutes by a micro-infusion pump.

Histological examination was performed on rats 5 days after the hypoxic-ischemic injury. The rats were killed with an overdose of sodium pentobarbital and were perfused transcardially with normal saline followed by 10% formalin. The brains were kept in the same fixative for a minimum of 2 days before being processed using a standard paraffin imbedding procedure.

Coronal sections 8 μm in thickness were cut from the striatum, cerebral cortex and hippocampus and were stained with thionin and acid fuchsin. The histological outcome was assessed at three levels: (1) the mid level of the striatum, (2) where the completed hippocampus first appeared and (3) the level where the ventral horn of the hippocampus just appears. The severity of tissue damage was scored in the striatum, cortex and the CA1-2, CA3, CA4 and dentate gyrus of the hippocampus. Tissue damage was identified as neuronal loss (acidophilic (red) cytoplasm and contracted nuclei), pan-necrosis and cellular reactions. Tissue damage was scored using the following scoring system: 0: tissue showed no tissue damage, 1: <3% tissue was damaged, 2: <50% tissue was damaged, 3: >50% tissue was damaged and 4: >95% tissue was damaged.

Results and Conclusion

The results of this study are shown in FIG. 14. FIG. 14 shows that hypoxic-ischemic injury (left bars of each set) resulted in significant damage scores in each of the areas of the brain studied. FIG. 14 also shows that central administration of a relatively low dose of cG-2-AllylP (right bars of each set; 2 ng) significantly reduced the tissue damage in each brain region examined compared to the vehicle treated group (p<0.001).

It can be seen that cG-2-AllylP can be neuroprotective against neural damage caused by hypoxic-ischemic injury, even when administered after hypoxic-ischemic injury. This surprising finding indicates that cG-2-AllylP is a useful agent to treat a variety of conditions characterized by neural degeneration or cell death.

Example 10: Effects of cG-2-AllylP on Hypoxic-Ischemic Injury II

Materials and Methods

Materials and methods described in Example 9 were used and the number of treatment groups was increased. Rats were divided into 5 treatment groups treated intracerebral ventricularly (icv) with one of 4 doses of cG-2-AllylP or with its vehicle (normal saline) 2 hours after hypoxic-ischemic insult (1: n=10, 2 ng; 2: n=9, 4 ng; 3: n=9, 20 ng; 4: n=10, 100 ng; and 5: n=9, vehicle).

Results

FIG. 15 shows hypoxia alone (vehicle) produces neuronal damage scores in all areas of the brain studied. In animals treated with cG-2-AllylP, hypoxia had less effect, even though the agent was administered after the hypoxic/ischemic injury. The neuroprotective effect was observed for all doses of cG-2-AllylP, except for the highest dose (100 ng) administered to the striatum. However, in all other sites and with all other doses, cG-2-AllylP lessened the neural damage effects of hypoxia/ischemia. Moreover, cG-2-AllylP had an increased efficacy in brain regions that experienced progressive injury associated with delayed cell death, such as that associated with apoptosis. In brain regions such as the dentate gyrus and the cerebral cortex, that are more resistant to HI injury, the progression of injury is known to be slower and more severe than in the brain regions that are more sensitive to HI injury such as the striatum and the CA1-2, CA3 and CA4 sub-regions of the hippocampus. This result shows that cG-2-AllylP can be beneficial in treatment of chronic neurological disorders.

Example 11: Effects of cG-2-AllylP in Fragile X Syndrome I General Methods

Experiments were conducted in accordance with the United Kingdom Animals (Scientific Procedures) Act of 1986. Fmr1-K02 mice and wildtype (WT) littermates were generated on a C57BL/6J background and repeatedly backcrossed onto a C57BL/6J background for more than eight generations and send to Chile by the Jackson's laboratory. Mice were grouping housed (4-6 per cage) and all animals were provided with ad libitum food and water unless otherwise stated. Mice were maintained on a 12 h light/dark cycle (lights off 19:00 to 7:00) in a temperature-controlled environment (21±1° C.).

Tasks were performed in the order described with no more than one task performed per day. All experiments were blind to the researcher performing the tests and the person injecting the mice.

Parametric data were analysed using two-way ANOVAs (genotype and sex as between-subject factors). Where data violated assumptions of normality or equality of variance, transformations (log 10 or square root) were utilised. For repeated measures ANOVAs, homogeneity of variance was tested using Mauchly's test of sphericity, and where this was violated, Huyn-Feldt corrections were used. Non-parametric data were analysed using Mann-Whitney U tests. A p-value <0.05 was considered statistically significant throughout.

No instances of toxicity have been observed. Animals were inspected for differences in coat appearance, whether any piloerection is present, eye condition (runny eyes or *porphyria*, ptosis) gait appearance, tremor, tail tone, reactivity to handling, etc.

Example 12: Effects of cG-2-AllylP on Hippocampal Neurons from Animals with Fragile X Syndrome To determine whether cG-2-AllylP can affect neurons, we carried out a series of studies on neurons in vitro from wild-type mice or fmr1-knockout mice.

Methods

Hippocampal cell cultures were prepared from wild type and fmr1-knockout fetal mice (14-16 days of gestation). Briefly, mice were kill by cervical dislocation under chloroform anesthesia, and dissociated hippocampal cells were plated in 13 mm multiwell vessels (Falcon Primaria). A plating medium of MEM-Eagle's salts (supplied glutamine free) supplemented with 10% fetal bovine serum was used. Cultures were kept at 37° C. in a humidified 3% $CO_2$ atmosphere. After 3d in vitro, green fluorescent protein (GFP) was added to monitor dendritic spine morphogenesis during time-course of culture (Ethell and Yamaguchi, 1999; Ethell et al., 2001, Henkemeyer et al., 2003). The dendritic spines usually formed between 7 and 14 days in vitro (DVI). By 14 DIV most dendritic protrusions were spines. The mean (±SD) spine density was measured as number of spines per micrometer and experiments were run in triplicate.

Results

Results of these studies is shown in FIGS. 16A-16D. FIG. 16A depicts a partition culture chamber for measurement of neuronal morphology. FIG. 16B shows a photomicrograph of hippocampal neurons treated with cG-2-AllylP ("NNZ 2591") at a concentration of 0.5 nM. We observed no statistically significant change (mean±SD, of n=3 independent experiments: 0.36±0.02).

In contrast, FIG. 16C shows a photomicrograph of cultured hippocampal neurons treated with cG-2-AllylP at a concentration of 5 nM (0.25±0.03). We observed a statistically significant effects when compared to control cultures (0.26±0.04).

FIG. 16D shows a photomicrograph of cultured hippocampal neurons treated with cG-2-AllylP. A significant effect on spine reduction was observed in cultures treated with cG-2-AllylP at a concentration of 50 nM (0.27±0.10). We observed no statistically significant difference from wild-type animals (0.26±0.05).

We conclude from these studies that cG-2-AllylP reduces dendritic spines in vitro, and this result indicates that cG-2-AllylP can improve neurological development and function in vivo, and therefore can be useful in treating Fragile X Syndrome in mice. Because the murine model for Fragile X Syndrome has the same genetic mutation found in human beings with Fragile X Syndrome, cG-2-AllylP can be effective in treating human beings with Fragile X Syndrome.

Example 13: Effects of cG-2-AllylP on Behavior in Animals With Fragile X Syndrome I: Anxiety and Memory To determine whether cG-2-AllylP has a beneficial effect in animals with Fragile X Syndrome, we carried out a series of studies on memory or habituation in vivo in wild-type and fmr1-knockout animals.

Methods

Animals

The fmr1-knockout 2 mice (C57BL/6 background) were housed in groups of the same genotype in a temperature and humidity controlled room with a 12-h light-dark cycle (lights on 7 am to 7 μm). Testing was conducted during the light phase. Food and water were available ad libitum. Testing was conducted on fmr1-knockout mice and their wild-type littermates. Experiments were conducted in line with the requirements of the UK Animals (Scientific Procedures) Act, 1986.

Studied Groups (n=10 each) were created according to the following.
1. fmr1-knockout (KO) treated with Vehicle
2. Wild type (Wt) treated with Vehicle
3. fmr1-knockout (KO) treated with cG-2-AllylP ("NNZ-2591")
4. Wild-type (Wt) treated with cG-2-AllylP.

Open Field Test for Anxiety

The Open Field (OF) test is a combined test that is used to determine anxiety/hyperactivity, and for habituation to a novel environment, one of the most elementary forms of learning, in which decreased exploration as a function of repeated exposure to the same environment is taken as an index of memory. This is normally studied in two sessions of exposure to the open field, a 10-min and a 24 hr habituation session.

FIG. 17 depicts a photograph of the device used for these studies. The open field is an exposed space in which movement can be tracked.

The device used for this study is a grey PVC enclosed arena 50×30 cm divided into 10 cm squares. Mice are brought to the experimental room 5-20 min before testing. A mouse is placed into a corner square facing the corner and observed for 3 min. The number of squares entered (whole body) and rears (both front paws off the ground, but not as part of grooming) are counted. The latency to the first rear is also noted. The movement of the mouse around the field was recorded with a video tracking device for 300s (vNT4.0, Viewpoint). The latency for the mouse to enter the brightest, central part of the field total time spent in this central region, and total activity (in terms of path length in centimeters), were recorded.

The open field (OF) test is a test used to characterize explorative behavior, anxiety, and or hyperactivity in animals habituated to daily handling under novel and familiar conditions. During exposure to the open field mice will habituate to the environment and thus explore less, decreasing the amount movement they show over time.

In the present experiment, we recorded movement and rearing during an initial exposure (T1), during a second exposure after 10 minutes (T2) and during a third exposure after 24 hours (T3). Failures to reduce locomotion or rearing at 10 minutes and 24 hours indicate deficits in short and long term memory, respectively.

Results cG-2-AllylP Decreases Anxiety in Animals with Fragile X Syndrome

FIG. 18 shows graphs of results of the OF test in which the number of squares entered (vertical axis) is plotted for each of the treatment groups. Vehicle-treated wild-type animals (left bar) travelled a total distance of about 80 squares during the T1 test period. Similarly, cG-2-AllylP ("NNZ 2591")-treated wild-type animals (third bar from left) entered about the same number of squares during this test period.

In contrast, vehicle-treated fmr1-knockout animals (second bar from left) entered more squares during the same time period (p<0.001). The magnitude of this effect was statistically significant and substantial, with these animals entering about 150 squares during the test period T1. However, we unexpectedly found that cG-2-AllylP ("NNZ 2591") significantly reduced the exploratory behavior of fmr1-knockout animals (right bar), with results comparable to those seen in vehicle-treated and cG-2-AllylP-treated wild-type animals (third bar from left).

We conclude from this result that cG-2-AllylP decreases anxiety in fmr1-knockout animals. Because the fmr1-knockout mice used in this study have the same genetic mutation as human beings with Fragile X Syndrome, we conclude that cG-2-AllylP can decrease anxiety in human beings with Fragile X Syndrome.

cG-2-AllylP Improves Short-Term Memory In Animals with Fragile X Syndrome

FIG. 19 shows graphs of results of the OF test at time period T2 (10 minutes), in which the number of squares entered (vertical axis) is plotted for each of the treatment groups. As with the results at T1 (FIG. 18), the vehicle-treated wild-type animals (left bar) and the cG-2-AllylP ("NNZ 2591")-treated wild-type animals (third bar from the left) demonstrated normal exploratory behavior, each group entering about 45 squares during time period T2. The distance travelled in the T2 test period was less than the distance travelled during T1, indicating that the animals had become at least partially habituated to the OF test by this time.

Vehicle-treated fmr1-knockout animals (second bar from the left) showed substantially more exploratory behavior than either of the first two groups of animals (p<0.001). In fact, the magnitude of the increase was about 2-fold, to about 100 squares.

In contrast, we unexpectedly found that cG-2-AllylP decreased the exploratory behavior of fmr1-knockout animals (right bar), and in fact, normalized the magnitude of their behavior to that of the wild-type animals.

We conclude from these results that: (1) Fragile X Syndrome in mice decreased short-term memory or habituation, and (2) cG-2-AllylP improved short-term memory or habituation in fmr1-knockout animals. Because the fmr1-knockout mice used in this study have the same genetic mutation as human beings with Fragile X Syndrome, we conclude that cG-2-AllylP can improve short-term memory in human beings with Fragile X Syndrome.

cG-2AllylP Improves Long-Term Memory in Animals with Fragile X Syndrome

FIG. 20 shows graphs of results of the OF test at time period T3, in which the number of squares entered (vertical axis) is plotted for each of the treatment groups. As with the results at T1 (FIG. 18) and T2 (FIG. 19), the vehicle-treated wild-type animals (left bar) and the cG-2-AllylP ("NNZ 2591")-treated wild-type animals (third bar from the left) demonstrated normal exploratory behavior, each group entering about 25-30 squares during T3. The distance travelled in the T3 test period was less than the distance travelled during T2, and further decreased compared to that observed at T1, indicating that the animals had become progressively habituated, and had a better long-term memory to the OF test by time period T3.

In contrast, vehicle-treated fmr1-knockout animals (second bar from the left) showed substantially more exploratory behavior (p<0.001), than the vehicle-treated or cG-2-AllylP-treated groups. In fact, the magnitude of the increase was about 2-fold, to about 100 squares. Interestingly, in fmr1-knockout animals, habituation failed to increase with time and exposure to the OF device. The number of squares entered at time period T3 was similar to that found at time periods T2 or T1.

We unexpectedly found that as with short-term memory, in fmr1-knockout animals, cG-2-AllylP substantially decreased (second bar from left), and in fact, normalized exploratory behavior at T3 compared to vehicle-treated Fmr1-knockout animals, indicating that long-term memory or habituation had returned to normal.

Conclusions

We conclude from these results that: (1) fmr1-knockout mice exhibited decreased long-term memory or habituation, and (2) cG-2-AllylP improved long-term memory or habituation in fmr1-knockout animals. Because the fmr1-knockout mice used in this study have the same genetic mutation as human beings with Fragile X Syndrome, we conclude that cG-2-AllylP can normalize long-term memory or habituation in human beings with Fragile X Syndrome.

Example 14: Effects of cG-2-AllylP on Behavior in Animals With Fragile X Syndrome II: Hyperactivity To determine whether cG-2-AllylP has a beneficial effect on hyperactivity in animals with Fragile X Syndrome, we carried out a series of studies in vivo in wild-type and fmr1-knockout mice.

Methods

Animals

The fmr1-knockout (KO2) mice (C57BL/6 background) were housed in groups of the same genotype in a temperature and humidity controlled room with a 12-h light-dark cycle (lights on 7 am to 7 μm). Testing was conducted during the light phase. Food and water were available ad libitum. Testing was conducted on fmr1-knockout mice and their wild-type littermates. Experiments were conducted according to requirements of the UK Animals (Scientific Procedures) Act, 1986. The animals were divided into four groups:

Vehicle-treated wild-type
Vehicle-treated fmr1-knockout;
cG-2-AllylP-treated wild-type; and
cG-2-AllylP-treated fmr1-knockout.

Successive Alleys Test

In one study, we used a "Successive Alleys Test" device. This device consists of four successive, linearly connected increasingly anxiogenic alleys. Each succeeding alley was painted a lighter color, had lower walls and/or was narrower than the previous alley. Animals were placed at the closed end of alley 1 (A1), facing the end wall. The latency to first enter each alley (A2, A3, and/or A4), the amount of time spent in each alley, and the number of entries into each alley were recorded during a total test time of 300 seconds.

For a Successive Alleys Test, we measured the number of entries in Alley 1 (A1), Alley 2 (A2), Alley 3 (A3), and Alley 4 (A4) for each of the 4 groups of animals described above.

Results

FIGS. 21 and 22 depict results of the Successive Alleys Test. FIG. 21 depicts a graph of results obtained in vehicle-treated animals. FIG. 22 depicts a graph of results obtained in cG-2-AllylP ("NNZ 2591")-treated animals. The number of entries is shown (vertical axis) for each of the treatment groups and entry into each alley (A1-A4) are shown. In FIG. 21, vehicle-treated animals showed exploratory behavior, with fmr1-knockout animals showing a larger number of entries than the wild-type animals. The vehicle-treated wild-type animals entered arms A1 (WT-A1) and A2 (WT-A2) about 3-4 times during the test period, and did not enter arms A3 (WT-A3) or A4 (WT-A4) significantly.

In contrast, vehicle-treated fmr1 knockout mice had a significantly shorter latency time to enter the first open alley ($p<0.001$) and spent significantly more time in the open alleys ($p<0.001$). These animals entered arms A1 (KO-A1) and A2 (KO-A2) about 10 times during the test period. The time the fmr1-knockout animals entered arms A1 and A2 more than twice the number of times as did wild type animals, indicating a significantly higher level of hyperactivity than the vehicle-treated wild-type animals. The vehicle-treated fmr1-knockout animals also made more crossings between alleys into arms A3 (KO-A3) and A4 (KO-A4) ($p<0.0001$).

We conclude from these results that fmr1-knockout mice exhibited greater anxiety that wild-type animals.

FIG. 22 shows results of the Successive Alleys Test in cG-2-AllylP ("NNZ 2591")-treated animals. cG-2-AllylP-treated wild-type animals entered arm A1 (WT-A1) about 2 times during the test period, and entered arm A2 (WT-A2) about 4 times during the test period. These results are comparable to the results obtained for vehicle-treated wild-type animals shown in FIG. 21.

In contrast, cG-2-AllylP-treated fmr1-knockout animals treated with cG-2-AllylP showed a significant reduction in open arm entries ($p<0.001$) as well as time spent in the center ($p<0.005$), indicating a reduction in hyperactivity compared to vehicle-treated fmr1-knockout animals. The magnitude of the effect of cG-2-AllylP was substantial, with cG-2-AllylP-treated fmr1-knockout animals entered arm A1 (KO-A1) about 4 times compared to about 8 times for the vehicle treated fmr1-knockout animals shown in FIG. 21. Similarly, cG-2-AllylP-treated fmr1-knockout animals entered arm A2 (KO-A2) about 4 times compared to about 10 times for the vehicle treated fmr1-knockout animals shown in FIG. 21. cG-2-Ally IP-treated fmr1-knockout animals entered arm A3 (KO-A3) about 4 times compared to about 9 times for the vehicle treated fmr1-knockout animals shown in FIG. 21. Finally, cG-2-AllylP-treated fmr1-knockout animals entered arm A4 (KO-A4) about 3 times compared to about 4 times for the vehicle treated fmr1-knockout animals shown in FIG. 21.

Conclusions

We conclude from this study that cG-2-AllylP decreased the anxiety in fmr1-knockout mice under these conditions. Because the fmr1-knockout mice used in this study have the same genetic mutation as human beings with Fragile X Syndrome, we conclude that cG-2-AllylP can be effective in treating human beings with Fragile X Syndrome.

Elevated Plus Maze

In another study, we used an "Elevated Plus Maze." The Elevated Plus Maze test is one of the most widely used tests for measuring anxiety-like hyperactivity in mice. The test is based on the natural aversion of mice for open and elevated areas, as well as on their natural spontaneous exploratory behavior in novel environments. FIG. 23 depicts a photograph of a device used in this study. The apparatus consists of two open arms and two closed arms, crossed in the middle perpendicularly to each other, and a center area. The open arms are more exposed and therefore create more anxiety in the mice. Mice therefore spend more time in the closed arms and visit them more frequently. Mice were given access to all of the arms and were allowed to move freely between them. The number of entries into the open arms, the time spent in the open arms, and time spent in the center were used as indices of open space-induced anxiety.

Time Spent in the Closed Arm

FIG. 24 shows results of studies using the Elevated Plus Maze on the amount of time spent in the closed arm (vertical axis) of the device for each of four groups of animals tested.

As shown in FIG. 24, vehicle-treated wild-type mice (left bar) spent about 240 seconds in the closed arm. cG-2-AllylP ("NNZ 2591")-treated wild-type mice (third bar from left) spent about the same amount of time in the closed arm.

In contrast, vehicle-treated fmr1-knockout animals (second bar from left0 spent significantly less time in the closed arm (about 160 seconds; $p<0.001$), indicating a state of hyperactivity in the fmr1-knockout animals. cG-2-AllylP normalized the time spent in the closed arm in fmr1-knockout animals (right bar). This hyperactivity was significantly reduced in the cG-2-AllylP-treated fmr1-knockout animals compared to the vehicle-treated wild-type and the cG-2-AllylP-treated wild-type animals. A statistically significant difference was observed between the vehicle-treated fmr1-knockout group and the cG-2-AllylP treated fmr1-knockout group ($p<0.001$).

We conclude from this study that cG-2-AllylP decreased the hyperactivity of fmr1-knockout mice under these conditions. Because the fmr1-knockout mice used in this study have the same genetic mutation as human beings with Fragile X Syndrome, we conclude that cG-2-AllylP can be effective in treating human beings with Fragile X Syndrome.

Elevated Plus Maze Time Spent In the Open Arm

FIG. 25 depicts graphs of results of this study, in which the time spent in the open arm (vertical axis) is shown for each of the 4 groups of animals tested.

The vehicle-treated fmr1-knockout animals (second bar from left) spent a significantly longer time in the open arms ($p<0.001$) compared to their vehicle-treated wild-type littermates (left bar). In contrast, cG-2-AllylP ("NNZ 2591") normalized the time spend in the open arms by the fmr1-knockout animals. The time spent in the open arm by the cG-2-AllylP treated fmr1-knockout animals mice did not significantly differ from that observed for the vehicle-treated wild type mice (left bar), or cG-2-AllylP treated wild-type animals (third bar from left).

We conclude from this study that: (1) fmr1-knockout animals exhibited more hyperactivity behavior than wild-type animals, and (2) cG-2-AllylP normalized the hyperactivity. Because the fmr1-knockout mice used in this study have the same genetic mutation as human beings with fragile X Syndrome, we conclude that cG-2-AllylP can be effective in treating human beings with fragile X Syndrome.

Elevated Plus Maze Time in the Center

FIG. 26 depicts graphs of the time spent in the center of the device (vertical axis), for each of the 4 groups of animals tested. The time spent in the center of the Elevated Plus Maze is recognized in the art as a measure of hyperactivity.

Vehicle-treated wild-type mice (left bar) spent about 30 seconds in the center of the maze. cG-2-AllylP ("NNZ 2591")-treated wild-type mice (third bar from left) spent slightly less time in the center than did vehicle-treated wild-type animals. In contrast, vehicle-treated fmr1-knockout mice spent significantly more time in the center (second bar from left; p<0.001) compared to vehicle-treated wild-type animals.

We unexpectedly found that cG-2-AllylP-treated fmr1-knockout mice (right bar) spent significantly less time than vehicle-treated fmr1-knockout animals (second bar from left). We observed statistically significant differences in time spent in the center for vehicle-treated fmr1-knockout animals (second bar from left), compared to vehicle-treated wild-type animals (left bar; p<0.001), cG-2-AllylP-treated wild-type animals (third bar from left; p<0.001), or cG-2-AllylP-treated fmr1-knockout animals (right bar, p<0.001). In fact, we observed no statistically significant differences between the time in the center spent by either the vehicle-treated wild-type group (left bar), the cG-2-AllylP-treated wild-type group (third bar from left) or the cG-2-AllylP-treated fmr1-knockout group (right bar).

We conclude from this study that cG-2-AllylP decreased the hyperactivity of fmr1-knockout mice under these conditions. Because the fmr1-knockout mice used in this study have the same genetic mutation as human beings with fragile X Syndrome, we conclude that cG-2-AllylP can be effective in treating human beings with Fragile X Syndrome.

Example 15: Effects of cG-2-AllylP on Fear Conditioning in Animals with Fragile X Syndrome Fear conditioning to either a cure or a context represents a form of associative learning that has been well used in many species. The dependent measure used in contextual (delay) fear conditioning is a freezing response that takes place following pairing of an unconditioned stimulus (foot shock), with a conditioned stimulus (CS), a particular context and/or such a cue. If in a conditioning context one administers a foot shock that is paired with atone, there will be learning not only to the tone, but also to the context.

Contextual fear conditioning is a bask conditioning procedure. It involves taking an animal and placing it in a novel environment, providing an aversive stimulus, and then removing it. When the animal is returned to the same environment, it generally will demonstrate a freezing response if it remembers and associates that environment with the aversive stimulus. Freezing is a response to fear, which has been defined as "absence of movement except for respiration." This freezing behavior may last from seconds to minutes depending on the strength of the aversive stimulus, the number of presentations, and the degree of learning achieved by the subject.

Methods

Animals

We used either wild-type or fmr1-knockout animals for this study, as described above. The animals were divided into groups as follows.

Vehicle-treated wild-type;
Vehicle-treated fmr1-knockout;
cG-2-AllylP-treated wild-type; and
cG-2-AllylP-treated fmr1-knockout.

Apparatus for Assessing Contextual Fear Conditioning

The device used in this study is depicted in FIG. 27. An unconditioned stimulus (mild shock to the feet) was applied, and the conditioned stimulus was a tone applied along with the shock to the feet. Under these conditions, the animals associate the unconditioned stimulus with both the conditioned stimulus and the context of the stimuli. Animals were tested for five (3) minutes.

Results

FIG. 28 depicts a graph of the time spent in "freezing behavior" for each of the groups of animals tested. Under acute stress conditions of this study, vehicle-treated wild-type animals (left bar) spent an average of about 30% of the five-minute test period (i.e., about 100 seconds). In contrast, vehicle-treated fmr1-knockout animals (second bar from left) spent substantially less time in freezing behavior (about 18% of the five-minute test period, or about 54 seconds). We conclude that the fmr1-knockout animals exhibited less fear than vehicle-treated wild-type animals.

We unexpectedly found that cG-2-AllylP ("NNZ 2591") produced a substantial and statistically significant increase in the time spent in freezing behavior in fmr1-knockout animals (right bar). In fact, the time spent in freezing behavior observed for cG-2-Allyl P-treated fmr1-knockout animals was similar to the time spent by the vehicle-treated wild-type animals (left bar) and the cG-2-AllylP=treated wild-type animals (third bar from left).

Conclusions

We conclude from this study that fmr1-knockout animals exhibited lower fear conditioning than wild-type animals. This indicates that fmr1-knockout animals may have a survival disadvantage compared to wild-type animals. We also conclude that cG-2-AllylP increased fear conditioning in fmr1-knockout mice under these conditions. This effect may mitigate the survival disadvantage observed in vehicle-treated fmr1-knockout animals. Because the fmr1-knockout mice used in this study have the same genetic mutation as human beings with Fragile X Syndrome, we conclude that cG-2-AllylP can be effective in treating human beings with Fragile X Syndrome.

Example 16: Effects of cG-2-AllylP on Marble Burying and Nesting Behavior in Animals with Fragile X Syndrome Mice are a social species, which engage in easily scored social behaviors including approaching, following, sniffing, allo-grooming, aggressive encounters, sexual interactions, and parental behaviors, nesting and sleeping in a group huddle, social recognition and social memory in mice are evaluated y the amount of time sent sniffing a novel mouse upon repeated exposures, to induce familiarity, and reinstatement of high levels of sniffing when a novel stimulus animal is introduced.

Marble Burying

Mice spontaneously dig in many substrates in the laboratory. This behavior comes from their ancestry in the wild, where they would forage for seeds, grain, insects, and other food to be found buried in the soil or leaf litter in their natural habitat. It exploits a common natural rodent behavior, provides quantitative data under controlled laboratory conditions, and has proved extremely sensitive to prion disease. Fragile X Syndrome, and brain lesions. Deterioration in the ability to perform "Activities of daily living" (ADL) is an early sign of Alzheimer's disease (AD), and cognitive decline (Deacon, 2012).

To study the effects of cG-2-AllylP on marble burying behavior, we earned out a series of studies on wild-type mice and fmr1-knockout mice.

Methods

Animals

We used either wild-type or fmr1-knockout animals for this study, as described above. The animals were divided into groups as follows.

Vehicle-treated wild-type;
Vehicle-treated fmr1-knockout;
cG-2-AllylP-treated wild-type; and
cG-2-AllylP-treated fmr1-knockout.

Mice were placed in an enclosed environment with a bed of wood shavings. Ten (10) marbles were introduced into the environment, and the number of marbles buried was determined by visual observation (median±interquartile range (IQR)).

Results

We observed that vehicle-treated wild-type mice and cG-2-AllylP-treated wild-type mice buried 10 out of 10 (100%) of the marbles presented. In contrast, fmr1-knockout animals buried significantly fewer marbles (average of 3 of 10 or 30%; (p<0.001) than vehicle-treated wild-type animals.

We unexpectedly found that cG-2-AllylP ("NNZ 2591")-treated fmr1-knockout animals buried a median of 8 of 10 marbles (80%). In fact, cG-2-AllylP normalized the number of marbles buried to levels very similar to those found for vehicle-treated wild-type mice, or cG-2-AllylP-treated wild-type mice.

Conclusions

We conclude from this study that fmr1-knockout mice buried fewer marbles than wild-type animals, and that cG-2-AllylP rescued this decrease, and in fact, normalized the behavior. Because the fmr1-knockout mice used in this study have the same genetic mutation as human beings with Fragile X Syndrome, we conclude that cG-2-AllylP can be effective in treating human beings with Fragile X Syndrome.

Nesting Behavior

Males and female mice make nests and perform this test equally, as purposes include thermoregulation as well as being associated with reproduction. This test is also used as an indicator of hippocampus lesion and dysfunction.

Methods

Animals

We used either wild-type or fmr1-knockout animals for this study, as described above.

The animals were divided into groups as follows.

Vehicle-treated wild-type;
Vehicle-treated fmr1-knockout;
cG-2-AllylP-treated wild-type; and
cG-2-AllylP-treated fmr1-knockout.

Test for Nesting Behavior

Mice typically use certain materials with which to make a nest. In this study, we introduced cotton "nestlets" into the nesting cages. Mice can then tear up and use the cotton of the nestlet and use it to make a next in the bedding of the nesting cages. Nesting is a typical behavior in mice, and represents an aspect of routine, daily living. This test is therefore reflective of daily living tasks carried out by human beings. Changes in nesting behavior in fmr1-knockout mice are therefore predictive of the behavior of human beings with Fragile X Syndrome. Further, effects of drugs on fmr1-knockout mice are reasonably predictive of effects of drugs on human beings with Fragile X Syndrome.

Mice were placed individually into nesting cages about one hour before the dark phase of the light-dark cycle, and the results were assessed the next morning. The appearance of the nestlets were evaluated according to a 5-point scale as described below, and the amount of untorn nestlet material was also weighed.

1. The nestlet was largely untouched (>90% intact). FIG. 20A depicts a photograph of a nestlet having a score of 1.
2. The nestlet was partially torn up (30-90% remaining intact). FIG. 20B depicts a photograph of a nestlet having a score of 2.
3. The nestlet was mostly shredded but often there is no identifiable nest site: <30% of the nestlet remains intact but <90% is within a quarter of the cage floor area, i.e. the cotton was not gathered into a nest but spread around the cage. The material may sometimes be in a broadly defined nest area but the critical definition is that 30-90% has been shredded. FIG. 29C depicts a photograph of a nestlet having a score of 3.

An identifiable, but flat nest: >90% of the nestlet was torn up, the material was gathered into a nest within a quarter of the cage floor area, but the nest is flat, with walls higher than mouse body height (curled up on its side) on less than 30% of its circumference. FIG. 29D depicts a photograph of a nestlet having a score of 4, with a mouse on top of the nestlet.

3. A near perfect nest: >90% of the nestlet was torn up, the nest is a crater, with walls higher than mouse body height on more than 30% of its circumference. FIG. 29E depicts a photograph of a nestlet having a score of 3, with a mouse on top of the nestlet.

Results and Conclusions

We found that vehicle-treated wild-type C37BL/6 mice scored between about 4-3 on nest construction. In contrast, for the vehicle-treated fmr1-knockout mice, the median score was around 1-2.

We unexpectedly found that cG-2-AllylP ("NNZ 2391") treatment increased the nesting score to about 4-3 in fmr1-knockout mice.

We conclude that fmr1-knockout mice demonstrated a deficit in next building, and that cG-2-AllylP at least partially reversed this deficit. Because the fmr1-knockout mice used in this study have the same genetic mutation as human beings with Fragile X Syndrome, we conclude that cG-2-AllylP can be effective in treating human beings with Fragile X Syndrome.

Example 17: Sociability: Social Recognition, Preference for Social Novelty

Mice are a social species, which engage in easily scored social behaviors including approaching, following, sniffing, allogrooming, aggressive encounters, sexual interactions, parental behaviors, nesting and sleeping in a group huddle.

To study sociability, we carried out a series of studies in wild-type mice, and mice with the fmr1-knockout mutation.

Methods

Animals

We used either wild-type or fmr1-knockout animals for this study, as described above.

The animals were divided into groups as follows.
Vehicle-treated wild-type;
Vehicle-treated fmr1-knockout;
cG-2-AllylP-treated wild-type; and
cG-2-AllylP-treated fmr1-knockout.

Test Procedures

Social recognition and social memory in mice were evaluated by the amount of time spent sniffing a novel mouse upon repeated exposures, to induce familiarity, and reinstatement of high levels of sniffing when a novel stimulus animal is introduced. We measured the number of bouts of sniffing in each of the groups of animals.

Results and Conclusions

FIG. 30 depicts a graph of the duration of bouts of sniffing (vertical axis) for the different groups of mice studied. We found that vehicle-treated wild-type animals (left bar) exhibited bouts of sniffing of about 23 during the test period. In contrast, fmr1-knockout animals (second bar from left) exhibited less sniffing behavior (about 6).

We surprisingly found, however, that in cG-2-AllylP ("NNZ 2591")-treated fmr1-knockout animals (right bar), the amount of sniffing behavior significantly increased to about 21 ($p<0.001$). In fact, cG-2-AllylP increased sniffing behavior in fmr1-knockout animals to about the same levels as in vehicle-treated wild-type (left bar) or cG-2-AllylP-treated animals (third bar from left).

We conclude that fmr1-knockout animals exhibited a deficit of sociability compared to wild-type animals. The results of this are consistent with the well-known deficits in sociability observed in human beings with Fragile X Syndrome. We also conclude that cG-2-AllylP increased sociability observed for fmr1-knockout mice, and normalized the behavior.

Because the fmr1-knockout mice used in this study have the same genetic mutation as human beings with Fragile X Syndrome, we conclude that cG-2-AllylP can be effective in improving social interactions in human beings with Fragile X Syndrome.

Example 18: cG-2-AllylP Normalizes Overexpression of pERK and pAKT in Animals with Fragile X Syndrome Neurons are critically influenced by Fragile X Mental Retardation Protein, which regulates local dendritic translation through phosphatidylinositol 3-kinase-Akt-mammalian target of rapamycin (mTOR) and Ras-ERK signalling cascades and implicated in the mGluR5 signalling cascade. Over-activation of the intracellular signalling molecules, ERK and Akt play a crucial role in synaptic plasticity. Levels of expression of these proteins is a feature of the cellular pathology of Fragile X Syndrome and is believed to contribute directly to the neurobehavioural phenotype of FXS. ERK is a classical MAPK signal transduction protein, responsible for growth factor transduction, proliferation, cytokine response to stress and apoptosis. Akt is a key component in the PI3K/Akt/mTOR signalling pathway and regulates cellular survival and metabolism by binding and regulating many downstream effectors, such as Nuclear Factor-κB (NfκB) and Bcl-2 family proteins. Excess activation (phosphorylation) of these proteins has been implicated in autism spectrum disorders.

Methods

Animals

We used either wild-type or fmr1-knockout animals for this study, as described above.

The animals were divided into groups (n=4 animals per group) as follows.
Vehicle-treated wild-type;
Vehicle-treated fmr1-knockout;
cG-2-AllylP-treated wild-type; and
cG-2-AllylP-treated fmr1-knockout.

Biochemical Tests

Phosphorylation levels of ERK1/2 and Akt of full brain lysates were evaluated using Western blots. The mice were sacrificed and the brains removed 12 days after the last injection, and immediately after the last behavioral test. Other studies measured pERK and pAkt in blood lymphocytes. The results of Western analysis were normalized to the amount of GAPDH protein seen in each blot.

Results

Phosphorylated ERK

FIG. 31 depicts graphs of results of the study on brains from the mice. Vehicle-treated wild-type mice had an average of about 0.9 (UA units) (left bar). In contrast, fmr1-knockout animals (second bar from left) had an increased level of phosphorylation ERK to about 1.3 (UA units) ($p<0.03$). Treatment of fmr1-knockout animals with c-2-AllylP ("NNZ 2591") (third bar from left) significantly reduced ERK phosphorylation ($p<0.03$) compared to vehicle-treated fmr1-knockout animals. The levels of pERK observed after treatment of fmr1-knockout animals with cG-2-AllylP were very similar to those of vehicle-treated wild-type animals (left bar) or cG-2-AllylP treated wild-type animals (third bar from left).

Similar results were found for pERK in lymphocytes isolated from the groups of animals.

Phosphorylated AKT

We observed a similar pattern in phosphorylated AKT as we did for ERK in brains of the animals. FIG. 32 depicts graphs of results of this study. Vehicle-treated wild-type mice had an average of about 0.9 (UA units) (left bar). In contrast, fmr1-knockout animals (second bar from left) had an increased level of phosphorylation AKT of about 1.3 (UA units) ($p<0.05$). Treatment of fmr1-knockout animals with c-2-AllylP ("NNZ 2591") (third bar from left) significantly reduced ERK phosphorylation to about 0.9 (UA units ($p<0.05$) compared to vehicle-treated fmr1-knockout animals. The levels of pAKT observed after treatment of fmr1-knockout animals with cG-2-AllylP were very similar to those of vehicle-treated wild-type animals (left bar) or cG-2-AllylP treated wild-type animals (third bar from left).

Similar results were found for pAkt in lymphocytes isolated from the groups of animals.

Example 19: Treatment of Rett Syndrome: Effects of cG-2-AllylP on Lifespan and Long-Term Potentiation in Rett Syndrome (RTT) Model To determine whether cG-2-AllylP treatment can impact the development and progression of Rett Syndrome in a murine model of the disorder, we use hemizygous MeCP2 (1lox) male mice. The MeCP2 knock-out (MeCP2-KO) mouse system is widely accepted in the art as closely mimicking the range and the severity of physiological and neurological abnormalities characteristic of the human disorder, Rett Syndrome.

All experiments are performed at the University of Texas Southwestern Medical Center and approved by the University of Texas Southwestern Medical Center Animal Care and Use Committee or similar approvals by other organizations. cG-2-AllylP was synthesised Albany Molecular Research Inc. (Albany, N.Y.) and supplied by Neuren Pharmaceuticals Limited.

Methods

Treatment

We treat hemizygous MeCP2(1lox) male mice with 20 mg/kg/day of cG-2-AllylP or saline, (0.01% BSA, n=15 per group in survival experiment and n=20 in the LTP experiment). The treatments are administered intraperitoneally from 4 weeks after birth. For the survival experiments the treatment is maintained through the course of the experiment. For the LTP experiment the mice are treated until week 9 when they are used for slice preparation.

Survival

MeCP2 deficient mutant mice develop RTT symptoms at about 4-6 weeks of age and the between 10-12 weeks (Chen et al., 2001. Nat Genet 27: 327-331). We compare the survival of the wild type controls and the MeCP2 deficient animals in vehicle- and cG-2-AllylP-treated groups. Survival is measured weekly from start of treatment (4 weeks) and used to produce Kaplan-Meier survival curves to show the proportion of mice that survive (y axis) at each weekly interval (x axis).

Long-Term Potentiation (Electrophysiology)

MeCP2 deficient mice have been previously reported to suffer from functional and ultrastructural synaptic dysfunction, significant impairment of hippocampus-dependent memory and hippocampal long-term potentiation (LTP) (Moretti et al. The Journal of Neuroscience. 2006. 26(1): 319-327). To test the effects of the cG-2-AllylP treatment on synaptic function in the RTT model we compare hippocampal LTP in both vehicle and cG-2-AllylP-treated animals at 9 weeks of age. To do so, we measure the slope of the fEPSP as a % of baseline potential in neurons in slices of hippocampus from MeCP2 deficient mice treated with either saline or cG-2-AllylP.

Results

Results show that cG-2-AllylP treatment increases survival of MeCP2 deficient mice. Wild-type mice (top line) are control animals, and therefore their survival is 100% at each time point. MeCP2 deficient mice treated with saline only the much more rapidly than wild-type mice, such that by about 11 weeks, only some of the MeCP deficient mice survive. In contrast, however, we find that MeCP2 deficient mice treated with cG-2-AllylP survive substantially longer than saline-treated mice. No safety concerns are raised by cG-2-AllylP treatment of mecp2 mice.

These results demonstrate that cG-2-AllylP can substantially increase survival of MeCP2 deficient mice. Because MeCP2 deficient mice are predictive of the pathology and therapeutic efficacy in human beings with Rett Syndrome, we conclude that cG-2-AllylP can increase life span of human beings with Rett Syndrome.

Results also show that cG-2-AllylP treatment increases hippocampal long-term potentiation (LTP) as measured by the fEPSP slope in MeCP2 deficient animals compared to saline-treated mutant mice. We find that cG-2-AllylP increases the slope of fESPS in MeCP2 deficient mice compared to animals treated with saline only.

These results demonstrate that cG-2-AllylP can be effective in treating MeCP2 deficient mice in vivo. Because MeCP2 deficient mice are predictive of the pathology and therapeutic efficacy in human beings with Rett Syndrome, we conclude that cG-2-AllylP can be an effective therapy for human beings with Rett Syndrome.

Example 20: cG-2-AllylP Improves Dendritic Arborization and Increases Dendritic Spine Length We assess the effects of cG-2-AllylP treatment on dendrites. Transgenic mecp2 knockout mice (n=15 to 20) are administered cG-2-AllylP intraperitoneally at a dose of 20 mg/kg once daily. Following sacrifice dendritic spine density, spine length and aborization are examined after Golgi staining after nine weeks, according to Table 5 below.

TABLE 5

Sample Sizes for all Neuron Morphology and Spine Analysis

| Analysis | AGE (Weeks) | MALE No. of mice | | No. of of neurons or dendrites per animal | |
|---|---|---|---|---|---|
| | | KO-vehicle | KO-cG-2-AllylP | KO-vehicle | KO-cG-2-AllylP |
| Morphology | 9 | 3 | 3 | 4 | 4 |
| Spine Analysis | 9 | 3 | 3 | 10 | 10 |

Dendritic length is assessed by distance from the soma of representative hippocampal CA1 neurons from 9 week old male mecp2 null mutant mice treated with either saline (3 neurons analysed from 3 separate mice, n=9) or cG-2-AllylP (20 mg/kg i.p. 1/day, from week 4; 3 neurons are analysed from 3 separate mice, n=9).

We observe that cG-2-AllylP improves dendritic arborization and increases dendritic spine length. Dendritic length in $\mu m$ (vertical axis) is plotted against the distance (in $\mu m$; horizontal axis) from the soma of the cells. For cells with dendrites close to the so mas, the dendrites are short. However, as the distance from the somas increases, saline-treatment produces dendritic lengths that increase to a maximum at a distance of about 70 $\mu m$ from the soma and decline at distances further away from the somas. In contrast, treatment with cG-2-AllylP (filled squares) produces longer dendrites over much of the range of distances from the somas.

Example 21: Treatment of Rett Syndrome in Mice II: Mice Mating and Genotyping

The MeCP2 germline null allele mice are used (Chen et al., 2001). Genotyping is performed as in Chen et al. (Chen et al., 2001).

cG-2-AllylP Treatment

For the survival measurements, the nocturnal activity analysis and the immunoblot analysis, cG-2-AllylP supplied by Neuren Pharmaceuticals Limited is administered daily via intra-peritoneal injections (20 mg/kg, vehicle=saline, 0.01% BSA). The treatment starts at PI 5 and is maintained throughout the course of the experiments. For intracellular physiology experiments, the mice are injected daily with cG-2-AllylP (20 mg/kg body weight, vehicle=saline, 0.01% BSA) for 2 weeks, from P15 to P28-P32 when they are used for acute slice preparation. For optical imaging experiments, mice are injected with cG-2-AllylP (20 mg/kg body weight, vehicle=saline, 0.01% BSA) daily from the day of the lid suture to the day of imaging.

Slice Physiology Preparation

Coronal sections (300 μm thick) at or near sensorimotor cortex are cut in <4° C. ACSF using a Vibratome. Slices are incubated at 37° C. for 20 minutes after slicing, and at room temperature for the remainder of the experiment. Slices are transferred to a Warner chamber and recordings are taken from visually identified pyramidal neurons located in layer 3. Artificial cerebral spinal fluid (ACSF) containing 126 mM NaCl, 23 mM NaHCO$_3$, 1 mM NaHPO$_4$, 3 mM KCl, 2 mM MgSO$_4$, 2 mM CaCl$_2$, and 14 mM dextrose, is adjusted to 313-320 mOsm and 7.4 pH, and bubbled with 93% 02/3% CO$_2$. The intracellular pipette solution contains 100 mM potassium gluconate, 20 mM KCl, 10 mM HEPES, 4 mM MgATP, 0.3 mM NaGTP, and 10 mM Na-phosphocreatine.

Intracellular Whole-Cell Recordings

Borosilicate pipettes (3-3 MΩ, WPI) are pulled using a Sutter P-80 puller (Sutter Instruments). Cells are visualized with an Achroplan 40× water-immersion lens with infrared-DIC optics (Zeiss) and detected with an infrared camera (Hamamatsu) projecting to a video monitor. Experiments are driven by custom acquisition and real-time analysis software written in Matlab (Mathworks, Natick, Mass.) using a Multiclamp 700B amplifier (Axon Instruments) connected to a BNC-2110 connector block and M-Series dual-channel acquisition card (National Instruments). Gigaseal and rupture is achieved and whole-cell recordings are continuously verified for low levels of leak and series resistance. For each recording, a 3 mV test pulse is applied in voltage clamp ~10 times to measure input and series resistance. Then in current clamp ~10 pulses (300 ms, 40-140 pA at 10 pA increments), are applied to quantify evoked firing rates and cellular excitability. Access resistance, leak, and cellular intrinsic excitability are verified to be consistent across groups. Finally, spontaneous EPSCs under voltage clamp at −60 mV are sampled at 10 kHz and low-pass filtered at 1 kHz. Analysis is performed using a custom software package written in Matlab, with all events detected according to automated thresholds and blindly verified for each event individually by the experimenter.

Golgi Staining

Samples (<1 cm) from P28 mice are fixed in 10% formalin and 3% potassium bichromate for 24 hours. Tissue is then transferred into 2% silver nitrate for 2 days in the dark at room temperature. Sections from these samples are then cut at 30 μm thickness into distilled water. Sections corresponding to motor cortex are mounted onto slides, air dried for 10 minutes, and then dehydrated through sequential rinses of 93% alcohol, 100% alcohol, and xylene, and then sealed with a coverslip. Images re acquired at 10× (whole cell) and 100× (spine imaging) using a Zeiss Pascal 3 Exciter confocal microscope.

Optical Imaging of Intrinsic Signals

Adult (>P60) wild type (SVEV or BL6) and MeCP2 (+/−) mutant females (BL6) are used for this experiment. The wild type control group is composed of both wild type littermates of MeCP2+/− females or wild type age matched SVEV females. For monocular deprivation, animals are anesthetized with Avertin (0.016 ml/g) and the eyelids of one eye is sutured for 4 days. Prior to imaging, the suture is removed and the deprived eye re-opened. Only animals in which the deprivation sutures are intact and the condition of the deprived eye appears healthy are used for the imaging session. For cG-2-AllylP signaling activation, a solution containing cG-2-AllylP is injected intra-peritoneally (IP) daily for the entire period of deprivation. For the imaging sessions mice are anesthetized with urethane (1.3 g/kg; 20% of the full dosage is administered IP each 20-minutes up to the final dosage, 0.02 ml of cloroprothixene 1% is also injected together with the first administration). The skull is exposed and a custom-made plate is glued on the head to minimize movement. The skull is thinned over VI with a dremel drill and covered with an agarose solution in saline (1.3%) and a glass coverslip. During the imaging session, the animal is constantly oxygenated, its temperature maintained with a heating blanket and the eyes periodically treated with silicone oil; physiological conditions are constantly monitored. The anesthetized mouse is placed in front of a monitor displaying a periodic stimulus presented to either eye, monocularly; the stimulus consisted of a drifting vertical or horizontal white bar of dimensions 9°×72°, drifting at 9 sec/cycle, over a uniformly gray background. The skull surface is illuminated with a red light (630 nm) and the change of luminance is captured by a CCD camera (Cascade 512B, Roper Scientific) at the rate of 15 frames/sec during each stimulus session of 23 minutes. A temporal high pass filter (133 frames) is employed to remove the slow signal noise, after which the signal is computer processed in order to extract, at each pixel, the temporal Fast Fourier Transform (FFT) component corresponding to the stimulus frequency. The FFT amplitude is used to measure the strength of the visual evoked response to each eye. The ocular dominance index is derived from each eye's response (R) at each pixel as ODI=(Rcontra−Ripsi)/(Rcontra+Ripsi). The binocular zone is defined as the region activated by the stimulation of the eye ipsilateral to the imaged hemisphere.

Heart Rate Measurements

Real time cardiac pulse rate is measured using a tail clip sensor (Mouse OX Oximeter-Oakmont, Pa.). Mice are not anesthetized but physically restrained in a fitted open plastic tube. Prior to the recording session the tube is placed overnight in the cages housing the experimental animals to allow habituation. Body temperature is maintained at ~82-84° F. throughout the recording time. We record 3 trials of 15 minutes for each mouse, mice are 8 weeks old and treated with vehicle or cG-2-AllylP from PIS.

Nocturnal Activity Measurements

Spontaneous motor activity is measured by using an infrared beam-activated movement-monitoring chamber (Opto-Varimax-MiniA; Columbus Instruments, Columbus, Ohio). For each experiment, a mouse is placed in the chamber at least 3 h before recordings started. Movement is monitored during the normal 12-h dark cycle (7 p.m. to 7 a.m.). One dark cycle per animal per time point is collected.

Results

To test whether cG-2-AllylP treatment will impact the development of cardinal features of the RTT disease, 2 week old mutant animals are given daily intra-peritoneal injections for the course of their lifespan. Measurements of synaptic physiology, synaptic molecular composition, and cortical plasticity are then acquired as detailed below, along with health-related measurements such as heart rate, locomotor activity levels, and lifespan.

Effects of cG-2-AllylP on the Synaptic Physiology of MeCP2 Mutant Mice

Recent studies have reported that neurons across multiple brain regions of MeCP2−/y mice display a profound reduction in spontaneous activity (Chang et al., 2006; Chao et al., 2007; Dani et al., 2005; Nelson et al., 2006) a phenotype that is rescued by over-expression of BDNF (Chang et al., 2006). Similarly, acute application of an IGF1 derivative has been shown to elevate evoked excitatory postsynaptic current (EPSC) amplitudes by 40% in rat hippocampal cultures (Ramsey et al., 2005; Xing et al., 2007). To test the efficacy of cG-2-AllylP in rescuing the MeCP2−/y physiological phenotype, we acquire intracellular whole cell recordings in acute brain slices, measuring excitatory synaptic drive (spontaneous EPSC amplitude and frequency) in layer 5 cortical neurons. Here, EPSCs recorded from –/y animals are significantly reduced in amplitude compared to EPSCs measured in wild-type animals. The trend is partially reversed in EPSCs recorded from MeCP2–/y animals treated with cG-2-AllylP, which are significantly larger in amplitude than EPSCs from MeCP2–/y mice treated with vehicle. These differences are also seen when averaging across cells. Throughout these measurements, access resistance, leak, and cellular intrinsic excitability are also verified to be consistent across groups. Quantifying EPSC intervals also shows a slight increase in the interval between EPSC events (reduced EPSC frequency) between wild-type and MeCP2–/y animals (P=0.04, Kolmogorov-Smirnov test). We find that the reduction of excitatory synaptic drive in cortical cells of MeCP2–/y mice, and its partial rescue following cG-2-AllylP treatment, are due in part to a change in EPSC amplitude as a consequence of a change in the strength of the synapses mediating excitatory transmission in this region.

cG-2-AllylP Treatment Stimulates Cortical Spine Maturation

We use Golgi staining to label neurons sparsely and distinctly, and applied high-resolution confocal imaging to measure dendritic spine density and morphology in the labelled cells, restricting analysis to layer 5 pyramidal neurons in sections of motor cortex from critical period mice (P28).

While low-magnification imaging clearly delineates the extent of the dendrites of the pyramidal cells we use higher magnifications to count synaptic contacts and determine the morphological class of each spine. We classify spines as either large and bulbous ("mushroom", M), short and stubby ("stubby", S), short and thin ("thin", T) or filopodia (F). Comparing the density of spines per unit branch exhibits a trend of decreased spine density in knockout neurons that is largely ameliorated in the knockout with treatment.

We find the potential for deficits in the number and maturational status of dendritic contacts in the knockout to underpin functional defects in excitatory transmission, in a manner that can be treated following administration of cG-2-AllylP.

Ocular Dominance (OD) Plasticity in Adult MeCP2+/– Mice is Reduced By cG-2-AllylP Developmental changes in OD plasticity are controlled in part by the activation of the IGF-1 pathway, and administration of (1-3)IGF-1 can reduce OD plasticity in wild type young mice (Tropea et al., 2006). We therefore test if cG-2-AllylP treatment could stabilize the prolonged OD plasticity observed in adult MeCP2 mutants. Female MeCP2+/– mice, aged P60 or more, are monocularly deprived for 4 days and treated concurrently with cG-2-AllylP. cG-2-AllylP treatment reduces the OD plasticity in the adult Mecp2+/– mice, indicating that indeed cG-2-AllylP can rapidly induce synapse stabilization or maturation.

Bradycardia in MeCP2–/y Mice is Treated by cG-2-AllylP

In addition to examining the efficacy of cG-2-AllylP in ameliorating neurophysiological symptoms, we seek to characterize its effects on the general health of the organism. Clinical and experimental evidence shows autonomic system dysfunctions such as labile breathing rhythms and reduced baseline cardiac vagal tone in Rett Syndrome patients (Julu et al., 2001). A poor control of the feedback mechanisms that regulate blood pressure homeostasis through the sympathetic system, for example hyperventilation-induced decrease in heart rate, is common in Rett Syndrome patients and can cause life threatening cardiac arrhythmias (Acampa and Guideri, 2006; Julu et al., 2001).

The pathogenesis of the cardiac dysautonomia, although not well understood, suggests that immature neuronal connections in the brainstem could be the cause. To examine heart rate abnormalities in MeCP2–/y mice and the effect of cG-2-AllylP treatment, we monitor real time cardiac pulse rate in non-anesthetized wild type and MeCP2–/y animals treated with vehicle or cG-2-AllylP. Wild type mice exhibit a regular distribution of heart rate measurements centred near 750 beats per minute. In contrast, MeCP2–/y mice exhibit a more irregular heart rate with a lower average rate, the occurrence of which is significantly reduced following treatment with cG-2-AllylP.

cG-2-AllylP Administration Improves Locomotor Activity and Life Span

MeCP2–/y mice develop Rett-like symptoms beginning at 4-6 weeks of age when they progressively become lethargic, develop gait ataxia and the between 10 and 12 weeks of age (Chen et al., 2001). Baseline locomotor activity is also recorded in mice after 6 weeks by counting nocturnal infrared beam crossing events within a caged area. MeCP2 knockout mice (KO) exhibits markedly reduced locomotor activity levels compared to wild-type mice (WT), but treatment with cG-2-AllylP (KO-T) elevates these levels.

Finally, compared to MeCP2 KO littermates, MeCP2–/y mice treated with cG-2-AllylP also show an increase in life expectancy.

We also measure the effect of cG-2-AllylP treatment on neuron soma size in the hippocampus. Mice are treated with cG-2-AllylP as described above for locomotor activity. Soma size in neurons in the CA3 region of the hippocampus is significantly impaired in MeCP2 KO animals relative to wild-type animals. cG-2-AllylP treatment increases average soma size in KO animals, but has little or no effect on soma size in wild type animals.

Example 22: Effect of Oral cG-2-AllylP on Survival in Rett Syndrome in Mice

Because Rett Syndrome is a chronic, debilitating disorder involving loss of motor skills, it is desirable to treat Rett Syndrome using easily administered preparations. To this end, we can take advantage of unexpectedly beneficial therapeutic and pharmacokinetic properties of cG-2-AllylP and related compounds (U.S. Pat. Nos. 7,776,876, and 8,067,425).

Therefore, we administer cG-2-AllylP orally to MeCP2 deficient mice. Briefly, an aqueous solution or other composition containing a pharmaceutically effective amount of cG-2-AllylP (20 or 80 mg/kg per animal) is administered daily. In control MeCP2 deficient animals, we administer saline only, and wild-type animals are used to obtain baseline data similar to the design.

In wild-type animals, survival is defined to be 100% at each time point. In MeCP2 deficient animals, survival is decreased substantially. However, after oral administration of cG-2-AllylP to MeCP2 deficient mice, survival is increased substantially.

Example 23: Effect of cG-2-AllylP on Seizure Activity in Rett Syndrome in Mice

Because seizures are a prominent, hazardous and a difficult to treat aspect of Rett Syndrome, we determine the effects of cG-2-AllylP on seizure activity in MeCP2 deficient animals.

Electroencephalograph: recordings of wild-type mice and MeCP2 deficient mice treated with either saline or cG-2-AllylP are obtained using methods described in U.S. Pat. No. 7,714,020, incorporated fully by reference.

We find that cG-2-AllylP can be effective in decreasing both motor seizures and non-convulsive seizures.

Conclusions cG-2-AllylP can be an effective therapy for treating human beings with Rett Syndrome. Moreover, because cG-2-AllylP has unexpectedly longer half life than a naturally occurring compound ((1-3) IGF-1; Glycyl-Prolyl-Glutamate or GPE), we find that use of cG-2-AllylP has distinct and substantial advantages over other pharmacological agents, including GPE.

For example, cG-2-AllylP need not be delivered intravenously, subcutaneously, intraventricularly, or parenterally. In fact, oral formulations comprising micro-emulsions, coarse emulsions, liquid crystal preparations, nanocapsules and hydrogels can be used in manufacture of orally administered preparations such as tablets, capsules and gels that can improve neurological function and treat neurodegenerative conditions. Compounds of this invention can be used in situations in which a patient's motor functioning is below that needed to swallow a table or capsule. There are several types of soluble gels for oral administration of compounds, and these can be used to deliver a compound or composition of this invention to a patient. Because cG-2-AllylP can be easily administered orally and is orally effective in treating neurodegenerative disorders, including Rett Syndrome, we conclude that cG-2-AllylP can be convenient and beneficial for long-term therapy of patients with Rett Syndrome.

Further, because Rett Syndrome shares key features with other autism spectrum disorders, compounds of this invention can be useful in providing therapeutic benefit from animals having other ASD, and in humans with autism, Asperger Syndrome, Childhood Disintegrative Disorder, and Pervasive Developmental Disorder-Not Otherwise Specified (PDD-NOS).

Example 24: Treatment of ASDs

There are several animal systems that have been used to evaluate therapeutic efficacy of compounds in ASDs.

Shank3-Deficient Mouse Model

Shank3-deficient mice are used in the study as a model of 22q13 deletion syndrome associated with ASD.

22q13 deletion syndrome has been linked with deletions or mutations in Shank3 gene (Bonaglia et al, 2006). The Shank3 gene codes for a master scaffolding protein which forms the framework in glutamatergic synapses (Boeckers et al, 2006). Shank3 is a crucial part of the core of the postsynaptic density (PSD) and recruits many key functional elements to the PSD and to the synapse, including components of the a-amino-3-hydroxyl-5-methyl-4-isoxazole-propionic acid (AMPA), metabotropic glutamate (mGlu), and N-methyl-D-aspartic acid (NMDA) glutamate receptors, as well as cytoskeletal dements. Recent studies exploring the rate of 22q13 deletions/Shank3 mutations suggest that haploinsufficiency of Shank3 can cause a monogenic form of ASD with a frequency of 0.3% to 1% of ASD cases (Durand et al, 2007; Moessner et al, 2007; Gauthier et al, 2008).

The generation of the mouse model with disrupted expression of full-length Shank3 has been previously described in the art (Bozdagi et al., Molecular Autism 2010, 1:13, p 4). Briefly, Bruce4 C37BL/6 embryonic stem cells were used to generate a mouse line that had loxP sites inserted before exon 4 and exon 9. The floxed allele was excised and a line was maintained with a deletion of exons 4 to 9, i.e. a complete deletion of the ankyrin repeat domains of Shank3. Wild-type (+/+), heterozygous (+/−) and knockout (−/−) mice were produced, with Mendelian frequencies from heterozygote-heterozygote crosses. A 30% reduction of full length Shank3 mRNA was confirmed in heterozygotes (qPCR) as well as a reduced expression of Shank3 protein (by immunoblotting with Skank3 antibody N69/46).

Heterozygous mice generated by crossing wild-type mice with heterozygotes are used in this example to best model the haploinsufficiency of Shank3, responsible for 22q13 deletion syndrome.

Methods

Drug Treatment 1 to 3 month old wild-type and heterozygous Shank3-deficient mice are divided into 4 treatment groups: placebo treated wild-type, placebo treated Shank3-deficient group and two Shank3-deficient cG-2-AllylP treated groups. The animals are given placebo (water) or cG-2-AllylP formulated in water administered orally, b.i.d for 14 days. cG-2-AllylP is administered at two doses: 15 or 60 mg/kg.

Methodology

A detailed description of the methodology can be found in Bozdagi et al. (Molecular Autism 2010, 1:15).

Behavioral Analyses

Behavioral assessments are made at several time points, and include analysis of social interactions and ultrasonic social communication, in line with the methodology described by Bozdagi et al. Briefly, male-female social interactions in each treatment group are evaluated. The subject males are group-housed and individually tested in clean cages with clean litter. Each testing session lasts 5 min. Each of the subject mice is paired with a different unfamiliar estrus C57BL/6J female. A digital closed circuit television camera (Panasonic, Secaucus, N.J., USA) is positioned horizontally 30 cm from the cage. An ultrasonic microphone (Avisoft UltraSoundGate condenser microphone capsule CM 15; Avisoft Bioacoustics, Berlin, Germany) is mounted 20 cm above the cage. Sampling frequency for the microphone is 250 kHz, and the resolution is 16 bits. While the equipment used cannot distinguish between calls emitted by the male subject and female partner, the preponderance of calls during male-female interactions in mice is usually emitted by the male. The entire apparatus is contained in a sound-attenuating environmental chamber (ENV-018V; Med Associates, St Albans, Vt., USA) illuminated by a single 25-Watt red light. Videos from the male subjects are subsequently scored by an investigator uninformed of the subject's genotype and treatment group on measures of nose-to-nose sniffing, nose-to-anogenital sniffing and sniffing of other body regions, using Noldus Observer software (Noldus Information Technology, Leesburg, Va., USA). Ultrasonic vocalizations are identified manually by two highly trained investigators blinded to genotype/treatment group information, and summary statistics are calculated using the Avisoft package. Interrater reliability is 95%. Data are analysed using an unpaired Student's t-test.

Olfactory habituation/dishabituation testing is conducted in male and female mice for each group. The methodology is as previously described (Silverman et al 2010, Yang et al 2009 and Silverman et al 2010). Non-social and social odors are presented on a series of cotton swabs inserted into the home cage sequentially, each for 2 min, in the following order; water, water, water (distilled water); almond, almond, almond (1:100 dilution almond extract); banana, banana, banana (1:100 dilution artificial banana flavouring); social 1, social 1, social 1 (swiped from the bottom of a cage housing unfamiliar sex-matched B6 mice); and social 2, social 2, social 2 (swiped from the bottom of a second cage housing a different group of unfamiliar sex-matched 129/SvImJ mice). One-way repeated measures ANOVA is performed within each treatment group for each set of habituation events and each dishabituation event, followed by a Tukey post hoc test.

Hippocampal Slice Electrophysiology

Post-mortem, acute hippocampal slices (350 µm) are prepared from mice using a tissue chopper. Slices are maintained and experiments are conducted at 32° C. Slices are perfused with Ringer's solution containing (in mM): NaCl, 125.0; KCl, 2.5; $MgSO_4$, 1.3; $NaH_2PO_4$, 1.0; $NaHCO_3$, 26.2; $CaCl_2$, 2.5; glucose, 11.0. The Ringer's solution is bubbled with 95% 02/5% CO2, at 32° C., during extracellular recordings (electrode solution: 3 M NaCl). Slices are maintained for 1 hr prior to establishment of a baseline of field excitatory postsynaptic potentials (fEPSPs) recorded from stratum radiatum in area CA1, evoked by stimulation of the Schaffer collateral-commissural afferents (100 µs pulses every 30 s) with bipolar tungsten electrodes placed into area CA3. Test stimulus intensity is adjusted to obtain fEPSPs with amplitudes that are one-half of the maximal response. The EPSP initial slope (mV/ms) is determined from the average waveform of four consecutive responses. Input-output (I/O) curves are generated by plotting the fEPSP slope versus fiber volley amplitude in low-$Mg^{2+}$ (0.1 mM) solution. AMPA receptor-mediated and NMDA receptor-mediated I/O relationships are measured in the presence of ionotropic glutamate receptor antagonists: 2-amino-2-phosphonopentanoic acid APV (50 µM) and 6-cyano-7-nitroquinoxaline-2,3-dione CNQX (100 µM). Paired-pulse responses are measured with interstimulus intervals of 10 to 200 ms, and are expressed as the ratio of the average responses to the second stimulation pulse to the first stimulation pulse.

LTP is induced either by a high-frequency stimulus (four trains of 100 Hz, 1 s stimulation separated by 5 min), or by theta-burst stimulation (TBS) (10 bursts of four pulses at 100 Hz separated by 200 ms), or by a single 100 Hz stimulation, for control and genetically-modified mice. To induce long-term depression (LTD), Schaffer collaterals are stimulated by a low frequency or paired-pulse low frequency stimulus (900 pulses at 1 Hz for 13 min) to induce mGlu receptor-dependent LTD. Data are expressed as means±SD, and statistical analyses are performed using analysis of variance (ANOVA) or student's t-test, with significance set at an a level of 0.03.

Results

Behavioral

Cumulative duration of total social sniffing by the male test subjects is lower in placebo treated Shank3-deficient group than in placebo treated wild-type group. In addition, fewer ultrasonic vocalizations are emitted by the placebo treated Shank3-deficient group than by the wild-type controls during the male-female social interactions.

cG-2-AllylP treatment in the two Shank3-deficient groups results in a significant increase in the cumulative duration of total social sniffing in comparison to the placebo treated Shank3-deficient group. Moreover, the cG-2-AllylP treated groups display an increased number of ultrasonic vocalizations than the placebo treated mutant group.

In the olfactory habituation/dishabituation study, intended to confirm that the mice are able to detect social pheromones, all 4 groups display normal levels of habituation (indicated by decreased time spent in sniffing the sequence of three same odors), and the expected dishabituation (indicated by increased spent in sniffing the different odor).

Electrophysiology

Plotting field excitatory postsynaptic potential (fEPSP) slope versus stimulus intensity demonstrates a reduction in the I/O curves in the placebo treated Shank3-deficient group versus the control group. In the heterozygous placebo treated group we also observe a decrease in AMPA receptor-mediated field potentials, reflected in a 30% decrease in the average slope of I/O function compared to the wild-type control group. In contrast, when the I/O relationship is analyzed in the presence of the competitive AMPA/kianate receptor antagonist CNQX to measure synaptic NMDA receptor function, there is no difference between the wild-type and placebo treated heterozygous groups. These results indicate that there is a specific reduction in AMPA receptor-mediated basal transmission in the Shank3 heterozygous mice.

cG-2-AllylP treatment in both heterozygous groups normalizes the AMPA receptor-mediated field potentials and causes an increase in the average slope of I/O function compared to the placebo treated Shank3-deficient group.

The maintenance of LTP in the placebo treated Shank3-deficient group is clearly impaired in comparison to the wild-type control. TBS LTP tests (10 bursts of four pulses at 100 Hz separated by 200 ms) also show a significant decrease in the potentiation at 60 min after TBS in the placebo treated Shank3-deficient group. In contrast to the altered synaptic plasticity observed with LTP, long-term depression (LTD) was not significantly changed in the mutant group. cG-2-AllylP treatment increases hippocampal long-term potentiation (LTP) and its maintenance in both Shank3-deficient group in comparison to the placebo treated Shank3-deficient group.

Discussion and Conclusions

Poor social competencies and repetitive behaviors are the common features and key diagnostic measures of all forms of ASD. Delayed intellectual development and underdeveloped language skills are also a common feature present in all ASD, excluding Asperger syndrome.

The animal models described above have been accepted in the art as demonstrating similar symptoms to the clinical human conditions. All mutant models discussed above (NLGN3, NLGN4, CADM1, NRXN1, FMR1, shank3) exhibit impaired social skills or increased social anxiety. Decreased excitatory transmission into the hippocampus has been identified in NRXN1, shank3, MeCP2 and FMR1 mutant animal models. At present no polygenetic or multifactorial models of ASD have been described. The animal models described above, based on genetic defects that are known to produce ASD in human population, provide the best opportunity to test the efficacy of ASD therapies.

Therefore the efficacy of cG-2-AllylP in animal models of ASD is reasonably predictive of its efficacy in a human subject suffering from ASD.

Example 25: Measurement of the Signaling Proteins Phospho-ERK1/2 and Phospho-Akt by Phospho-Flow Cytometry Analysis of FXS Mice Lymphocytes Signal transduction pathways link external stimuli with cellular responses, which normally regulate cell proliferation, death, and differentiation. We use phospho-specific antibodies for ERK1/2 and Akt that recognize these proteins only when they are phosphorylated. One of the unique features of flow cytometry is its ability to perform measurements of phosphorylation states at the that is not obtained by standard biochemical techniques this clearly has wide potential for studying drug treatment effect.

Methods

Lymphocytes are isolated from five fmr1-knockout and five wild-type titter mate control mice, per study time after injection with cG-2-AllylP. Lymphocytes are examined for activation of two signaling effectors, p-ERK1/2 and p-Akt using phosphorylation status as a measure of activation by flow cytometry (phospho-flow).

Measures taken are:

1. Flow cytometry total and phosphorylated ERK in lymphocytes

2. Flow cytometry total and phosphorylated AKT in lymphocytes

Results

We find that lymphocytes isolated from fmr1-knockout mice exhibit activation of ERK1/2 and Akt phospho-epitopes. The mean fluorescent intensity (MFI) levels for p-AKT and p-ERK1/2 in fmr1-knockout mice treated with cG-2-AllylP decreases at all time points: 15, 30, 60 and 240 minutes after a single treatment. We find similar reductions of MFI in fmr1-knockout mice after 5 and consecutive days of cG-2-AllylP treatment.

In summary, cG-2-AllylP produces a significant reduction in phospho activation of ERK1/2 and Akt in fmr1-knockout mice. This result indicates that p-ERK and p-Akt are useful biological markers to assess therapeutic efficacy in treating human beings with ASD or NDD. Because expression of pERK and pAkt in lymphocytes are similar to expression of those phosphorylated proteins in brains of fmr1-knockout mice, observation of therapeutic effects in lymphocytes is reasonably predictive of effects of cG-2-AllylP in the brains of affected animals, including human beings.

Example 26: Treatment of Human Beings Having Fragile X Syndrome Using G-2-AllylP To determine whether cG-2-AllylP is effective in treating patients with fragile X Syndrome, we carry out a double-blinded, placebo-controlled study.

Methods

Patients

Male patients having Fragile X Syndrome are diagnosed by genetic analysis demonstrating full fmr1 mutation. Symptoms are evaluated using one or more of the clinical evaluative tools discussed herein above. Each patient is scored according to one or more clinical evaluative tool for one or more of Repetitive Behavior (RBB), Anxiety, and Sociability. A Clinical Global Impression-Severity (CGI-S) score of 4 or greater, or an ABC total score of 30 or greater are enrolled.

Drug Delivery

The enrolled patients are divided into groups. All enrollees commence the study with a 2-week single-blind administration of placebo b.i.d. Thereafter, cG-2-AllylP is administered orally at a dose of 35 mg/kg b.i.d. (n=20) or 70 mg/kg b.i.d (n=20) for 28 days, followed by 28 days of placebo, or if randomized to placebo, cG-2-AllylP is administered at a dose of 70 mg/kg b.i.d. starting on day 42 and ceasing on day 70. Prior to dispensing study medication, cG-2-AllylP is reconstituted with a strawberry flavored diluent to provide a liquid for oral administration. Placebo (n=20) is strawberry diluent and water.

Assessments

Pharmacokinetics

Blood samples from all subjects in each group are taken at Day 42 and Day 70. Four (4) samples are collected commencing on Day 42 (pre-dose and 2-4 hours post dose) and Day 70 (pre-dose and 2-4 hours post dose). A back-up sample for each time point is also collected.

Efficacy

Efficacy is determined using Clinical Global Impression of Severity (CGI-S), Clinical Global Impression of Improvement (CGI-I), Fragile X Syndrome Rating Scale, clinician-completed Fragile X Domain Specific Concerns (Visual Analog Scale), Caregiver Top Three Concerns (Visual Analogue Scale), Aberrant Behavior Checklist, Vineland Adaptive Behavior Scale, CASI-16, CYBOCS-PDD, seizure diary, computerized eye tracking, computerized measurement of cognition using the KiTap, and the Expressive Language Sampling Task.

Efficacy Outcome Measures

The following four groups of efficacy outcome measures are evaluated, comparing two dosage levels of cG-2-AllylP, separately and combined, with placebo.

Global Functional Outcome Measures

The following measures are assessed at Baseline, and during treatment and the changes compared between active and placebo groups.

Changes in the Fragile X Syndrome Rating Scale are calculated for each subject between Baseline (pre-treatment) Day 14, and end of treatment (Days 42 and 70).

Global outcome is measured by the Clinical Global Impression-Severity and Improvement scales (CGI-S and CGI-I) at each clinic visit, from Baseline onwards (e.g. Days 14, 28, 42, 56, 70, and 84.

Changes in the clinician-completed fragile X Domain Specific Concerns, as captured via a Visual Analog Scale (VAS), is calculated for each subject between Baseline (pre-treatment), Day 14, and end of treatment (Days 42 and 70).

Changes in Caregiver Top Three Concerns (related to the subject's Fragile X syndrome) as captured via a Visual Analogue Scale (VAS) is calculated within subjects between Baseline (pre-treatment). Day 14, and end of treatment (Days 42 and 70).

Changes in the CASI-16, CYBOCS-PDD, Aberrant Behavior Checklist (ABC), Expressive Language Sampling Task and Vineland Adaptive Behavior Scales (VABS) is calculated for each subject between Baseline, Day 14, and Days 42, and 70.

Physiological Outcome Measures

Serum levels and changes of standard hematology and chemistry parameters (including thyroid function) are calculated from Baseline through to Day 70. Fundoscopy and tonsil size is documented at Baseline, and Days 14, 28, 42, 36, 70 and 84. Flow cytometry is used to assess the phosphorylation status of the enzymes Akt and ERK in peripheral lymphocytes, on blood samples obtained on Days 14, 28, 42, 36, and 70. ECG is assessed at Screening, Baseline, Days 28, 42, 36 and 70.

Cognitive/Automated Outcome Measures

The following measures are assessed at Baseline, during and post study drug administration. Computerized measurement of cognition using the KiTap, is assessed at Baseline, Day 14, Day 42, Day 70 and Day 84. Computer-based eye tracking assessment is measured at Baseline, Day 14, 28, 42, 36 and Day 70.

Pharmacokinetic-Pharmacodynamic Relationships

Matched pharmacokinetic (PK) and efficacy (PD) measures are collected from all patients randomized to receive either 35 mg/kg or 70 mg/kg oral cG-2-AllylP twice daily.

The pharmacodynamic markers include Global Functional, Physiological and Cognitive/Automated Outcomes. The approach is to assess changes in efficacy measures over the course of the study and to correlate these with measured or calculated pharmacokinetic endpoints. In addition PK/PD models are used to establish a relationship between blood concentration of cG-2-AllylP and effect, where appropriate.

Statistical Methods

Efficacy

ANOVA, ANCOVA and Chi-square tests are used to compare efficacy measure levels and changes between treatment groups. Each dose group is compared with the concurrent placebo group and the combined dose group is compared with the combined placebo group. A two tailed p-value <0.05 is considered to indicate statistical significance.

A total sample size of 60 (40:20) enables effect sizes >0.80 between active and placebois detected as statistically significant (2-tailed α=0.05) with 80% power on key outcome measures such as the Fragile X Syndrome Rating Scale. For comparisons within each dose group (i.e. comparison of assessment times), effect sizes >0.7 within active and placebo are detected as statistically significant (2-tailed α=0.05) with 80% power.

Pharmacokinetics

The maximal concentration (Cmax; peak), minimum concentration (Cmin; trough), C0-4 and area under the curve (AUC) parameters at steady state are calculated directly from the cG-2-AllylP concentration data and summarized at each time point using standard descriptive statistics including means, medians, geometric means, standard deviations, ranges, and 95% confidence intervals.

In order to determine whether there are associations between PK parameters and efficacy measures, the changes in efficacy measures over the course of the study are correlated with PK parameters estimated at the different time points. These associations are statistically tested using correlation coefficients and general linear models.

Results and Conclusion

We find that cG-2-AllylP is well tolerated by the patients. We further find that cG-2-AllylP has clinically relevant and significant effects to improve clinical outcomes as measured using one or more evaluative tools described herein. We also find that cG-2-AllylP normalizes pERK and pAkt levels.

This study demonstrates that of cG-2-AllylP is effective in treating adverse symptoms of Fragile X Syndrome in human beings.

Example 26: Effects of cG-2-AllylP on Synaptic Plasticity Following Penetrating Ballistic-Like Brain Injury in Rats I In this Example, we investigated whether cG-2-AllylP has anti-inflammatory and anti-apoptotic activity after Penetrating Ballistic-Like Brain Injury (PBBI). Molecules structured similarly to cG-2-AllylP have been shown to have memory enhancing effects or improve passive-avoidance learning in vivo and promote neurite outgrowth in vitro. This suggests that treatment with c(GP) analogues enhances neuroplasticity and synapse formation. We therefore investigated whether cG-2-AllylP regulates genes and encoded proteins that govern synaptic plasticity following PBBI.

Methods

Penetrating Ballistic-Like Brain Injury (PBBI)

The unilateral frontal PBBI model, which mimics the ballistic dynamics of a bullet or fragment wound to the head (Williams, 2003; Williams, 2006), was induced by stereotactic insertion of a custom probe through the right frontal cortex. A temporary cavity was formed by the rapid inflation/deflation (i.e. <40 msec) of an elastic balloon attached to the end of the probe. The PBBI apparatus consisted of a computer-controlled hydraulic pressure generator (Mitre Corp McLean, Va.), a PBBI probe and a stereotaxic frame equipped with a custom-designed probe holder as previously described (Lu, 2009; Williams, 2003). The injury severity was determined by the size of the balloon under control of the computerized hydraulic pressure. The balloon diameter calibrated to 0.63 cm expansion represented 10% of the total rat brain volume thus expressing a 10% PBBI. All surgeries were done under anaesthesia. Groups tested: Sham+vehicle, PBBI+vehicle, PBBI+cG-2-AllylP (30 mg/kg by oral gavage, 30 min post-injury, and again once daily until endpoint). AU procedures were approved by the Institutional Animal Care and Use Committee of WRAIR. Animals were housed in a facility accredited by the AAALAC.

Oral Administration of cG-2-AllylP cG-2-AllylP (or vehicle) was administered to the animals via oral gavage at a dose of 30 mg/kg.

ELISA

Target proteins were quantified with interleukin 1 beta ("IL-1beta") (GenWay Biotech GWB-SKR107) and interleukin-6 ("IL-6") (GenWay Biotech GWB-ZZD100) ELISAs according to manufacturer's instructions. Levels were calculated and normalized to total protein concentration as determined by BCA assay (n=9-10 per group).

Western Blotting

Samples were analysed at 24 hr and 3 and 7 days post-injury for all groups (sham+vehicle, PBBI+vehicle, PBBI+cG-2-AllylP). Tissue was homogenized in RIPA buffer containing HALT protease inhibitors. Total protein was based on BCA assay. Blots were blocked 5% milk, probed with anti-ATF3, anti-BAX, or anti-BCL2. Blots were re-probed with anti-beta-actin antibody to control for protein loading. Analysis of band intensity was done using an LAS4000 and ImageQuantTL software (GE Healthcare) (n=9-10 per group).

Neuroplasticity mRNA Arrays cDNA was generated. From total RNA from individual animals using random primers. cDNA was plated unto a targeted PCR array produced by SA Biosciences and product was detected using SyBr green fluorescence. Ct levels were normalized to beta actin. Injury results were compared to sham to evaluate relative quantities (RQ) (n=6 per group).

Results

PBBI injury alone led to an acute (at 24 hrs. after PBBI) increase in the inflammatory and apoptotic measures studied. FIG. 33A-33F shows these results. PBBI increased the amount of IL-1beta (FIG. 33A) and IL-6 (FIG. 33D). cG-2-AllylP decreased proinflammatory cytokines IL1-beta (FIG. 33C) and IL-6 (FIGS. 33D and 33F). ANOVA: * p<0.05, ** p<0.01; Error bar: SEM. cG-2-AllylP increased IL1-beta levels at 3 days after PBBI, which may be compensatory for its downstream target IL-6. Treatment with cG-2-AllylP decreased levels of IL1-beta at 7 days after PBBI (FIG. 33C). cG-2-AllylP treatment decreased IL-6 levels at both 24 hrs. (FIG. 33D). and 7 days (FIG. 33E) after PBBI, but had little effect at 3 days (FIG. 33B). These results indicate that cG-2-AllylP reduced these inflammatory cytokines.

FIG. 34 shows that PBBI significantly and substantially increased expression of BAX (FIGS. 34 A, 34B, and 34C) and BCL2 (FIGS. 34D, 34E, 34F, 34G, and 34H). cG-2-AllylP did not significantly alter BAX (FIGS. 34A-34C) or BCL2 (FIGS. 34D-34H) levels.

FIG. 35 shows that PBBI increased expression of ATF3 at all time points (FIGS. 35A-35C). Surprisingly, we found that cG-2-AllylP decreased ATF3 at 24 hrs. after PBBI as measured globally by Western blotting (FIG. 35A).

FIG. 36 shows that after PBBI, cG-2-AllylP treatment significantly increased Gria 4 (an AMPA receptor, FIG. 36F) at the 24 hr. time point. In addition, we observed trends including: decreased Crem (a CREB inhibitor, FIG. 36D), decreased NTF3 (FIG. 36J), decreased NTF4 (FIG. 36K), decreased Pcdh8 (a tumor suppressor gene; FIG. 36L), decreased BDNF (FIG. 36A), decreased Pim1; FIG. 36M) and increased Ppp3ca (FIG. 36N).

Conclusions

These trends in RNA expression, particularly the increased Gria 4, decreased Crem, and decreased Pcdh8 expression promote neuroplasticity. The decreased NTF3 and NTF4 allows synaptic formation.

Collectively, these results indicate that cG-2-AllylP has anti-inflammatory effects following severe PBBI and enhanced neuroplasticity. Because the results obtained in this experimental system are reasonably predictive of effects seen in human beings, cG-2-AllylP and similar cyclic GP compounds can be effective in treating symptoms of mild, moderate, or severe traumatic brain injury.

Example 27: Effects of cG-2-AllylP on Synaptic Plasticity Following Penetrating Ballistic-Like Brain Injury in Rats II: Growth-Associated Protein 43 and Synaptophysin In this Example, we examined the role of cG-2-AllylP on expression of genes and proteins related involved in neuroplasticity following penetrating ballistic-like brain injury (PBBI; 10% injury severity) in rats.

Methods

The methods for producing PBBI in this Example is the same as described above for Example 26. Adult Sprague-Dawley rats were randomly assigned into three groups: sham (craniotomy only), PBBI+vehicle (i.e. $H_2O$), and PBBI+cG-2-AllylP. cG-2-AllylP (or vehicle) was administered via oral gavage at 30 mg/kg at 30 min post-injury and continued once daily thereafter for 7, 14 or 28 days. At each treatment endpoint, rats were perfused and brains were processed for histological analysis (n=5-6/group/timepoint). For detection of axonal sprouting, immunohistochemical detection of growth-associated protein-43 (GAP-43) was employed. Synaptogenesis was determined by immunohistochemistry for synaptophysin (SYN). For histological quantification, the integrated density in the hippocampal region was determined using NIH ImageJ software.

Results

In the vehicle treatment group, PBBI significantly decreased GAP-43 expression in the ipsilateral hippocampus at 7d, 14d and 28d post-injury, and in the contralateral hippocampus at 7d and 14d post-injury (p<0.05 vs. sham). Significant reductions in SYN staining were detected at 14d and 28d post-injury in the ipsilateral hippocampus and at 14d post-injury in the contralateral hippocampus in the PBBI+vehicle group (p<0.03 vs. sham). Continuous treatment with cG-2-AllylP showed no effect on injury-induced reductions in GAP-43 or SYN expression at 7d or 14d post-PBBI. However, at 28 days post-injury, cG-2-AllylP treatment attenuated PBBI-induced reductions in both GAP-43 and SYN expression to levels that did not differ significantly from sham controls, indicative of an intermediate treatment effect.

CONCLUSIONS

Histological analysis indicates that PBBI induced significant reduction of axonal sprouting and synaptogenesis during sub-acute to chronic phase after injury. These results show a trend of cG-2-AllylP in promoting neuroplasticity. Because the animal system used is predictive of neuroplasticity in human beings, these results indicate that cG-2-AllylP can be effective in ameliorating adverse effects of brain injury.

The descriptions and examples provided herein are for purposes of illustration only. The scope of this invention to is not intended to be limited to the described embodiments. Other embodiments incorporating elements of the invention can be practiced without undue experimentation by persons of ordinary skill in the art. All such embodiments are therefore considered to be part of this invention.

REFERENCES

The following references, and all patents, patent applications and other publications cited herein are incorporated fully by reference as if separately so incorporated.

Alarcon, M., Abrahams, B. S., Stone J. L., Duvall J. A., Perederiy J. V., Bomar J. M., Sebat J., Wigler, M., Martin, C. L., Ledbetter, D. H., Nelson, S. F., Cantor, R. M., and Geschwind, D. H. (2008). Linkage, association, and gene-expression analyses identify CNTNAP2 as an autism-susceptibility gene. Am. J. Hum. Genet. 82, 150-159.

Amir R E, Van den Veyver I B, Wan M, Tran C Q, Francke U, Zoghbi H Y. Rett syndrome is caused by mutations in X-linked MECP2, encoding methyl-CpG-binding protein 2. Nat Genet 1999 23:185-188.

Andari E, Duhamel J R, Zalla T, Herbrecht E, Leboyer M, Sirigu A. (2010) Promoting social behavior with oxytocin in high-functioning autism spectrum disorders. PNAS 107:4389-4394.

Arking, D. E., Cutler, D J., Brune, C. W., Teslovich, T. M., West, K., Ikeda, M., Rea, A., Guy, M., Lin, S., Cook, E. H., and Chakravarti, A. (2008). A common genetic variant in the neurexin superfamily member CNTNAP2 increases familial risk of autism. Am. J. Hum. Genet. 82, 160-164.

Bakkaloglu, B., O'Roak, B. J., Louvi, A., Gupta, A. R., Abelson, J. F., Morgan, T. M., Chawarska, K., Klin, A., Ercan-Sencicek, A. G., Stillman, A. A., Tanriover, G., Abrahams, B. S., Duvall, J. A., Robbins, E. M., Geschwind, D. H., Biederer, T., Gunel, M., Lifton, R. P., and State M W (2008). Molecular cytogenetic analysis and resequencing of contactin associated protein-like 2 in autism spectrum disorders.

Bakkaloglu, B., O'Roak, B J., Louvi, A., Gupta, A. R., Abelson, J. F., Morgan, T. M., Chawarska, K., Klin, A., Ercan-Sencicek, A. G., Stillman, A. A., Tanriover, G., Abrahams, B. S., Duvall, J. A., Robbins, E. M., Geschwind, D. H., Biederer, T., Gunel, M., Lifton, R. P., and State M W (2008). Molecular cytogenetic analysis and resequencing of contactin associated protein-like 2 in autism spectrum disorders. Am. J. Hum. Genet. 82, 165-173.

Baron-Cohen S, Wheelwright S, Hill J, Raste Y. Plumb I (2001) The "Reading the Mind in the Eyes" test, revised version: A study with normal adults, and adults with Asperger's syndrome or high-functioning autism. J Child Psychol Psychiatry 42:241-251.

Belichenko P V, Oldfors A, Hagberg B, Dahlström A. Rett syndrome: 3-D confocal microscopy of cortical pyramidal dendrites and afferents. Neuroreport. 19945:1509-1513.

Biederer T, Sara Y, Mozhayeva M, Atasoy D, Liu X, Kavalali E T, Südhof T C. (2002) SynCAM, a synaptic adhesion molecule that drives synapse assembly. Science 297(5586): 1525-1531.

Chapleau C A, Larimore J L, Theibert A, Pozzo-Miller L. (2009) Modulation of dendritic spine development and plasticity by BDNF and vesicular trafficking: fundamental roles in neurodevelopmental disorders associated with mental retardation and autism. J. Neurodev. Disord. 1:185-196.

Cheng C M, Mervis R F, Niu S L, Salem N Jr, Witters L A, Tseng V, Reinhardt R, Bondy C A. Insulin-like growth factor 1 is essential for normal dendritic growth. J Neurosci Res. 2003 73:1-9.

Comery T A, Harris J B, Willems P J, Oostra B A, Irwin S A, Weiler U, Greenough W T. (1997) Abnormal dendritic spines in fragile X knockout mice: maturation and pruning deficits. Proc. Natl Acad. Sci. USA 94: 5401-5404.

Durand C M, Betancur C, Boeckers T M, Bockmann J, Chaste P, Fauchereau F, Nygren G, Rastam M, Gillberg I C, Anckarsäter H, Sponheim E, Goubran-Botros H, Delorme R, Chabane N, Mouren-Simeoni M C, de Mas P, Bieth E, Rogé B, Héron D, Burglen L, Gillberg C, Leboyer M, Bourgeron T. (2007) Mutations in the gene encoding the synaptic scaffolding protein SHANK3 are associated with autism spectrum disorders. Nat Genet. 39:25-27.

Etherton M R, Blaiss C A, Powell C M, Südhof T C. (2009) Mouse neurexin-1a deletion causes correlated electrophysiological and behavioural changes consistent with cognitive impairments. Proc. Nat. Acad. Sci. 106:17998-18003.

Garbern, J. Y., Neumann, M., Trojanowski, J. Q., Lee, V. M., Feldman, G., Norris, J. W., Friez, M J., Schwartz, C. E., Stevenson, R., and Sima, A. A. (2010). A mutation affecting the sodium/proton exchanger, SLC9A6, causes mental retardation with tau deposition. Brain 133, 1391-1402.

Gauthier J, Bonnel A, St-Ongc J, Karemera L, Laurent S, Mottron L, Fombonne E, Joober R, Rouleau G A. (2005) NLGN3/NLGN4 gene mutations are not responsible for autism in the Quebec population. Am. J. Med. Genet. B. Neuropsychiatr. Genet. 132B(1): 74-75.

Gilfillan, G. D., Selmer, K. K., Roxrud, I., Smith, R., Kyllerman, M., Eiklid, K., Kroken, M., Matdngsdal, M., Egeland, T., Stenmark, H., Sjoholm, H., Server, A., Samuelsson, L., Christianson, A., Tarpey, P., Whibley, A., Stratton, M. R., Futreal, P. A., Teague, J., Edkins, S., Gecz, J., Turner, G., Raymond, F. L., Schwartz, C., Stevenson, R. E., Undlien, D. E., and Stromme, P. (2008). SLC9A6 mutations cause X-linked mental retardation, microcephaly, epilepsy, and ataxia, a phenotype mimicking Angelman syndrome. Am. J. Hum. Genet. 82, 1003-1010.

Gilman S R, Iossifov I, Levy D, Ronemus M, Wigler M, Vitkup D. Rare de novo variants associated with autism implicate a large functional network of genes involved in formation and function of synapses. Neuron. 2011 70:898-907.

Giza J, Urbanski M J, Preston F, Bandyopadhyay B, Yam A, Friedrich V, Kelley K, D'Angelo E, Goldfarb M. (2010) Behavioural and cerebellar transmission deficits in mice lacking autism-linked gene Islet Brain-2. J. Neurosci. 30:14803-14816.

Guastella A J, Einfeld S L, Gray K M, Rinehart N J, Tonge B J, Lambert T J, Hickie I B. (2010) Intranasal oxytocin improves emotion recognition for youth with autism spectrum disorders. Biol Psychiatry. 67:692-694.

Hagerman R, Hoem G, Hagerman P. (2010) Fragile X and autism: Intertwined at the molecular level leading to targeted treatments. Mol. Autism 1:12-24.

Harris S W, Hessl D, Goodlin-Jones B, Ferranti J, Bacalman S, Barbato L Tassone F, Hagerman P J, Herman H, Hagerman R J. (2008) Autism profiles of males with fragile X syndrome. Am J Ment Retard. 113:427-438.

Hiramoto T, Kang G, Suzuki G, Satoh Y, Kucheriapad R, Watanabe Y, Hiroi N. (2011) Tbx1: identification of a 22q11.2 gene as a risk factor for autism spectrum disorder in a mouse model. Hum Mol Genet. 2011 20:4775-4785.

Hutsler J J, Zhang H. Increased dendritic spine densities on cortical projection neurons in autism spectrum disorders. Brain Res. 2010 1309:83-94.

Irwin S A, Galvez R, Greenough W T. Dendritic spine structural anomalies in fragile-X mental retardation syndrome. Cereb Cortex. 2000 10:1038-1044.

Jamain S, Quach H, Betancur C, Råstam M, Colineaux C, Gillberg I C, Soderstrom H, Giros B, Leboyer M, Gillberg C, Bourgeron T; Paris Autism Research International Sibpair Study. (2003) Mutations of the X-linked genes encoding neuroligins NLGN3 and NLGN4 are associated with autism. Nat. Genet. 34: 27-29.

Jamain S, Radyushkin K, Hammerschmidt K, Granon S, Boredus S, Varoqueaux F, Ramanantsoa N, Gallego J, Ronnenberg A, Winter D, Frahm J, Fischer J, Bourgeron T, Ehrenieich H, Brose N. (2008) Reduced social interaction and ultrasonic communication in a mouse model of monogenic heritable autism. Proc. Nat. Acad. Sci. 10S: 1710-1713.

Kim H G, Kishikawa S, Higgins A W, Seong I S, Donovan D J, Shen Y, Lally E, Weiss L A, Najm J, Kutsche K, Descartes M, Holt L, Braddock S, Troxell R, Kaplan L, Volkmar F, Klin A, Tsatsanis K, Harris D J, Noens I, Pauls D L, Daly M J, MacDonald M E, Morton C C, Quade B J, Gusella J F. (2008) Disruption of neurexin 1 associated with autism spectrum disorder. Am. J. Hum. Genet. 82:199-207.

Klemmer P, Meredith R M, Holmgren C D, Klychnikov O I, Stahl-Zeng J, Loos M, van der Schors R C, Wortel J, de Wit H, Spijker S, Rotaru D C, Mansvelder H D, Smit A B, Li K W. Proteomics, ultrastructure, and physiology of hippocampal synapses in a fragile X syndrome mouse model reveal presynaptic phenotype. J Biol Chem. 2011 286:23493-23304.

Krueger D D, Osterweil E K, Chen S P, Tye L D, Bear M F. (2011) Cognitive dysfunction and prefrontal synaptic abnormalities in a mouse model of fragile X syndrome. Proc. Natl Acad. Sci. USA 108: 2587-2592.

Lauterborn J C, Rex C S, Kramár E, Chen L Y, Pandyarajan V, Lynch G, Gall C M. (2007) Brain-derived neurotrophic factor rescues synaptic plasticity in a mouse model of fragile X syndrome. J. Neurosci. 27: 10683-10694.

Lintas C, Persico A M. (2009) Autistic phenotypes and genetic testing: state-of-the-art for the clinical geneticist. J. Med. Genet. 46:1-8.

Makkonen I, Kokki H, Kuikka J, Turpeinen U. Riikonen R. Effects of fluoxetine treatment on striatal dopamine transporter binding and cerebrospinal fluid insulin-like growth factor-1 in children with autism. Neuropediatrics. 2011 42:207-209.

Marchetto et al. (2010) A model for neural development and treatment of Rett syndrome using human induced pluripotent stem cells. Cell 143:527-539 (inch supplemental information).

Marshall C R, Noor A, Vincent J B, Lionel A C, Feuk L, Skaug J, Shago M, Moessner R, Pinto D, Ren Y, Thiruvahindrapduram B, Fiebig A, Schreiber S, Friedman J, Ketelaars C E, Vos Y J, Ficicioglu C, Kirkpatrick S, Nicolson R, Sloman L, Summers A, Gibbons C A, Teebi A, Chitayat D, Weksberg R, Thompson A, Vardy C, Crosbie V, Luscombe S, Baatjes R, Zwaigenbaum L, Roberts W, Fernandez B, Szatmari P, Scherer S W. (2008) Structural variation of chromosomes in autism spectrum disorder. Am J Hum Genet. 82:477-488.

Minshew N J, Williams D L. The new neurobiology of autism: cortex, connectivity, and neuronal organization. Arch Neurol. 2007 64:945-950.

Moessner R, Marshall C R. Sutcliffe J S, Skaug J, Pinto D, Vincent J, Zwaigenbaum L, Fenandez B, Roberts W, Szatmari P, Scherer S W. (2007) Contribution of SHANK3 mutations to autism spectrum disorder. Am. J. Hum. Genetics 81:1289-1297.

Moretti P, Levenson J M, Battaglia F, Atkinson R, Teague R, Antalffy B, Armstrong D, Arancio O, Sweatt J D, Zoghbi H Y. (2006) Learning and memory and synaptic plasticity are impaired in a mouse model of Rett syndrome. J. Neurosci. 26: 319-327.

Paylor, R., Glaser, B., Mupo, A., Ataliotis, P., Spencer, C., Sobotka, A., Sparks, C., Choi, C. H., Oghalai, J., Curran, S., Murphy, K. C., Monks, S., Williams, N., O'Donovan, M. C., Owen, M J., Scambler, P J., and Lindsay, E. (2006). PNAS 103, 7729-7734.

Penagarikano, O., Abrahams, B. S., Herman, E. I., Winden, K. D., Gdalyahu, A., Dong, H., Sonnenblick, L. I., Gruver, R., Almajano, J., Bragin, A., Golshani, P., Trachtenberg, J. T., Peles, E., and Geschwind, D. H. (2011). Absence of CNTNAP2 Leads to Epilepsy, Neuronal Migration Abnormalities, and Core Autism-Related Deficits. Cell 147, 235-246.

Riikonen R, Makkonen I, Vanhala R, Turpeinen U, Kuikka J, Kokki H. (2006) Cerebrospinal fluid insulin-like growth factors IGF-1 and IGF-2 in infantile autism. Dev. Med. Child Neurol. 48: 751-755.

Sebat J, Lakshmi B, Malhotra D, Troge J, Lese-Martin C, Walsh T, Yamrom B, Yoon S, Krasnitz A, Kendall J, Leotta A, Pai D, Zhang R, Lee Y H, Hicks J, Spence S J, Lee A T, Puura K, Lehtimäki T, Ledbetter D, Gregersen P K, Bregman J, Sutcliffe J S, Jobanputra V, Chung W, Warburton D, King M C, Skuse D, Geschwind D H, Gilliam T C, Ye K, Wigler M. (2007) Strong association of de novo copy number variation mutations with autism. Science 316(5823): 445-449.

Schaevitz L R, Moriuchi J M, Nag N, Mellot T J, Berger-Sweeney J. (2010) Cognitive and social functions and growth factors in a mouse model of Rett syndrome. Physiol. Behav. 100: 255-263.

Schütt J, Falley K, Richter D, Kreienkamp H J, Kindler S. (2009) Fragile X mental retardation protein regulates the levels of scaffold proteins and glutamate receptors in postsynaptic densities. J. Biol. Chem. 284: 25479-25487.

Silverman J L, Turner S M, Barkan C L, Tolu S S, Saxena R, Hung A Y, Sheng M, Crawley J N: Sociability and motor functions in Shank1 mutant mice. Brain Res 2010.

Silverman J L, Yang M, Lord C, Crawley J N: Behavioural phenotyping assays for mouse models of autism. Nat Rev Neurosci 2010, 11:490-502.

Spence S J, Schneider M T. The role of epilepsy and epileptiform EEGs in autism spectrum disorders. Pediatr Res. 2009 65:599-606.

Spencer C M, Alekseyenko O, Serysheva E, Yuva-Paylor L A, Paylor R. (2005) Altered anxiety-related and social behaviors in the Fmr1 knockout mouse model of fragile X syndrome. Genes Brain Behav. 4: 420-430.

Strauss, K. A., Puffenberger, E. G., Huentelman, M J., Gottlieb, S., Dobrin, S. E., Parod, J. M., Stephan, D. A., and Morton, D. H. (2006). Recessive symptomatic focal epilepsy and mutant contactin-associated protein-like 2. N. Engl. J. Med. 354, 1370-1377.

Stromme, P., Dobrenis, K., Sillitoe, R. V., Gulinello, M., Ali, N. F., Davidson, C., Micsenyi, M. C., Stephney, G., Ellevog, L., Klungland, A., and Walkley, S. U. (2011). X-linked Angelman-like syndrome caused by Slc9a6 knockout in mice exhibits evidence of endosomal-lysosomal dysfunction. Brain. 134:3369-3383.

Sykes N H, Toma C, Wilson N, Volpi E V, Sousa I, Pagnamenta A T, Tancredi R, Battaglia A, Maestrini E, Bailey A J, Monaco A P; International Molecular Genetic Study of Autism Consortium (IMGSAC). (2009) Copy number variation and association analysis of SHANK3 as a candidate gene for autism in the IMGSAC collection. Eur. J. Hum. Genet. 17:1347-1353.

Tabuchi K, Blundell J, Etherton M R, Hammer R E, Liu X, Powell C M, Südhof T C. (2007) A neuroligin-3 mutation implicated in autism increases inhibitory synaptic transmission in mice. Science 318(5847): 71-76.

Takayanagi Y, Fujita E, Yu Z, Yamagata T, Momoi M Y, Momoi T, Onaka T. (2010) Impairment of social and emotional behaviors in Cadm1-knockout mice. Biochem. Biophys. Res. Commun. 396:703-708.

Tropea D, Giacometti E, Wilson N R, Beard C, Me Curry C, Fu D D, Flannery R, Jaenisch R, Sur M. (2009) Partial reversal of Rett Syndrome-like symptoms in MeCP2 mutant mice. Proc. Natl Acad. Sci. USA 106: 2029-2034.

Vernes, S. C., Newbury, D. F., Abrahams, B. S., Winchester, L., Nicod, J., Groszer, M., Alarcon, M., Oliver, P. L., Davies, K. E., Geschwind, D. H., Monaco, A. P., and Fisher, S. E. (2008). A functional genetic link between distinct developmental language disorders. N. Engl. J. Med. 359, 2337-2345.

Yan J, Noltner K, Feng J, Li W, Schroer R, Skinner C, Zeng W, Schwartz C E, Sommer S S. (2008) Neurexin 1 alpha structural variants associated with autism. Neurosci Lett. 438: 368-370.

Yan Q J, Asafo-Adjei P K, Arnold H M, Brown R E, Bauchwitz R P. (2004) A phenotypic and molecular characterization of the fmr1-tm1Cgr fragile X mouse. Genes Brain Behav. 3:337-359.

Yang M, Crawley J N: Simple behavioural assessment of mouse olfaction. Curr Protoc Neurosci 2009, Chapter 8(Unit 8):24.

Zhiling Y, Fujita E, Tanabe Y, Yamagata T, Momoi T, Momoi M Y. (2008) Mutations in the gene encoding CADM1 are associated with autism spectrum disorder. Biochem. Biophys. Res. Commun. 377:926-929.

Zhao M G, Toyoda H, Ko S W, Ding H K, Wu L J, Zhuo M. (2005) Deficits in trace fear memory and long-term potentiation in a mouse model for fragile X syndrome. J. Neurosci. 25: 7385-7392. (Erratum in: J Neurosci. 2005, 25: 8112).

Zoghbi H Y. (2005) MeCP2 dysfunction in humans and mice. J Child Neurol. 20:736-740.

We claim:

1. A method for treating one or more symptoms in a mammal having autism, comprising administering to the mammal, a pharmaceutically effective amount of a compound comprising cyclic Glycyl-2-Allyl Proline (cG-2-AllylP), cyclic cyclohexyl-G-2MeP, or cyclic cyclopentyl-G-2MeP.

2. The method of claim 1, wherein said compound is formulated in a solution, in a gel, along with one or more excipients, carriers, additives, adjuvants, binders, in a tablet, in a capsule, in a nanocapsule, in a microemulsion, in a coarse emulsion, or in a liquid crystal.

3. The method of claim 1, where the compound is administered either directly or indirectly via the circulation.

4. The method of claim 1, where said compound is administered via a route selected from the group consisting of oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, and vaginal.

5. The method of claim 1, where said effective amount has a lower limit of about 0.001 milligrams per kilogram mass (mg/kg) of the mammal and an upper limit of about 100 mg/kg.

6. The method of claim 1, wherein said treatment produces an improvement in a symptom of the disorder as assessed using one or more clinical tests selected from the group consisting of Aberrant Behavior Checklist Community Edition (ABC), Vineland Adaptive Behavior Scales, Clinical Global Impression of Severity (CGI-S), Clinical Global Impression Improvement (CGI-I), the Caregiver Strain Questionnaire (CSQ), electroencephalogram (EEG) spike frequency, overall power in frequency bands of an EEG, hemispheric coherence of EEG frequencies, stereotypic hand movement, eye tracking, QTc variability, heart rate variability (HRV), respiratory irregularities, and abnormal coupling of cardiac and respiratory function compared to control animals not suffering from said disorder.

7. The method of claim 1, where said treatment reduces one or more symptoms selected from the group consisting of anxiety, impairment in social interaction, impairment in the use of multiple nonverbal behaviors, failure to develop peer relationships appropriate to developmental level, lack of spontaneous seeking to share enjoyment, interests, or achievements, lack of social or emotional reciprocity, impairment in communication, restricted and repetitive interests and behaviors, lack of spontaneous make-believe play, abnormal fear conditioning, abnormal social behaviour, repetitive behaviour, abnormal nocturnal behaviour, seizure activity, abnormal locomotion, abnormal expression of Phospho-ERK1/2, abnormal expression of Phospho-Akt, and bradycardia.

8. A method for treating a symptom of autism in a mammal, comprising administering to the mammal, a compound having the formula:

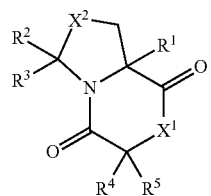

or a pharmaceutically acceptable salt or hydrate thereof, wherein $X^1$ is selected from the group consisting of NR', O and S;
$X^2$ is selected from the group consisting of $CH_2$, NR', O and S;
$R^1, R^2, R^3, R^4$ and $R^5$ are independently selected from the group consisting of —H, —OR', —SR', —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;
or $R^4$ and $R^5$ taken together are —$CH_2$—$(CH_2)_n$-$CH_2$— where n is an integer from 0-6;
or $R^2$ and $R^3$ taken together are —$CH_2$—$(CH_2)_n$—$CH_2$— where n is an integer from 0-6;
with the proviso that when $R^1$=methyl and $R^2=R^3=R^4$=H then $R^5$ # benzyl and;
when $R^1$=H, at least one of $R^2$ and $R^3 \neq$H.

9. The method of claim 8 where $R^1$=methyl.

10. The method of claim 8 where $R^1$=allyl.

11. The method of claim 8 where $R^2=R^3$=methyl and $X^2$=S.

12. The method of claim 8 where $R^1$=allyl, $R^2=R^3=R^4=R$=H, $X^1$=NH, $X^2=CH_2$.

13. The method of claim 8 where $R^1$=methyl, $R^2=R^3$=H, $R^4$ and $R^5$ taken together are —$CH_2$—$(CH_2)_3$—$CH_2$—, $X^1$=NH, $X^2=CH_2$.

14. The method of claim 8 where $R^1$=methyl, $R^2=R^3$=H, $R^4$ and $R^5$ taken together are —$CH_2$—$(CH_2)_2$—$CH_2$—, $X^1$=NH, $X^2=CH_2$.

15. The method of claim 8, wherein said compound is cG-2-AllylP.

16. The method of claim 8, wherein said compound is cyclic cyclohexyl-G-2MeP.

17. The method of claim 8, wherein said compound is or cyclic cyclopentyl-G-2MeP.

18. The method of claim 8, said compound further comprising one or more pharmaceutically acceptable excipients, additives, carriers, or adjuvants in solution.

19. The method of claim 8, said compound further comprising one or more excipients, carriers, additives, adjuvants or binders in a tablet.

20. The method of claim 8, said compound further comprising a microemulsion, coarse emulsion, or liquid crystal in a capsule.

21. The method of claim 8, where the method further comprises administering said compound along with a pharmaceutically acceptable excipient, or in a gel.

22. The method of claim 8, where the method further comprises administering said compound along with a pharmaceutically acceptable excipient and a binder.

23. The method of claim 8, where the method further comprises administering said compound along with a pharmaceutically acceptable excipient and a capsule.

24. The method of claim 8, where said treatment reduces one or more symptoms selected from the group consisting of anxiety, impairment in social interaction, impairment in the use of multiple nonverbal behaviors, failure to develop peer relationships appropriate to developmental level, lack of spontaneous seeking to share enjoyment, interests, or achievements, lack of social or emotional reciprocity, impairment in communication, restricted and repetitive interests and behaviors, lack of spontaneous make-believe play, abnormal fear conditioning, abnormal social behaviour, repetitive behaviour, abnormal nocturnal behaviour, seizure activity, abnormal locomotion, abnormal expression of Phospho-ERK1/2, abnormal expression of Phospho-Akt, and bradycardia.

* * * * *

UNITED STATES PATENT AND TRADEMARK OFFICE
CERTIFICATE OF CORRECTION

PATENT NO. : 11,197,856 B2
APPLICATION NO. : 16/749185
DATED : December 14, 2021
INVENTOR(S) : Lawrence Irwin Glass et al.

It is certified that error appears in the above-identified patent and that said Letters Patent is hereby corrected as shown below:

In the Claims

Column 82, Line 23, Claim 8 replace the symbol "#" with the symbol --≠--.

Column 82, Line 30, Claim 12 replace the fourth symbol "R" with the symbol --$R^5$--.

Column 82, Line 41, Claim 17 delete the word "or" at the end of the line.

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*